(12) United States Patent
Ahmed et al.

(10) Patent No.: US 9,102,638 B2
(45) Date of Patent: Aug. 11, 2015

(54) AMIDOBENZOTHIAZOLES AND PROCESS FOR THE PREPARATION THEREOF

(71) Applicants: Kamal Ahmed, Hyderabad (IN); Adla Malla Reddy, Hyderabad (IN); Suresh Paidakula, Hyderabad (IN); Neigapula Sankara Rao, Hyderabad (IN); Rajesh V. C. R. N. C. Shetti, Hyderabad (IN)

(72) Inventors: Kamal Ahmed, Hyderabad (IN); Adla Malla Reddy, Hyderabad (IN); Suresh Paidakula, Hyderabad (IN); Neigapula Sankara Rao, Hyderabad (IN); Rajesh V. C. R. N. C. Shetti, Hyderabad (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 0 days.

(21) Appl. No.: 13/958,231

(22) Filed: Aug. 2, 2013

(65) Prior Publication Data

US 2013/0317231 A1 Nov. 28, 2013

Related U.S. Application Data

(63) Continuation of application No. PCT/IN2011/000187, filed on Mar. 21, 2011.

(30) Foreign Application Priority Data

Feb. 4, 2011 (IN) .............................. 266/DEL/2011

(51) Int. Cl.
*C07D 417/12* (2006.01)
*C07D 277/82* (2006.01)
(Continued)

(52) U.S. Cl.
CPC ............ *C07D 277/82* (2013.01); *A61K 31/428* (2013.01); *C07D 277/64* (2013.01); *C07D 417/12* (2013.01)

(58) Field of Classification Search
CPC ... C07D 417/12; C07D 277/82; A61K 31/428
See application file for complete search history.

(56) References Cited

U.S. PATENT DOCUMENTS 6,140,330 A * 10/2000 Mori et al. ............... 514/254.03

FOREIGN PATENT DOCUMENTS

WO 2009109986 A1 9/2009

OTHER PUBLICATIONS

Hutchinson, et al.; "Antitumor Benzothiazoles. 14.1 Synthesis and in Vitro Biological Properties of Fluorinated 2-(4-Aminophenyl)benzothiazoles"; J. Med. Chem. 2001, 44, 1446-1455.
(Continued)

*Primary Examiner* — Matthew Coughlin
(74) *Attorney, Agent, or Firm* — St. Onge Steward Johnston & Reens LLC

(57) ABSTRACT

The present invention provides a compound of general formulae A useful as potential anti-cancer agents against human cancer cell lines and a process for the preparation thereof. Where in R, $R_1$, $R_2$=H, alkyl, alkoxy, halo, haloalkyl, halomethoxy, nitro and G=

Formula A

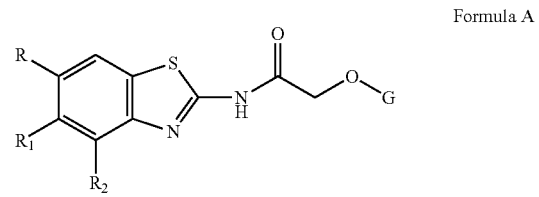

Where in R, $R_1$, $R_2$=H, alkyl, alkoxy, halo, haloalkyl, halomethoxy, nitro and G=

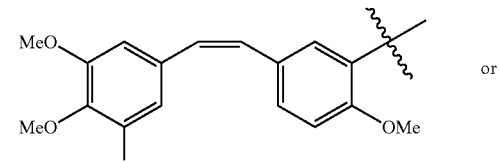

or

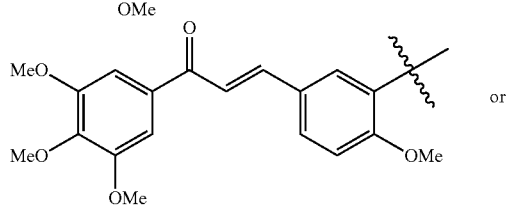

or

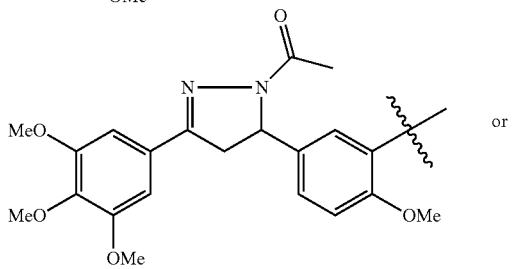

or

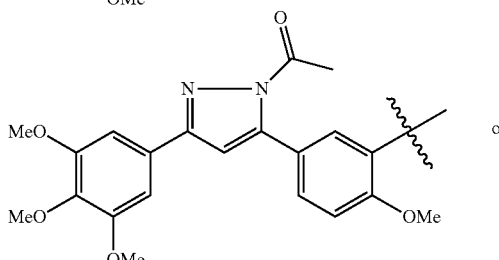

or

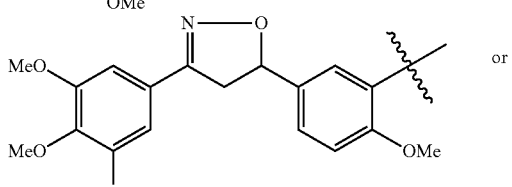

or

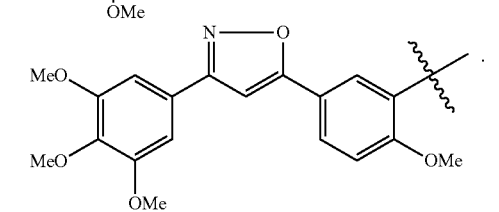

6 Claims, 5 Drawing Sheets

(51) Int. Cl.
*A61K 31/428* (2006.01)
*C07D 277/64* (2006.01)

(56) References Cited

OTHER PUBLICATIONS

Mortimer, et al.; "Antitumor Benzothiazoles. 26.1 2-(3,4-Dimethoxyphenyl)-5-fluorobenzothiazole (GW 610, NSC 721648), a Simple Fluorinated 2-Arylbenzothiazole, Shows Potent and Selective Inhibitory Activity against Lung, Colon, and Breast Cancer Cell Lines"; J. Med. Chem. 2006, 49, 179-185.

Shi, et al.; "Antitumor Benzothiazoles. 3.1 Synthesis of 2-(4-Aminophenyl)benzothiazoles and Evaluation of Their Activities against Breast Cancer Cell Lines in Vitro and in Vivo"; J. Med. Chem. 1996, 39, 3375-3384.

Kashiyama, et al; "Antitumor Benzothiazoles. 8.1 Synthesis, Metabolic Formation, and Biological Properties of the C-and N-Oxidation Products of Antitumor 2-(4-Aminophenyl)-benzothiazoles"; J. Med. Chem. 1999, 42, 4172-4184.

Ducki, et al.; "Combretastatin-like chalcones as inhibitors of microtubule polymerization. Part 1: Synthesis and biological evaluation of antivascular activity"; Bioorganic & Medicinal Chemistry 17 (2009) 7698-7710.

Johnson, et al.; "Design, synthesis, and biological testing of pyrazoline derivatives of combretastatin-A4"; Bioorganic & Medicinal Chemistry Letters 17 (2007) 5897-5901.

Simoni, et al.; "Heterocyclic and Phenyl Double-Bond-Locked Combretastatin Analogues Possessing Potent Apoptosis-Inducing Activity in HL60 and in MDR Cell Lines"; J. Med. Chem. 2005, 48, 723-736.

Kaffy, et al.; "Isoxazole-type derivatives related to combretastatin A-4, synthesis and biological evaluation"; Bioorganic & Medicinal Chemistry 14 (2006) 4067-4077.

International Search Report Application No. PCT/IN2011/000187 Completed: Jul. 5, 2011; Mailing Date: Jul. 22, 2011 3 pages.

Tron, et al.; "Medicinal Chemistry of Combretastatin A4: Present and Future Directions"; © Copyright 2006 by the American Chemical Society; vol. 49, No. 11; pp. 3033-3044.

Bhat, et al.; "Synthesis and biological evaluation of chalcones and their derived pyrazoles as potential cytotoxic agents"; Bioorganic & Medicinal Chemistry Letters 15 (2005) 3177-3180.

Pirali, et al.; "Synthesis and Cytotoxic Evaluation of Combretafurans, Potential Scaffolds for Dual-Action Antitumoral Agents"; J. Med. Chem. 2006, 49, 5372-5376.

LeBlanc, et al.; "Synthesis and cytotoxicity of epoxide and pyrazole analogs of the combretastatins"; Bioorganic & Medicinal Chemistry 13 (2005) 6025-6034.

Patil, et al.; "Synthesis and Primary Cytotoxicity Evaluation of New 5-Benzylidene-2, 4-Thiazolidinedione Derivatives"; European Journal of Medical Chemistry; 45 (2010) 4539-4544.

\* cited by examiner

R = H, alkyl, alkoxy, halo, haloalkyl, halomethoxy, nitro and G =

AMIDOBENZOTHIAZOLES AND PROCESS FOR THE PREPARATION THEREOF

FIELD OF THE INVENTION

The present invention relates to amidobenzothiazoles of general formula A

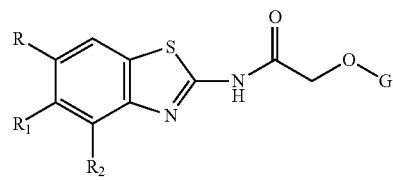

General formula A wherein R, $R_1$, $R_2$=H, alkoxy, halo, haloalkyl, halomethyl or nitro and

G=

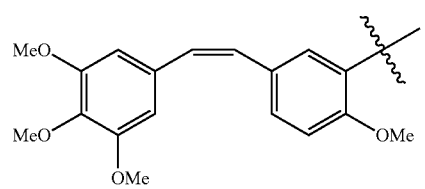

or

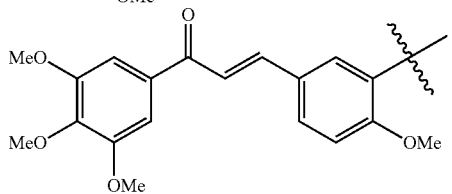

or

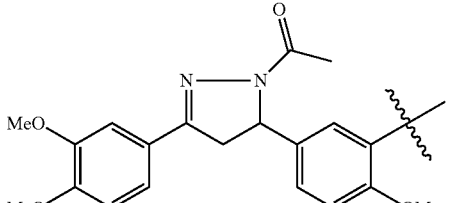

or

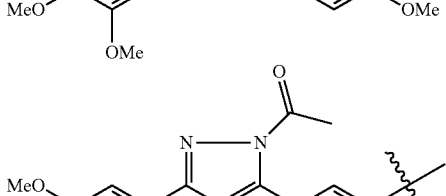

or

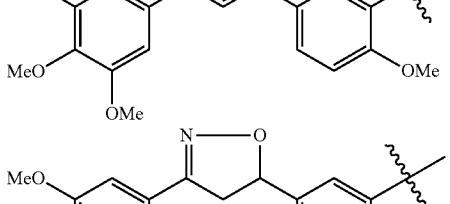

or

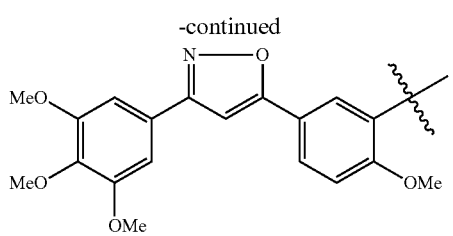

and structural formula of the representative compounds are:

8a-v

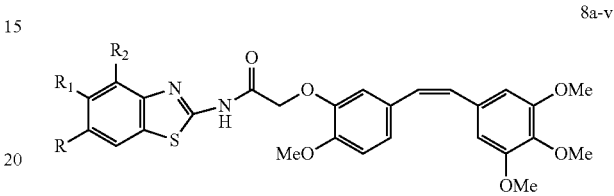

9a-v

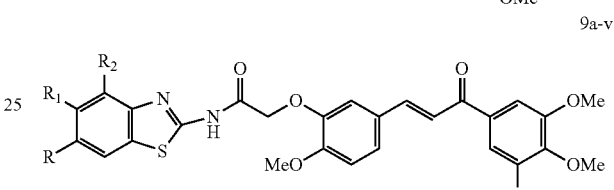

10a-v

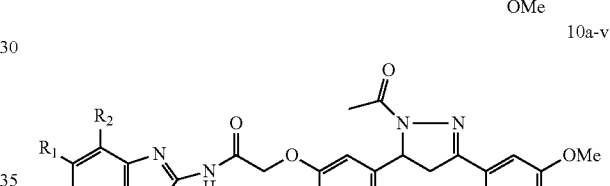

11a-v

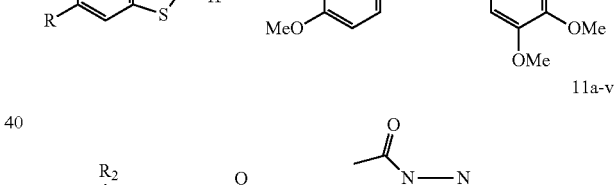

12a-v

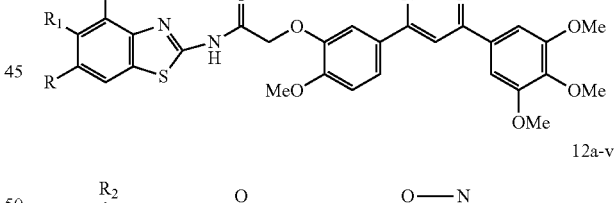

13a-v

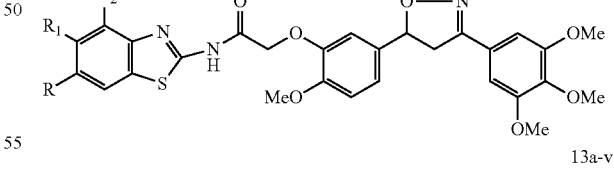

Present invention further relates to amidobenzothiazoles of general formula A as anticancer agents and process for the preparation thereof.

Present invention further relates to olefine, chalcone, pyrazoline, pyrazole, isoxazoline and isoxazoles linked to aminobenzothiazoles with amide bond useful as anticancer agents.

BACKGROUND OF THE INVENTION

Inhibition of tubulin polymerization is the target of many antitumoural agents known as antimitotic agents or spindle poisons colchicines, podophyllotoxins and combretastatins are representative examples of compounds that inhibit microtubule assembly by binding to tubulin. Benzothiazoles are small synthetic molecules that contain a benzene ring fused to a thiazole ring. These simple molecules have shown remarkable anti-cancer properties and some of them are undergoing, evaluation in clinical trials (Shi, D.-F.; Bradshaw, T. D.; Wrigley, S.; McCall, C. J.; Lelieveld, P.; Fichtner, I.; Stevens, M. F. G. *J. Med. Chem.* 1996, 39, 3375; Kashiyama, E.; Hutchinson, I.; Chua, M.-S.; Stinson, S. F.; Phillips, L. R.; Kaur, G.; Sausville, E. A.; Bradshaw, T. D.; Westwell, A. D.; Stevens, M. F. G. *J. Med. Chem.* 1999, 42, 4172; Hutchinson, I.; Chua, M.-S.; Browne, H. L.; Trapani, V.; Bradshaw, T. D.; Westwell, A. D.; Stevens, M. F. G. *J. Med. Chem.* 2001, 44, 1446). Recently Westwell and coworkers have prepared a series of benzothiazole derivatives and evaluated for anticancer activity, One of these analogues has shown excellent anticancer activity (Mortimer, C. G.; Wells, G.; Crochard, J.-P.; Stone, E. L.; Bradshaw, T. D.; Stevens, M. F. G.; Westwell, A. D. *J. Med. Chem.* 2006, 49, 179). Many chalcone, pyrazoline, isoxazole and isoxazoline type moieties related to combretastain A-4 showed potential biological properties particularly anticancer activity (Sylvie Ducki, David Rennison, Meiko Woo, Alexander Kendall, Jérémie Fournier Dit Chabert, Alan T. McGown, Nicholas J. Lawrence. *Bioorg. Med. Chem*, Vol 17, 22, 2009, 7698-7710; Regan LeBlanc, John Dickson, Toni Brown, Michelle Stewart, Hari N. Pati, Don VanDerveer, Hadi Arman, Jeff Harris, William Pennington, Herman L. Holt Jr., Moses Lee. *Bioorg. Med. Chem*, Volume 13, 21, 2005, 6025-6034; Marlie Johnson, Brent Younglove, Lauren Lee, Regan LeBlanc, Herman Holt Jr., Patrice Hills, Hilary Mackay, Toni Brown, Susan L. Mooberry, Moses Lee. *Bioorg. Med. Chem Lett*, Vol 17, 21, 2007, 5897-5901; B. A. Bhat, K. L. Dhar, S. C. Puri, A. K. Saxena, M. Shanmugavel, G. N. Qazi. *Bioorg. Med. Chem Lett*, Vol 15, 12, 2005, 3177-3180; Simoni, D.; Grisolia, G.; Giannini, G.; Roberti, M.; Rondanin, R.; Piccagli, L.; Baruchello, R.; Rossi, M.; Romagnoli, R.; Invidiata, F. P.; Grimaudo, S.; Jung, M. K.; Hamel, E.; Gebbia, N.; Crosta, L.; Abbadessa, V.; DiCristina, A.; Dusonchet, L.; Meli, M.; Tolomeo, M. J. Med. Chem. 2005, 48, 723, Julia Kaffy, a Rene'e Pontikis, a, Danie'le Carrez, b Alain Croisy, Claude Monnereta and Jean-Claude Florent. Bioorg. Med. Chem. 2006, 14, 4067-4077, Gian Ceasure Tron, Tracy Pirali, Giovanni sorba, Francesca pagliai, Sara Buasacca and Armado A. Genazzani. J. Med. Chem. 2006, 49, 3033-3044. and Tracey Pirali, Sara buasacca, Lorena Beltrami, Daniela Imovilli, Francesca Paliai, Gianluca Migilio, Alberto Massrotti, Luisella Verotta, Gian Cesare Tron, Givanni Sorba, and Armado A. Genazzani. J. Med. Chem. 2006, 49, 5372-5376). Some of the heterocyclic bridged Combretastains showed an attractive profile of cytotoxicity and were able to induce apoptosis at lower concentrations.

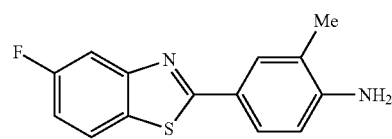

5F-203

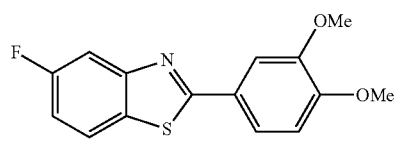

GW 610

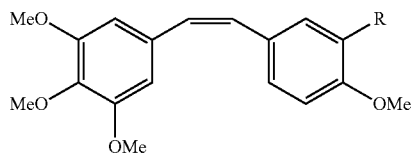

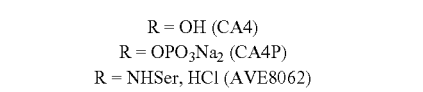

R = OH (CA4)
R = OPO$_3$Na$_2$ (CA4P)
R = NHSer, HCl (AVE8062)

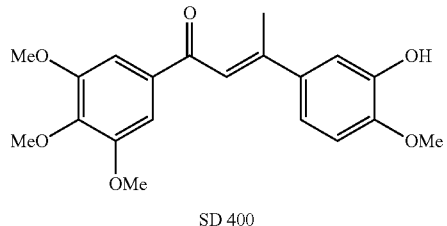

SD 400

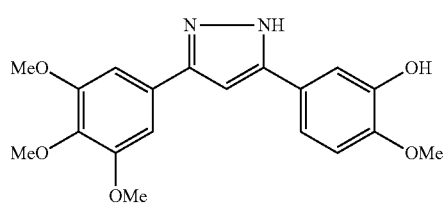

Pyrazole derivative

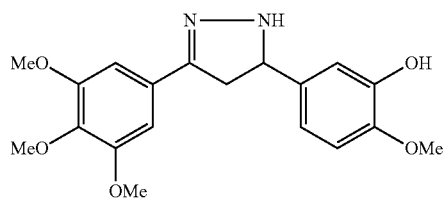

Pyrazoline derivative

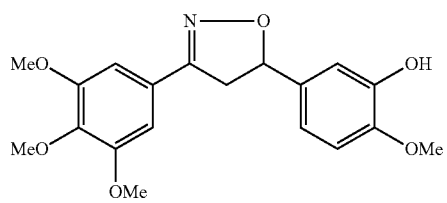

Isoxazoline derivative

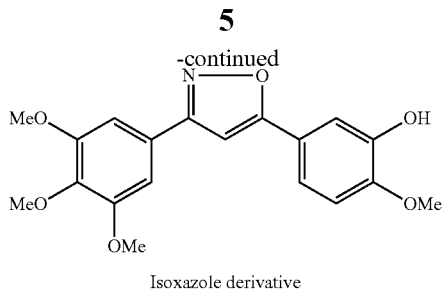

Isoxazole derivative

OBJECTIVE OF THE INVENTION

The main objective of the present invention is to provide amidobenzothiazole of general formula A useful as anti-cancer agents.

Yet another object of the present invention is to provide a process for the preparation of amidobenzothiazole of general formula A.

SUMMARY OF THE INVENTION

Accordingly, present invention relates to amidobenzothiazole of general formula A General formula A

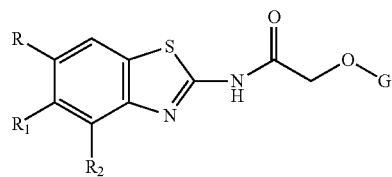

wherein R, $R_1$, $R_2$=H, alkoxy, halo, haloalkyl, halomethyl or nitro and

G=

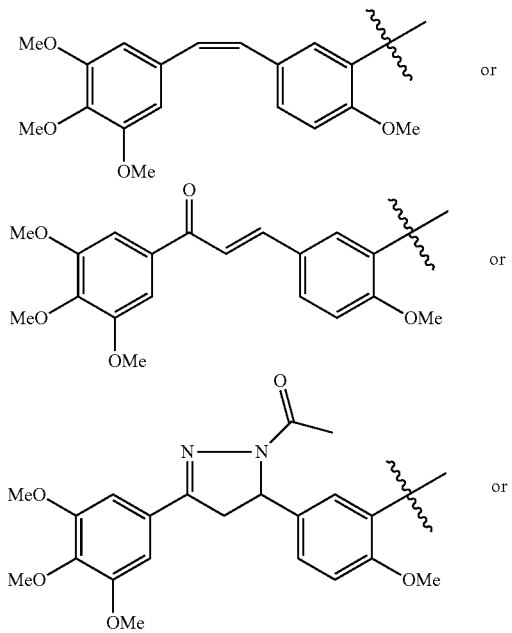

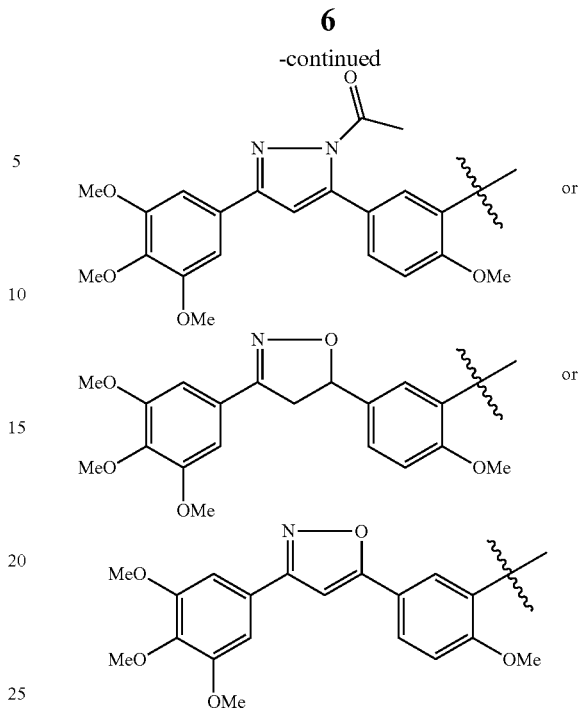

In an embodiment of the present invention, chemical formulas of the representative compounds are:

N1-(1,3-benzothiazol-2-yl)-2-{2-methoxy-5-[(Z)-2-(3,4,5-trimethoxyphenyl)-1-ethenyl]phenoxy}acetamide (8a);

N1-(6-nitro-1,3-benzothiazol-2-yl)-2-{2-methoxy-5-[(Z)-2-(3,4,5-trimethoxyphenyl)-1-ethenyl]phenoxy}acetamide (8b);

N1-(6-methyl-1,3-benzothiazol-2-yl)-2-{2-methoxy-5-[(Z)-2-(3,4,5-trimethoxyphenyl)-1-ethenyl]phenoxy}acetamide (8e);

N1-(6-ethyl-1,3-benzothiazol-2-yl)-2-{2-methoxy-5-[(Z)-2-(3,4,5-trimethoxyphenyl)-1-ethenyl]phenoxy}acetamide (8d);

N1-(6-fluoro-1,3-benzothiazol-2-yl)-2-{2-methoxy-5-[(Z)-2-(3,4,5-trimethoxyphenyl)-1-ethenyl]phenoxy}acetamide (8e);

N1-(6-chloro-1,3-benzothiazol-2-yl)-2-{2-methoxy-5-[(Z)-2-(3,4,5-trimethoxyphenyl)-1-ethenyl]phenoxy}acetamide (8f);

N1-(6-methoxy-1,3-benzothiazol-2-yl)-2-{2-methoxy-5-[(Z)-2-(3,4,5-trimethoxyphenyl)-1-ethenyl]phenoxy}acetamide (8g);

N1-(6-ethoxy-1,3-benzothiazol-2-yl)-2-{2-methoxy-5-[(Z)-2-(3,4,5-trimethoxyphenyl)-1-ethenyl]phenoxy}acetamide (8h);

N1-(6-(trifluoromethyl)-1,3-benzothiazol-2-yl)-2-{2-methoxy-5-[(Z)-2-(3,4,5-trimethoxyphenyl)-1-ethenyl]phenoxy}acetamide (8i);

N1-(6-(trifluoromethoxy)-1,3-benzothiazol-2-yl)-2-{2-methoxy-5-[(Z)-2-(3,4,5-trimethoxyphenyl)-1-ethenyl]phenoxy}acetamide (8j);

N1-(4-methyl-1,3-benzothiazol-2-yl)-2-{2-methoxy-5-[(Z)-2-(3,4,5-trimethoxyphenyl)-1-ethenyl]phenoxy}acetamide (8k);

N1-(5-nitro-1,3-benzothiazol-2-yl)-2-{2-methoxy-5-[(Z)-2-(3,4,5-trimethoxyphenyl)-1-ethenyl]phenoxy}acetamide (8l);

N1-(5-methyl-1,3-benzothiazol-2-yl)-2-{2-methoxy-5-[(Z)-2-(3,4,5-trimethoxyphenyl)-1-ethenyl]phenoxy}acetamide (8m);

N1-(5-ethyl-1,3-benzothiazol-2-yl)-2-{2-methoxy-5-[(Z)-2-(3,4,5-trimethoxyphenyl)-1-ethenyl]phenoxy}acetamide (8n);

N1-(5-fluoro-1,3-benzothiazol-2-yl)-2-{2-methoxy-5-[(Z)-2-(3,4,5-trimethoxyphenyl)-1-ethenyl]phenoxy}acetamide (8o);

N1-(5-chloro-1,3-benzothiazol-2-yl)-2-{2-methoxy-5-[(Z)-2-(3,4,5-trimethoxyphenyl)-1-ethenyl]phenoxy}acetamide (8p);

N1-(5-methoxy-1,3-benzothiazol-2-yl)-2-{2-methoxy-5-[(Z)-2-(3,4,5-trimethoxyphenyl)-1-ethenyl]phenoxy}acetamide (8q);

N1-(5-ethoxy-1,3-benzothiazol-2-yl)-2-{2-methoxy-5-[(Z)-2-(3,4,5-trimethoxyphenyl)-1-ethenyl]phenoxy}acetamide (8r);

N1-(5-(trifluoromethyl)-1,3-benzothiazol-2-yl)-2-{2-methoxy-5-[(Z)-2-(3,4,5-trimethoxyphenyl)-1-ethenyl]phenoxy}acetamide (8s);

N1-(5-(trifluoromethoxy)-1,3-benzothiazol-2-yl)-2-{2-methoxy-5-[(Z)-2-(3,4,5-trimethoxyphenyl)-1-ethenyl]phenoxy}acetamide (8t);

N1-(5,6-dimethyl-1,3-benzothiazol-2-yl)-2-{2-methoxy-5-[(Z)-2-(3,4,5-trimethoxyphenyl)-1-ethenyl]phenoxy}acetamide (8u);

N1-(5,6-difluoro-1,3-benzothiazol-2-yl)-2-{2-methoxy-5-[(Z)-2-(3,4,5-trimethoxyphenyl)-1-ethenyl]phenoxy}acetamide (8v);

N1-(1,3-benzothiazol-2-yl)-2-{2-methoxy-5-[(E)-3-oxo-3-(3,4,5-trimethoxyphenyl)-1-propenyl]phenoxy}acetamide (9a);

N1-(6-nitro-1,3-benzothiazol-2-yl)-2-{2-methoxy-5-[(E)-3-oxo-3-(3,4,5-trimethoxyphenyl)-1-propenyl]phenoxy}acetamide (9b);

N1-(6-methyl-1,3-benzothiazol-2-yl)-2-{2-methoxy-5-[(E)-3-oxo-3-(3,4,5-trimethoxyphenyl)-1-propenyl]phenoxy}acetamide (9c);

N1-(6-ethyl-1,3-benzothiazol-2-yl)-2-{2-methoxy-5-[(E)-3-oxo-3-(3,4,5-trimethoxyphenyl)-1-propenyl]phenoxy}acetamide (9d);

N1-(6-fluoro-1,3-benzothiazol-2-yl)-2-{2-methoxy-5-[(E)-3-oxo-3-(3,4,5-trimethoxyphenyl)-1-propenyl]phenoxy}acetamide (9e);

N1-(6-chloro-1,3-benzothiazol-2-yl)-2-{2-methoxy-5-[(E)-3-oxo-3-(3,4,5-trimethoxyphenyl)-1-propenyl]phenoxy}acetamide (9f);

N1-(6-methoxy-1,3-benzothiazol-2-yl)-2-{2-methoxy-5-[(E)-3-oxo-3-(3,4,5-trimethoxyphenyl)-1-propenyl]phenoxy}acetamide (9g);

N1-(6-ethoxy-1,3-benzothiazol-2-yl)-2-{2-methoxy-5-[(E)-3-oxo-3-(3,4,5-trimethoxyphenyl)-1-propenyl]phenoxy}acetamide (9h);

N1-(6-(trifluoromethyl)-1,3-benzothiazol-2-yl)-2-{2-methoxy-5-[(E)-3-oxo-3-(3,4,5-trimethoxyphenyl)-1-propenyl]phenoxy}acetamide (9i);

N1-(6-(trifluoromethoxy)-1,3-benzothiazol-2-yl)-2-{2-methoxy-5-[(E)-3-oxo-3-(3,4,5-trimethoxyphenyl)-1-propenyl]phenoxy}acetamide (9j);

N1-(4-methyl-1,3-benzothiazol-2-yl)-2-{2-methoxy-5-[(E)-3-oxo-3-(3,4,5-trimethoxyphenyl)-1-propenyl]phenoxy}acetamide (9k);

N1-(5-nitro-1,3-benzothiazol-2-yl)-2-{2-methoxy-5-[(E)-3-oxo-3-(3,4,5-trimethoxyphenyl)-1-propenyl]phenoxy}acetamide (9l);

N1-(5-methyl-1,3-benzothiazol-2-yl)-2-{2-methoxy-5-[(E)-3-oxo-3-(3,4,5-trimethoxyphenyl)-1-propenyl]phenoxy}acetamide (9m);

N1-(5-ethyl-1,3-benzothiazol-2-yl)-2-{2-methoxy-5-[(E)-3-oxo-3-(3,4,5-trimethoxyphenyl)-1-propenyl]phenoxy}acetamide (9n);

N1-(5-fluoro-1,3-benzothiazol-2-yl)-2-{2-methoxy-5-[(E)-3-oxo-3-(3,4,5-trimethoxyphenyl)-1-propenyl]phenoxy}acetamide (9o);

N1-(5-chloro-1,3-benzothiazol-2-yl)-2-{2-methoxy-5-[(E)-3-oxo-3-(3,4,5-trimethoxyphenyl)-1-propenyl]phenoxy}acetamide (9p);

N1-(5-methoxy-1,3-benzothiazol-2-yl)-2-{2-methoxy-5-[(E)-3-oxo-3-(3,4,5-trimethoxyphenyl)-1-propenyl]phenoxy}acetamide (9q);

N1-(5-ethoxy-1,3-benzothiazol-2-yl)-2-{2-methoxy-5-[(E)-3-oxo-3-(3,4,5-trimethoxyphenyl)-1-propenyl]phenoxy}acetamide (9r);

N1-(5-(trifluoromethyl)-1,3-benzothiazol-2-yl)-2-{2-methoxy-5-[(E)-3-oxo-3-(3,4,5-trimethoxyphenyl)-1-propenyl]phenoxy}acetamide (9s);

N1-(5-(trifluoromethoxy)-1,3-benzothiazol-2-yl)-2-{2-methoxy-5-[(E)-3-oxo-3-(3,4,5-trimethoxyphenyl)-1-propenyl]phenoxy}acetamide (9t);

N1-(5,6-dimethyl-1,3-benzothiazol-2-yl)-2-{2-methoxy-5-[(E)-3-oxo-3-(3,4,5-trimethoxyphenyl)-1-propenyl]phenoxy}acetamide (9u);

N1-(5,6-difluoro-1,3-benzothiazol-2-yl)-2-{2-methoxy-5-[(E)-3-oxo-3-(3,4,5-trimethoxyphenyl)-1-propenyl]phenoxy}acetamide (9v);

N1-(1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10a);

N1-(6-nitro-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10b);

N1-(6-methyl-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10c);

N1-(6-ethyl-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10d);

N1-(6-fluoro-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10e);

N1-(6-chloro-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10f);

N1-(6-methoxy-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10g);

N1-(6-ethoxy-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10h);

N1-(6-(trifluoromethyl)-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10i);

N1-(6-(trifluoromethoxy)-1,3-benzothiazol-2-yl)-2-{5-[1-acetyl-3-(3,4,5-trimethoxy phenyl)-4,5-dihydro-1H-5-pyrazolyl]-2-methoxyphenoxy}acetamide (10j);

N1-(4-methyl-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10k);

N1-(5-nitro-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10l);

N1-(5-methyl-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10m);

N1-(5-ethyl-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10n);

N1-(5-fluoro-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10o);

N1-(5-chloro-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10p);

N1-(5-methoxy-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10q);

N1-(5-ethoxy-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10r);

N1-(5-(trifluoromethyl)-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10s);

N1-(5-(trifluoromethoxy)-1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10t);

N1-(5,6-dimethyl-1,3-benzothiazol-2-yl)-2-5-[1-acetyl-3-(3,4,5-trimethoxyphenyl)-4,5-dihydro-1H-5-pyrazolyl]-2-methoxyphenoxyacetamide (10u);

N1-(5,6-difluoro-1,3-benzothiazol-2-yl)-2-5-[1-acetyl-3-(3,4,5-trimethoxyphenyl)-4,5-dihydro-1H-5-pyrazolyl]-2-methoxyphenoxyacetamide (10v);

N1-(1,3-benzothiazol-2-yl)-2-{5-[1-acetyl-3-(3,4,5-trimethoxyphenyl)-1H-5-pyrazolyl]-2-methoxyphenoxy}acetamide (11a);

N1-(6-nitro-1,3-benzothiazol-2-yl)-2-{5-[1-acetyl-3-(3,4,5-trimethoxyphenyl)-1H-5-pyrazolyl]-2-methoxyphenoxy}acetamide (11b);

N1-(6-methyl-1,3-benzothiazol-2-yl)-2-{5-[1-acetyl-3-(3,4,5-trimethoxyphenyl)-1H-5-pyrazolyl]-2-methoxyphenoxy}acetamide (11c);

N1-(6-ethyl-1,3-benzothiazol-2-yl)-2-{5-[1-acetyl-3-(3,4,5-trimethoxyphenyl)-1H-5-pyrazolyl]-2-methoxyphenoxy}acetamide (11d);

N1-(6-fluoro-1,3-benzothiazol-2-yl)-2-{5-[1-acetyl-3-(3,4,5-trimethoxyphenyl)-1H-5-pyrazolyl]-2-methoxyphenoxy}acetamide (11e);

N1-(6-chloro-1,3-benzothiazol-2-yl)-2-{5-[1-acetyl-3-(3,4,5-trimethoxyphenyl)-1H-5-pyrazolyl]-2-methoxyphenoxy}acetamide (11f);

N1-(6-methoxy-1,3-benzothiazol-2-yl)-2-{5-[1-acetyl-3-(3,4,5-trimethoxyphenyl)-1H-5-pyrazolyl]-2-methoxyphenoxy}acetamide (11g);

N1-(6-ethoxy-1,3-benzothiazol-2-yl)-2-{5-[1-acetyl-3-(3,4,5-trimethoxyphenyl)-1H-5-pyrazolyl]-2-methoxyphenoxy}acetamide (11h);

N1-(6-(trifluoromethyl)-1,3-benzothiazol-2-yl)-2-{5-[1-acetyl-3-(3,4,5-trimethoxy phenyl)-1H-5-pyrazolyl]-2-methoxyphenoxy}acetamide (11i);

N1-(6-(trifluoromethoxy)-1,3-benzothiazol-2-yl)-2-{5-[1-acetyl-3-(3,4,5-trimethoxy phenyl)-1H-5-pyrazolyl]-2-methoxyphenoxy}acetamide (11j);

N1-(4-methyl-1,3-benzothiazol-2-yl)-2-{5-[1-acetyl-3-(3,4,5-trimethoxyphenyl)-1H-5-pyrazolyl]-2-methoxyphenoxy}acetamide (11k);

N1-(5-nitro-1,3-benzothiazol-2-yl)-2-{5-[1-acetyl-3-(3,4,5-trimethoxyphenyl)-1H-5-pyrazolyl]-2-methoxyphenoxy}acetamide (11l);

N1-(5-methyl-1,3-benzothiazol-2-yl)-2-{5-[1-acetyl-3-(3,4,5-trimethoxyphenyl)-1H-5-pyrazolyl]-2-methoxyphenoxy}acetamide (11m);

N1-(5-ethyl-1,3-benzothiazol-2-yl)-2-{5-[1-acetyl-3-(3,4,5-trimethoxyphenyl)-1H-5-pyrazolyl]-2-methoxyphenoxy}acetamide (11n);

N1-(5-fluoro-1,3-benzothiazol-2-yl)-2-{5-[1-acetyl-3-(3,4,5-trimethoxyphenyl)-1H-5-pyrazolyl]-2-methoxyphenoxy}acetamide (11o);

N1-(5-chloro-1,3-benzothiazol-2-yl)-2-{5-[1-acetyl-3-(3,4,5-trimethoxyphenyl)-1H-5-pyrazolyl]-2-methoxyphenoxy}acetamide (11p);

N1-(5-methoxy-1,3-benzothiazol-2-yl)-2-{5-[1-acetyl-3-(3,4,5-trimethoxyphenyl)-1H-5-pyrazolyl]-2-methoxyphenoxy}acetamide (11q);

N1-(5-ethoxy-1,3-benzothiazol-2-yl)-2-{5-[1-acetyl-3-(3,4,5-trimethoxyphenyl)-1H-5-pyrazolyl]-2-methoxyphenoxy}acetamide (11r);

N1-(5-(trifluoromethyl)-1,3-benzothiazol-2-yl)-2-{5-[1-acetyl-3-(3,4,5-trimethoxy phenyl-1H-5-pyrazolyl]-2-methoxyphenoxy}acetamide (11s);

N1-(5-(trifluoromethoxy)-1,3-benzothiazol-2-yl)-2-{5-[1-acetyl-3-(3,4,5-trimethoxy phenyl)-1H-5-pyrazolyl]-2-methoxyphenoxy}acetamide (11t);

N1-(5,6-dimethyl-1,3-benzothiazol-2-yl)-2-5-[1-acetyl-3-(3,4,5-trimethoxyphenyl)-1H-5-pyrazolyl]-2-methoxyphenoxyacetamide (11u);

N1-(5,6-difluoro-1,3-benzothiazol-2-yl)-2-5-[1-acetyl-3-(3,4,5-trimethoxyphenyl)-1H-5-pyrazolyl]-2-methoxyphenoxyacetamide (11v);

N1-(1,3-benzothiazol-2-yl)-2-{2-methoxy-5-[3-(3,4,5-trimethoxyphenyl)-4,5-dihydro-5-isoxazolyl]-2-methoxyphenoxy}acetamide (12a);

N1-(6-nitro-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12b);

N1-(6-methyl-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12c);

N1-(6-ethyl-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12d);

N1-(6-fluoro-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12e);

N1-(6-chloro-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12f);

N1-(6-methoxy-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12g);

N1-(6-ethoxy-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12h);

N1-(6-(trifluoromethyl)-1,3-benzothiazol-2-yl)-2-{2-Methoxy-5-[3-(3,4,5-trimethoxy phenyl)-4,5-dihydro-5-isoxazolyl]-2-methoxyphenoxy}acetamide (12i);

N1-(6-(trifluoromethoxy)-1,3-benzothiazol-2-yl)-2-{2-methoxy-5-[3-(3,4,5-trimethoxy phenyl)-4,5-dihydro-5-isoxazolyl]-2-methoxyphenoxy}acetamide (12j);

N1-(4-methyl-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12k);

N1-(5-nitro-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12l);

N1-(5-methyl-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12m);

N1-(5-ethyl-1,3-benzothiazol-2-yl)-2-{2-methoxy-5-[3-(3, 4,5-trimethoxyphenyl)-4,5-dihydro-5-isoxazolyl]-2-methoxyphenoxy}acetamide (12n);
N1-(5-fluoro-1,3-benzothiazol-2-yl)-2-{2-methoxy-5-[3-(3, 4,5-trimethoxyphenyl)-4,5-dihydro-5-isoxazolyl]-2-methoxyphenoxy}acetamide (12o);
N1-(5-chloro-1,3-benzothiazol-2-yl)-2-{2-methoxy-5-[3-(3, 4,5-trimethoxyphenyl)-4,5-dihydro-5-isoxazolyl]-2-methoxyphenoxy}acetamide (12p);
N1-(5-methoxy-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12q);
N1-(5-ethoxy-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12r);
N1-(5-(trifluoromethyl)-1,3-benzothiazol-2-yl)-2-{2-methoxy-5-[3-(3,4,5-trimethoxy phenyl)-4,5-dihydro-5-isoxazolyl]-2-methoxyphenoxy}acetamide (12s);
N1-(5-(trifluoromethoxy)-1,3-benzothiazol-2-yl)-2-{2-methoxy-5-[3-(3,4,5-trimethoxy phenyl)-4,5-dihydro-5-isoxazolyl]-2-methoxyphenoxy}acetamide (12t);
N1-(5,6-dimethyl-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12u);
N1-(5,6-difluoro-1,3-benzothiazol-2-yl)-2-{2-methoxy-5-[3-(3,4,5-trimethoxyphenyl)-4,5-dihydro-5-isoxazolyl]-2-methoxyphenoxy}acetamide (12v);
N1-(1,3-benzothiazol-2-yl)-2-{2-methoxy-5-[3-(3,4,5-trimethoxyphenyl)-5-isoxazolyl]-2-methoxyphenoxy}acetamide (13a);
N1-(6-nitro-1,3-benzothiazol-2-yl)-2-{2-methoxy-5-[3-(3,4,5-trimethoxyphenyl)-5-isoxazolyl]-2-methoxyphenoxy}acetamide (13b);
N1-(6-methyl-1,3-benzothiazol-2-yl)-2-{2-methoxy-5-[3-(3,4,5-trimethoxyphenyl)-5-isoxazolyl]-2-methoxyphenoxy}acetamide (13c);
N1-(6-ethyl-1,3-benzothiazol-2-yl)-2-{2-methoxy-5-[3-(3, 4,5-trimethoxyphenyl)-5-isoxazolyl]-2-methoxyphenoxy}acetamide (13d);
N1-(6-fluoro-1,3-benzothiazol-2-yl)-2-{2-methoxy-5-[3-(3, 4,5-trimethoxyphenyl)-5-isoxazolyl]-2-methoxyphenoxy}acetamide (13e);
N1-(6-chloro-1,3-benzothiazol-2-yl)-2-{2-methoxy-5-[3-(3, 4,5-trimethoxyphenyl)-5-isoxazolyl]-2-methoxyphenoxy}acetamide (13f);
N1-(6-methoxy-1,3-benzothiazol-2-yl)-2-{2-methoxy-5-[3-(3,4,5-trimethoxyphenyl)-5-isoxazolyl]-2-methoxyphenoxy}acetamide (13g);
N1-(6-ethoxy-1,3-benzothiazol-2-yl)-2-{2-methoxy-5-[3-(3,4,5-trimethoxyphenyl)-5-isoxazolyl]-2-methoxyphenoxy}acetamide (13h);
N1-(6-(trifluoromethyl)-1,3-benzothiazol-2-yl)-2-{2-methoxy-5-[3-(3,4,5-trimethoxy phenyl)-5-isoxazolyl]-2-methoxyphenoxy}acetamide (13i);
N1-(6-(trifluoromethoxy)-1,3-benzothiazol-2-yl)-2-{2-methoxy-5-[3-(3,4,5-trimethoxy phenyl-5-isoxazolyl]-2-methoxyphenoxy}acetamide (13j);
N1-(4-methyl-1,3-benzothiazol-2-yl)-2-{2-methoxy-5-[3-(3,4,5-trimethoxyphenyl)-5-isoxazolyl]-2-methoxyphenoxy}acetamide (13k);
N1-(5-nitro-1,3-benzothiazol-2-yl)-2-{2-methoxy-5-[3-(3, 4,5-trimethoxyphenyl)-5-isoxazolyl]-2-methoxyphenoxy}acetamide (13l);
N1-(5-methyl-1,3-benzothiazol-2-yl)-2-{2-methoxy-5-[3-(3,4,5-trimethoxyphenyl)-5-isoxazolyl]-2-methoxyphenoxy}acetamide (13m);
N1-(5-ethyl-1,3-benzothiazol-2-yl)-2-{2-methoxy-5-[3-(3, 4,5-trimethoxyphenyl)-5-isoxazolyl]-2-methoxyphenoxy}acetamide (13n);
N1-(5-fluoro-1,3-benzothiazol-2-yl)-2-{2-methoxy-5-[3-(3, 4,5-trimethoxyphenyl)-5-isoxazolyl]-2-methoxyphenoxy}acetamide (13o);
N1-(5-chloro-1,3-benzothiazol-2-yl)-2-{2-methoxy-5-[3-(3, 4,5-trimethoxyphenyl)-5-isoxazolyl]-2-methoxyphenoxy}acetamide (13p);
N1-(5-methoxy-1,3-benzothiazol-2-yl)-2-{2-methoxy-5-[3-(3,4,5-trimethoxyphenyl)-5-isoxazolyl]-2-methoxyphenoxy}acetamide (13q);
N1-(5-ethoxy-1,3-benzothiazol-2-yl)-2-{2-methoxy-5-[3-(3,4,5-trimethoxyphenyl)-5-isoxazolyl]-2-methoxyphenoxy}acetamide (13r);
N1-(5-(trifluoromethyl)-1,3-benzothiazol-2-yl)-2-{2-methoxy-5-[3-(3,4,5-trimethoxy phenyl)-5-isoxazolyl]-2-methoxyphenoxy}acetamide (13s);
N1-(5-(trifluoromethoxy)-1,3-benzothiazol-2-yl)-2-{2-methoxy-5-[3-(3,4,5-trimethoxy phenyl)-5-isoxazolyl]-2-methoxyphenoxy}acetamide (13t);
N1-(5,6-dimethyl-1,3-benzothiazol-2-yl)-2-{2-methoxy-5-[3-(3,4,5-trimethoxyphenyl)-5-isoxazolyl]-2-methoxyphenoxy}acetamide (13u);
N1-(5,6-difluoro-1,3-benzothiazol-2-yl)-2-{2-methoxy-5-[3-(3,4,5-trimethoxyphenyl)-5-isoxazolyl]-2-methoxyphenoxy}acetamide (13v).

TABLE 1

Showing the amidobenzothiazoles formed by reacting compounds 7(a-v) with compounds 1-6:

| 7(a-v)/1-6 | Comp. No. | | | | | |
|---|---|---|---|---|---|---|
| | 1 | 2 | 3 | 4 | 5 | 6 |
| 7a | 8a | 9a | 10a | 11a | 12a | 13a |
| 7b | 8b | 9b | 10b | 11b | 12b | 13b |
| 7c | 8c | 9c | 10c | 11c | 12c | 13c |
| 7d | 8d | 9d | 10d | 11d | 12d | 13d |
| 7e | 8e | 9e | 10e | 11e | 12e | 13e |
| 7f | 8f | 9f | 10f | 11f | 12f | 13f |
| 7g | 8g | 9g | 10g | 11g | 12g | 13g |
| 7h | 8h | 9h | 10h | 11h | 12h | 13h |
| 7i | 8i | 9i | 10i | 11i | 12i | 13i |
| 7j | 8j | 9j | 10j | 11j | 12j | 13j |
| 7k | 8k | 9k | 10k | 11k | 12k | 13k |
| 7l | 8l | 9l | 10l | 11l | 12l | 13l |
| 7m | 8m | 9m | 10m | 11m | 12m | 13m |
| 7n | 8n | 9n | 10n | 11n | 12n | 13n |
| 7o | 8o | 9o | 10o | 11o | 12o | 13o |
| 7p | 8p | 9p | 10p | 11p | 12p | 13p |
| 7q | 8q | 9q | 10q | 11q | 12q | 13q |
| 7r | 8r | 9r | 10r | 11r | 12r | 13r |
| 7s | 8s | 9s | 10s | 11s | 12s | 13s |
| 7t | 8t | 9t | 10t | 11t | 12t | 13t |
| 7u | 8u | 9u | 10u | 11u | 12u | 13u |
| 7v | 8v | 9v | 10v | 11v | 12v | 13v |

In yet another embodiment of the present invention, structural formulas of the representative compounds 8-13 (a-v) are:

8a 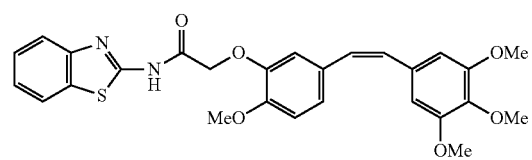
8b 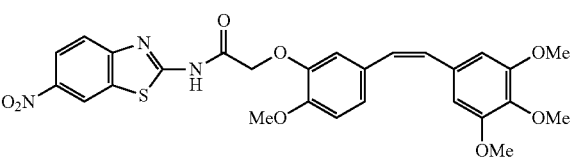
8c 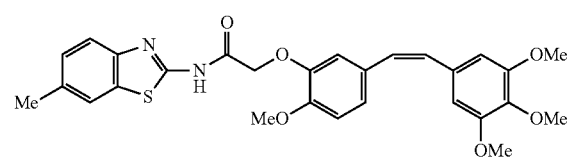
8d 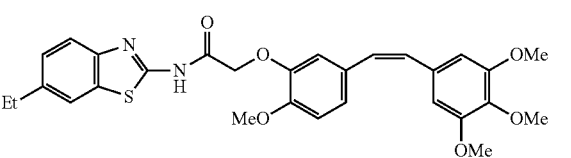
8e 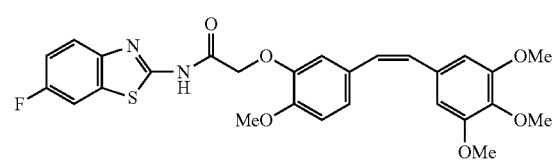
8f 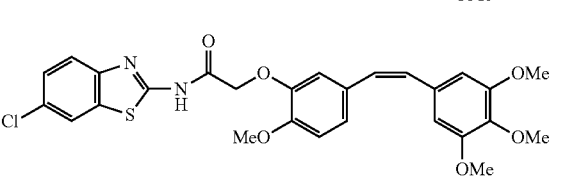
8g 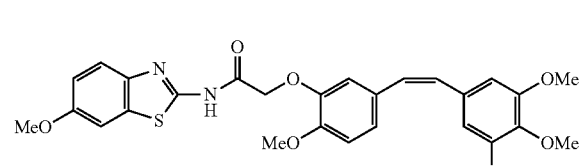
8h 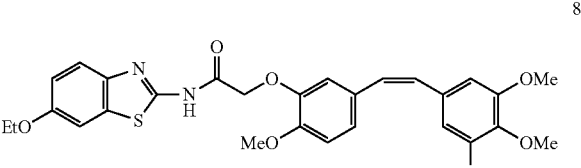
8i 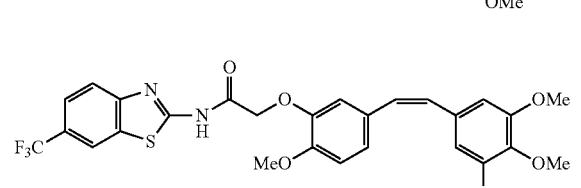
8j 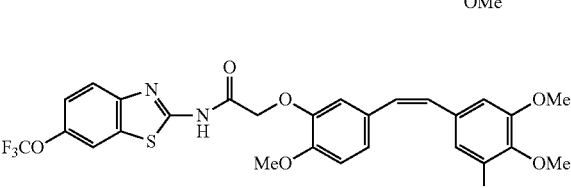
8k 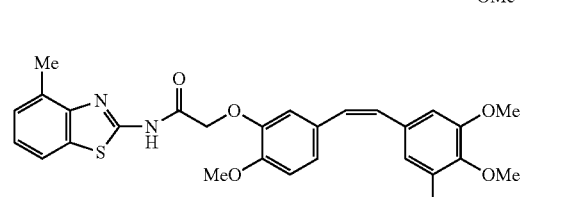
8l 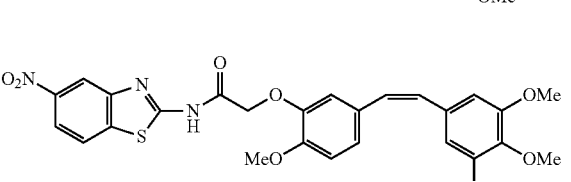
8m 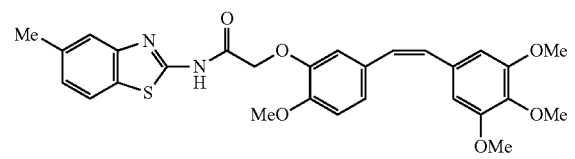
8n 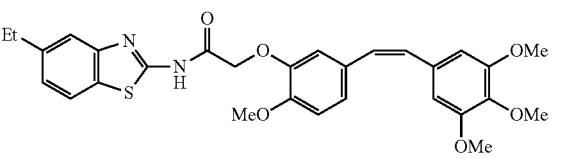
8o 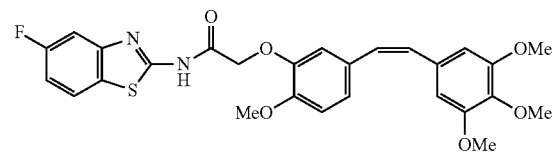
8p 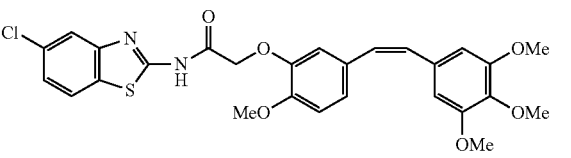
8q 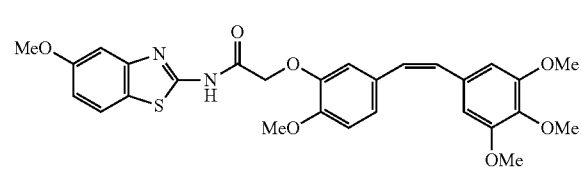
8r 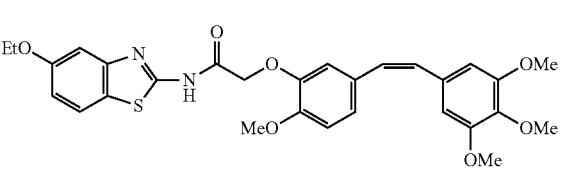

-continued
8s
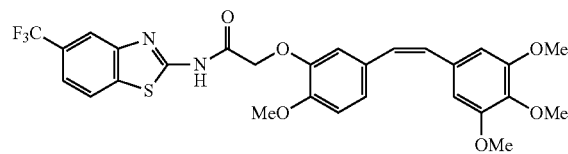
8t
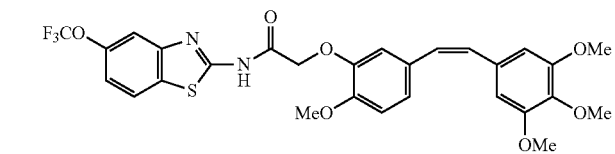
8u
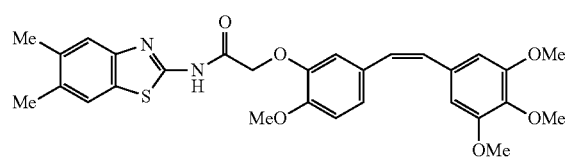
8v
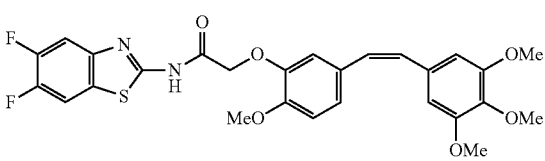
9a
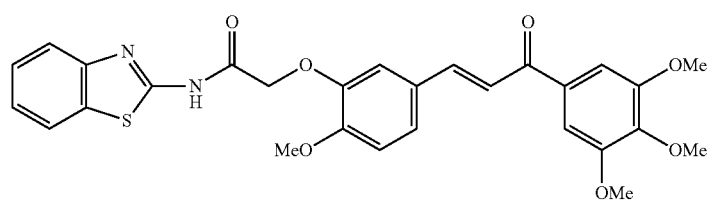
9b
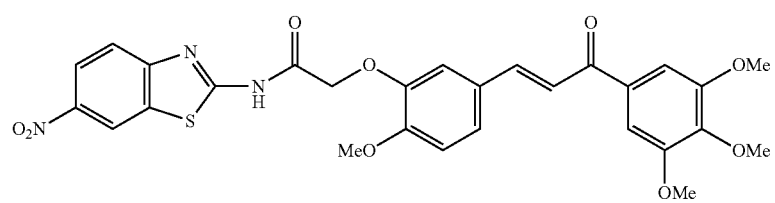
9c
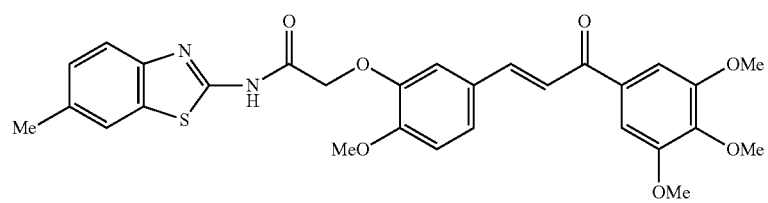
9d
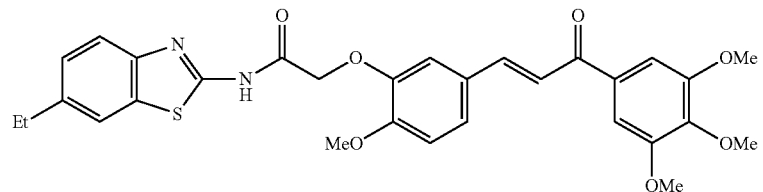
9e
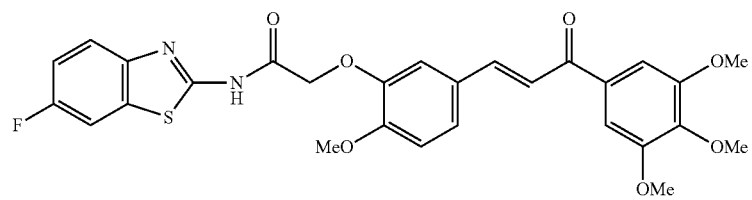
9f
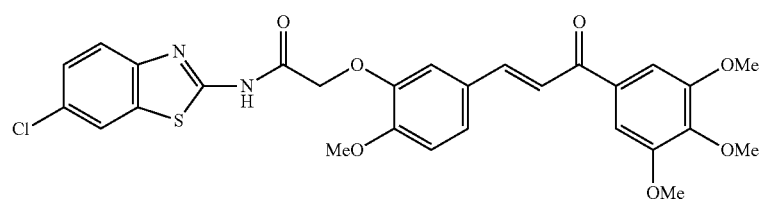

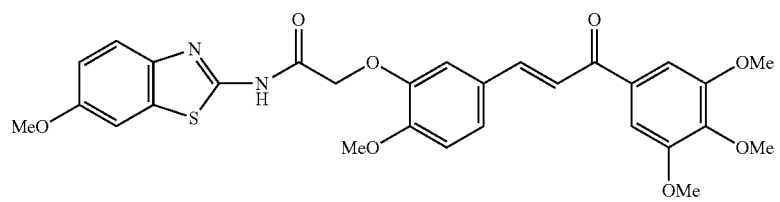
9g
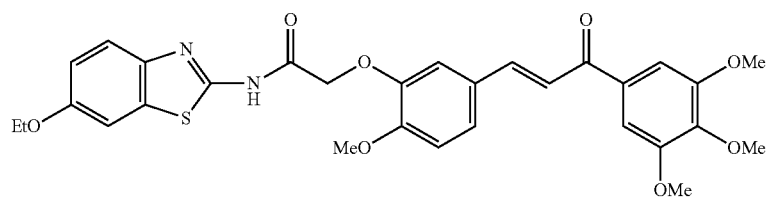
9h
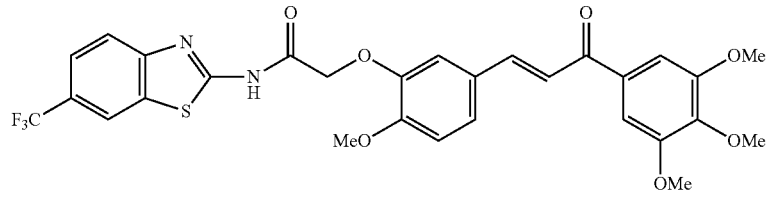
9i
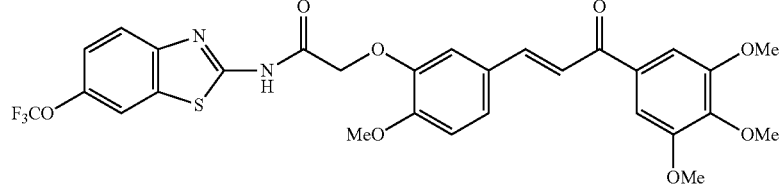
9j
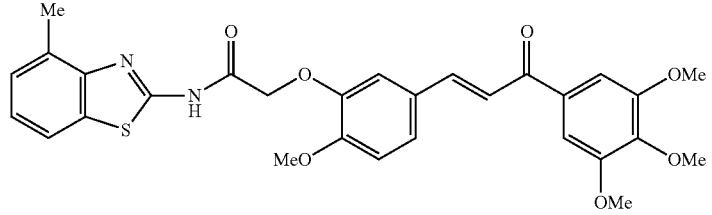
9k
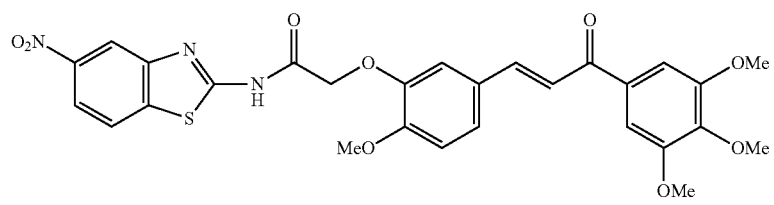
9l
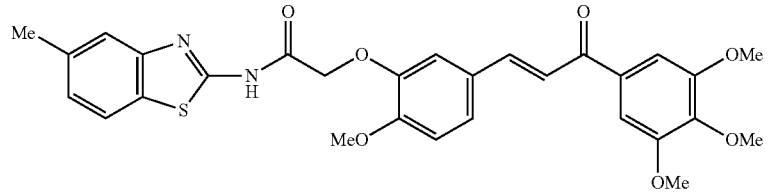
9m
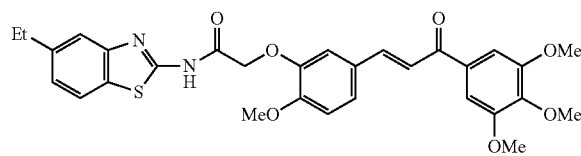
9n
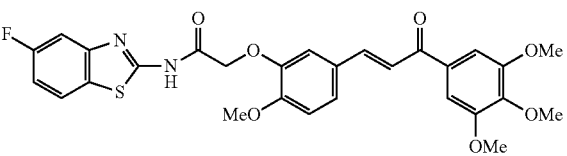
9o -continued
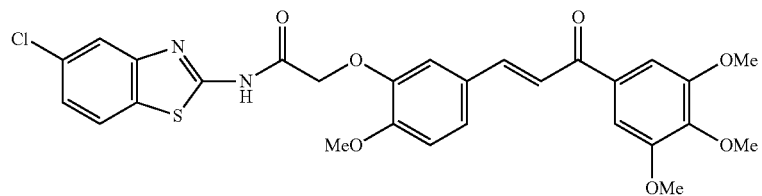 9p
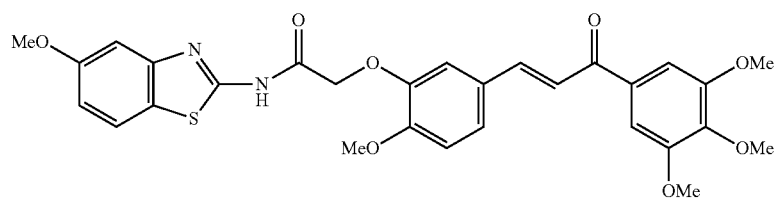 9q
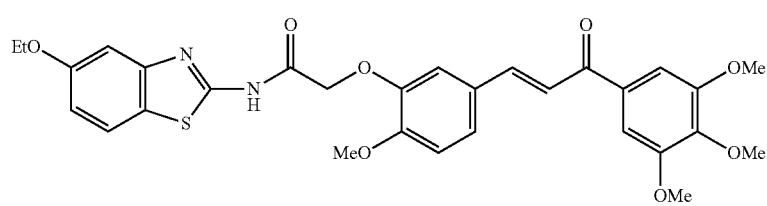 9r
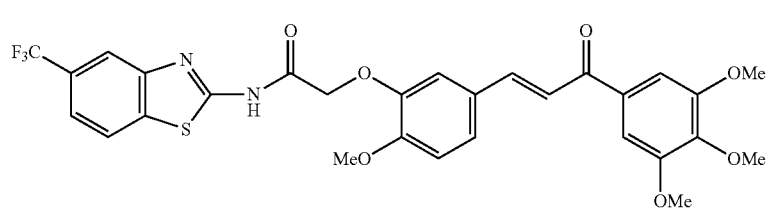 9s
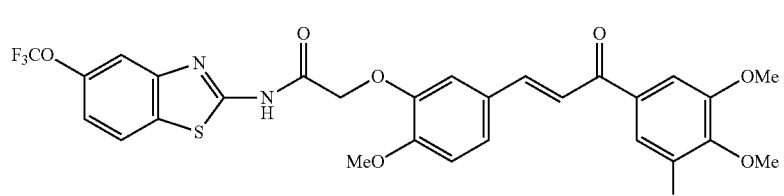 9t
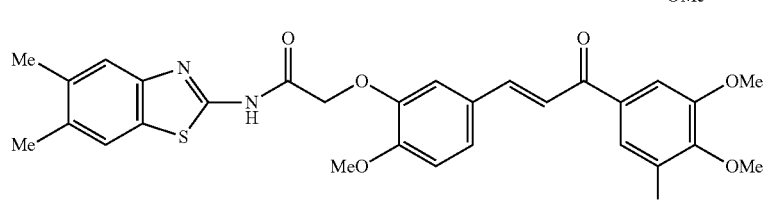 9u
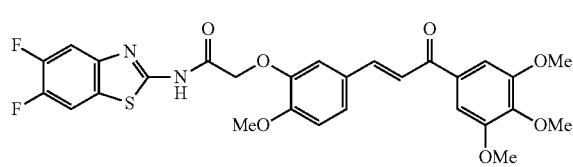 9v
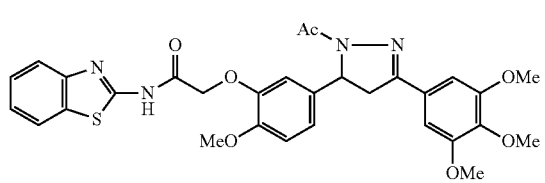 10a
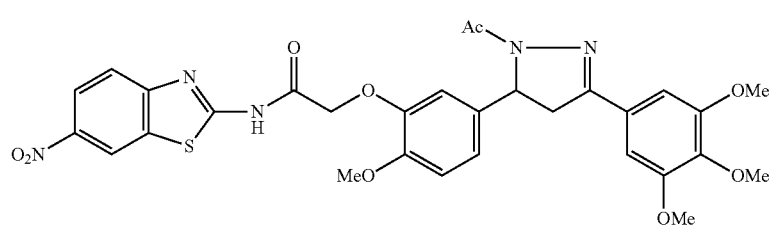 10b -continued
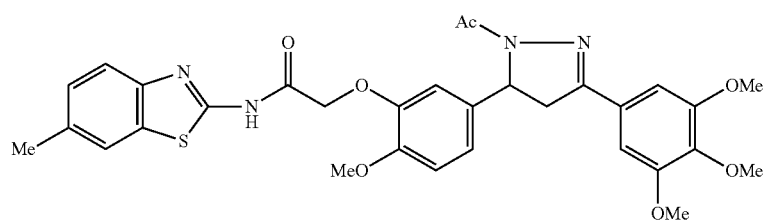
10c
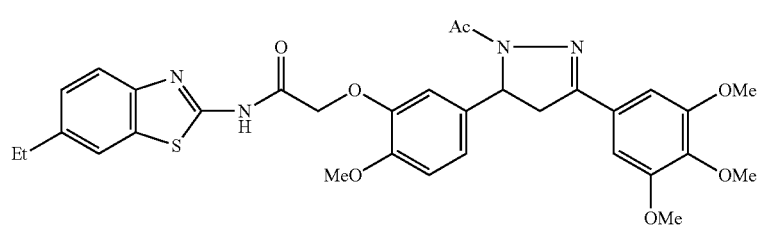
10d
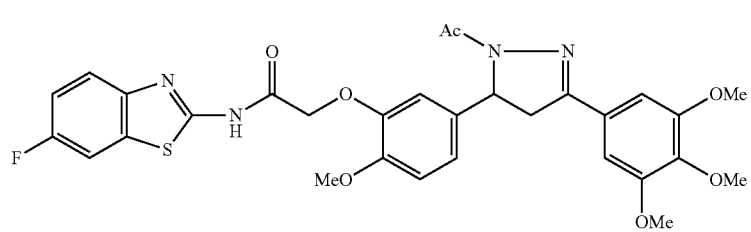
10e
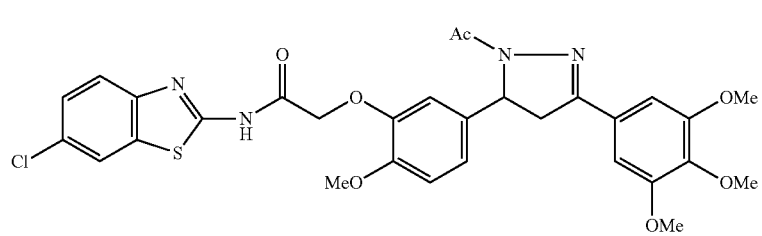
10f
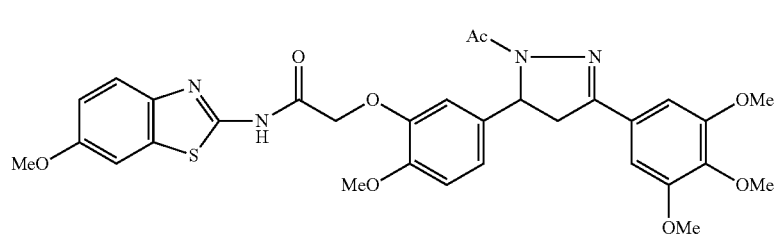
10g
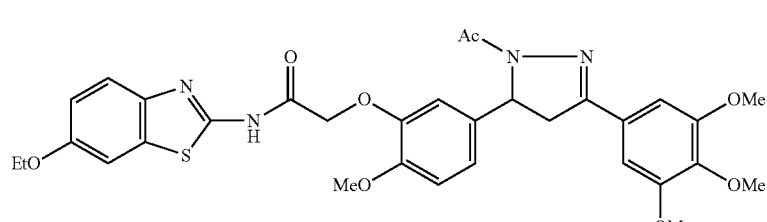
10h
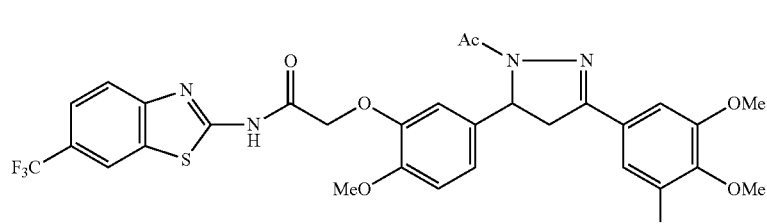
10i -continued
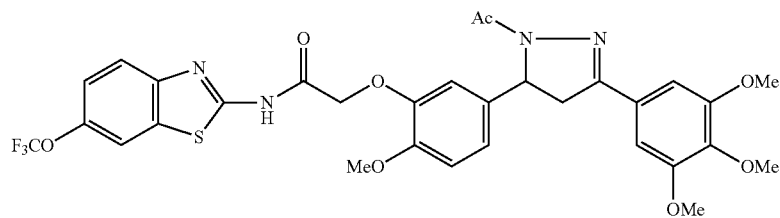
10j
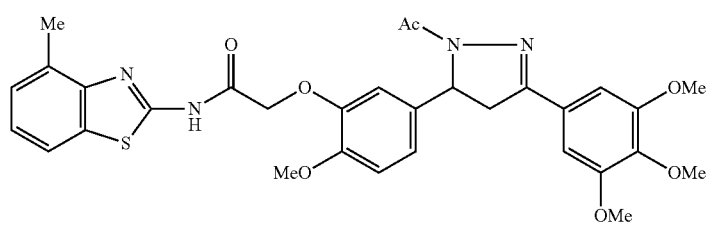
10k
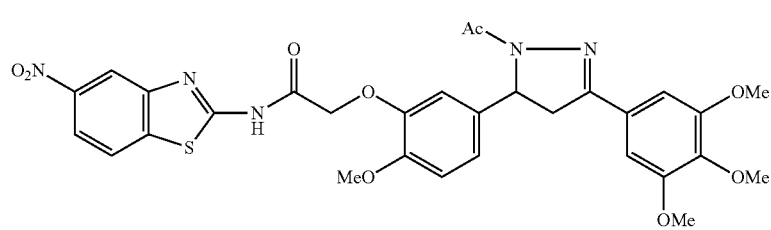
10l
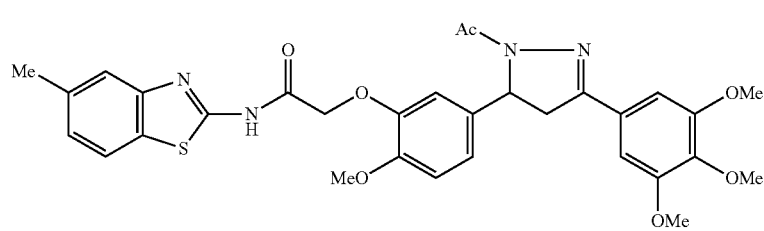
10m
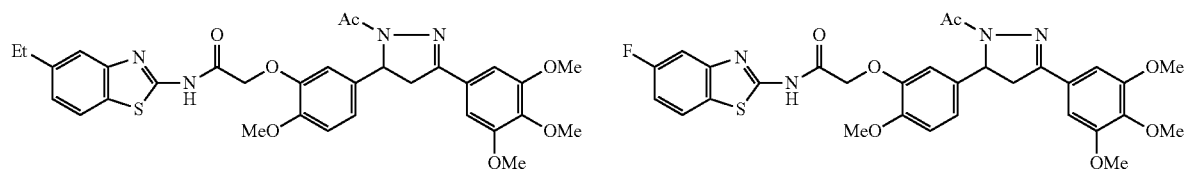
10n 10o
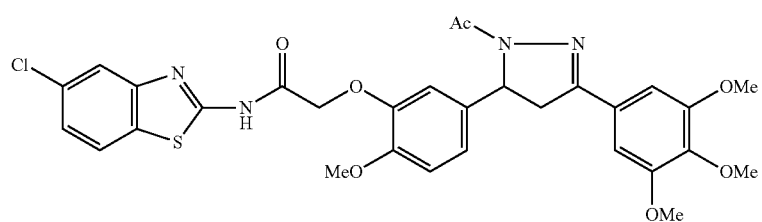
10p
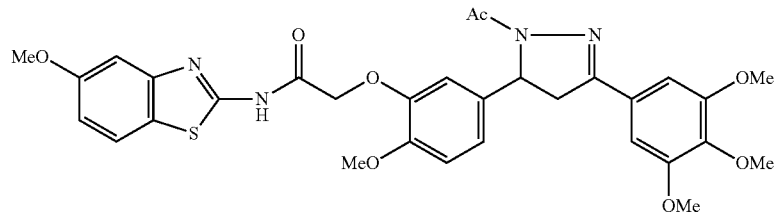
10q -continued
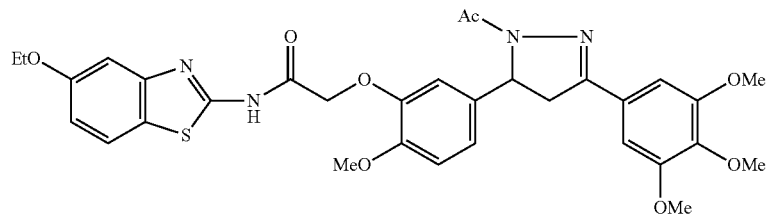
10r
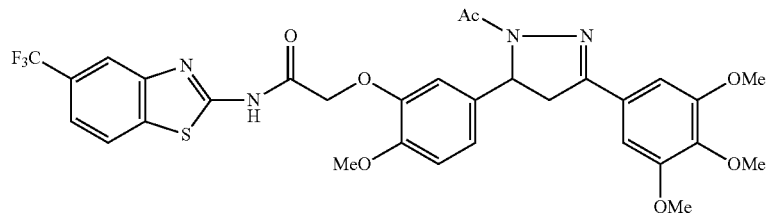
10s
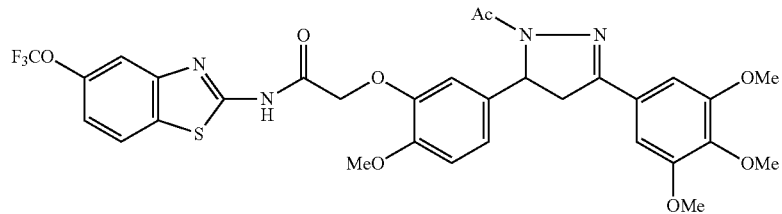
10t
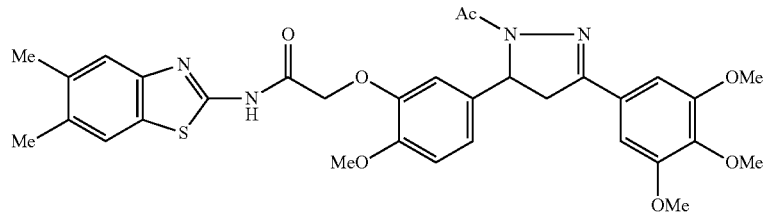
10u
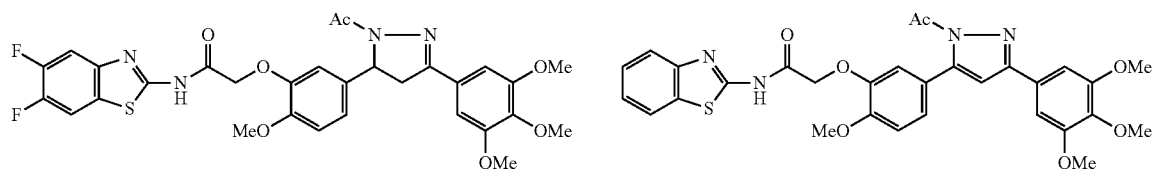
10v          11a
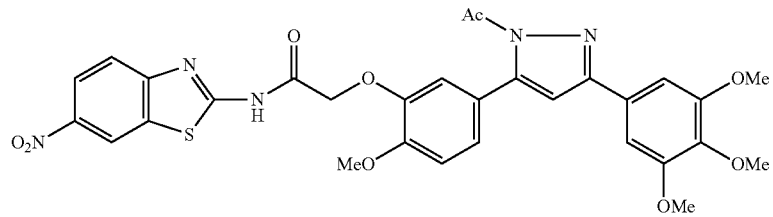
11b
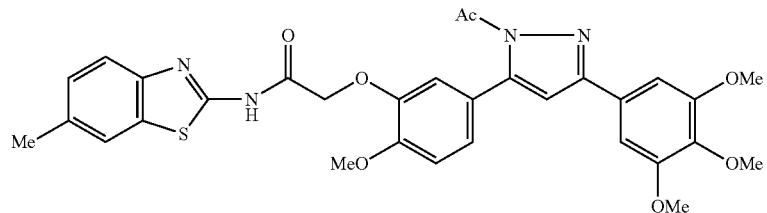
11c -continued
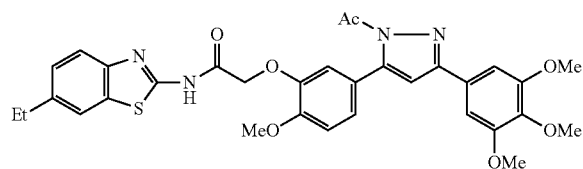
11d
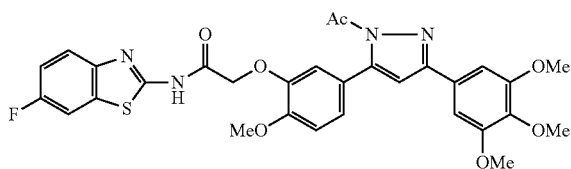
11e
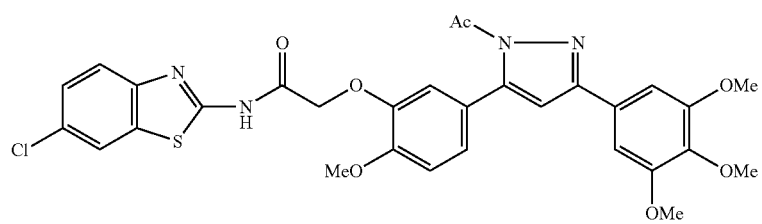
11f
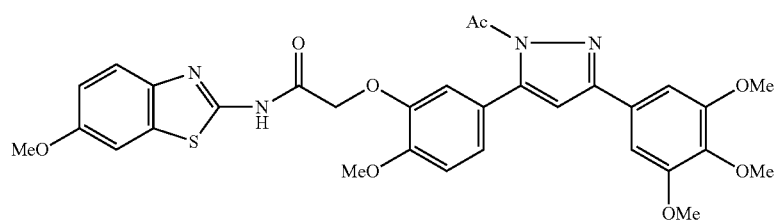
11g
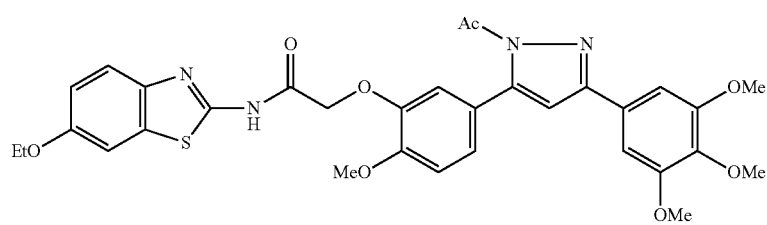
11h
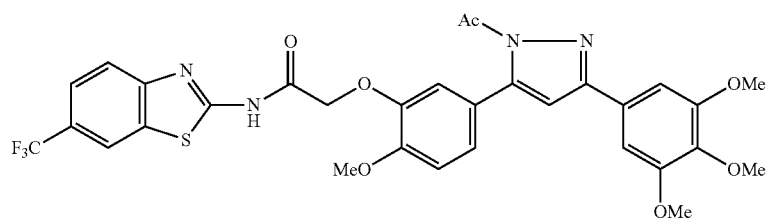
11i
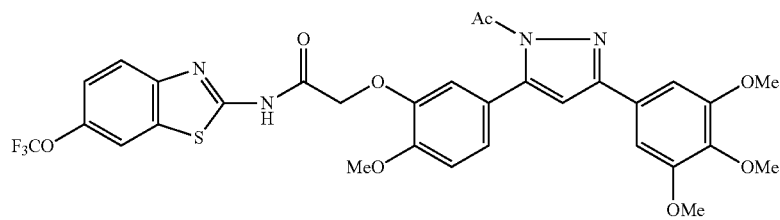
11j
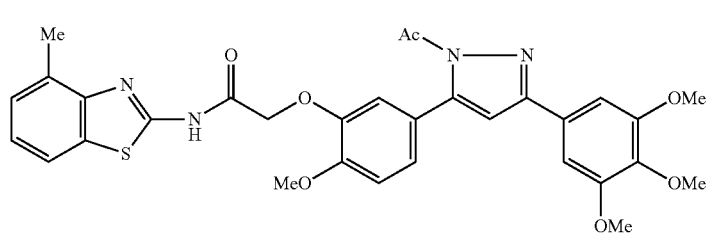
11k -continued
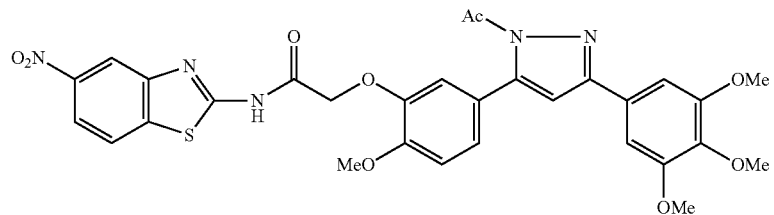
11l
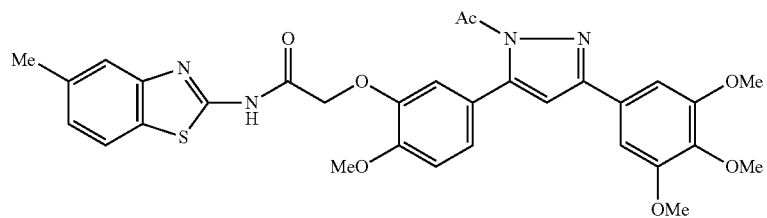
11m
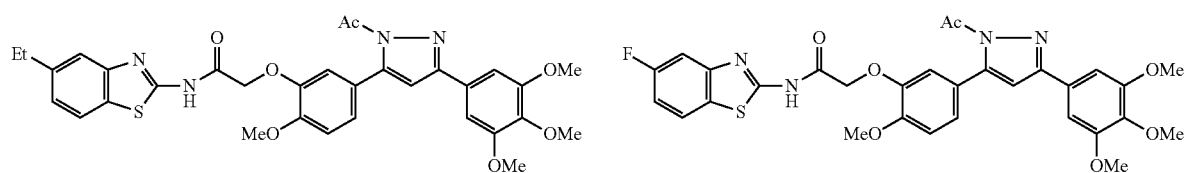
11n  11o
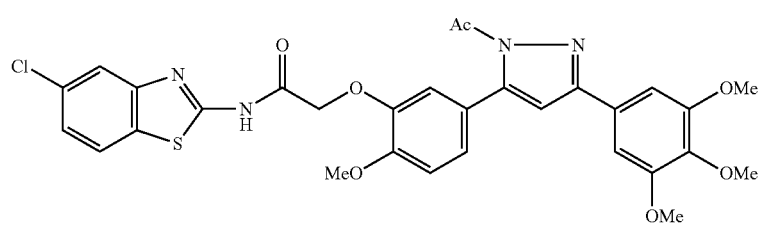
11p
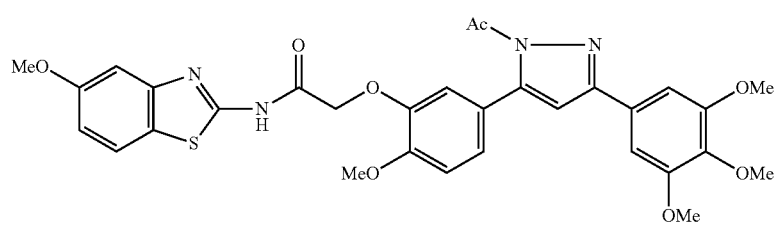
11q
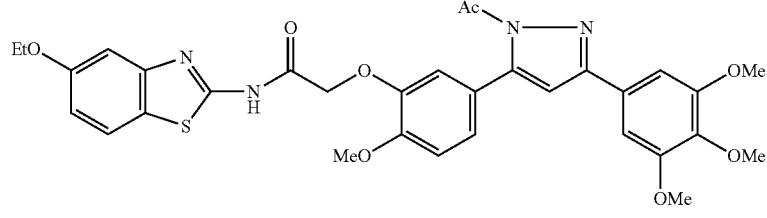
11r
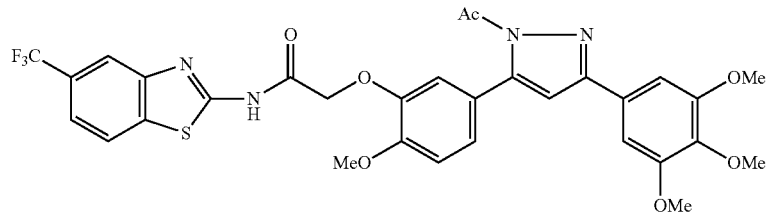
11s -continued
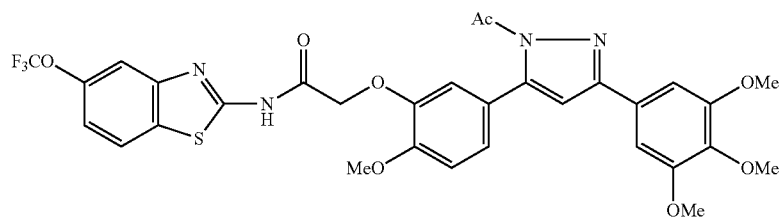
11t
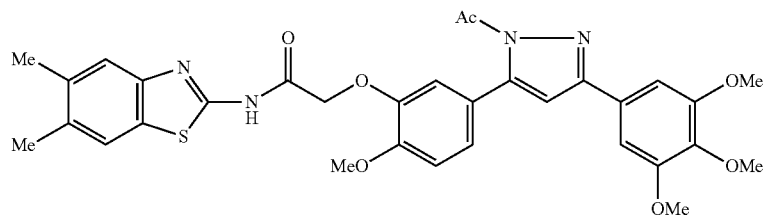
11u
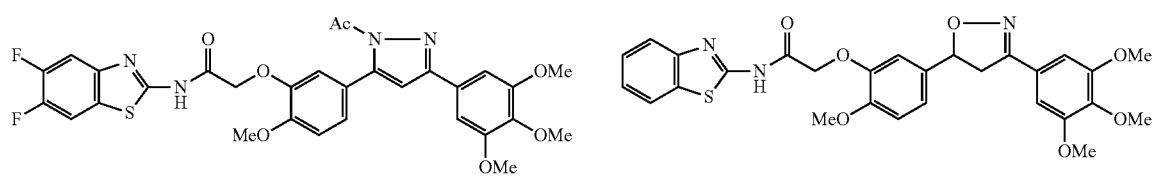
11v
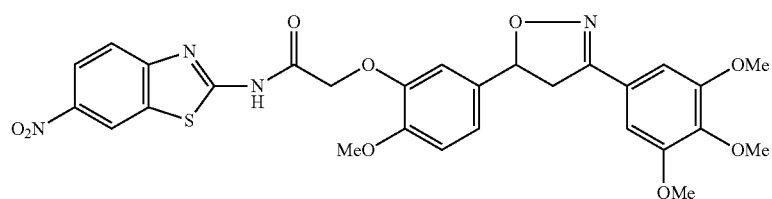
12a
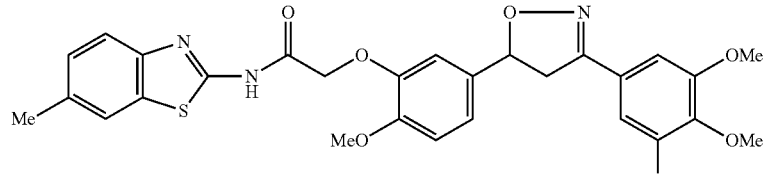
12b
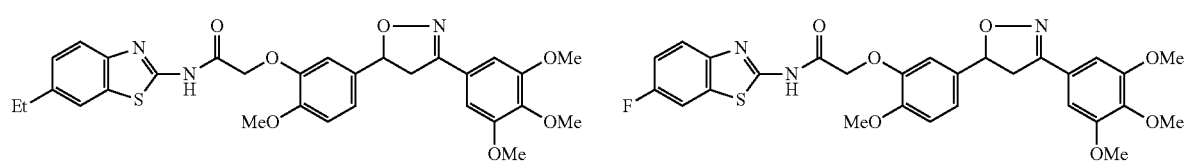
12c
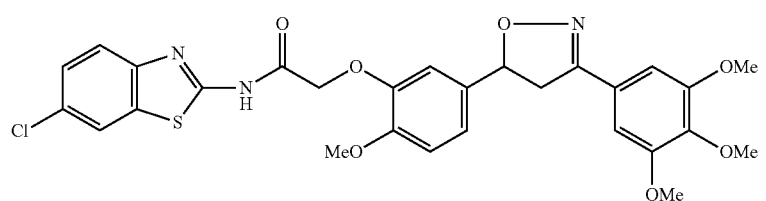
12d
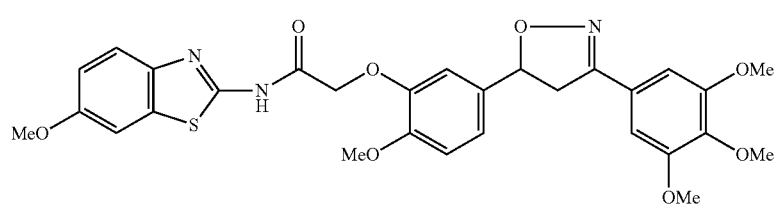
12e
12f
12g -continued
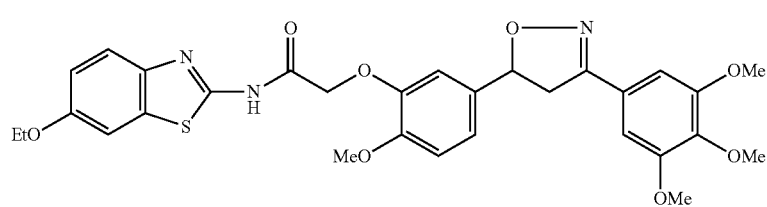
12h
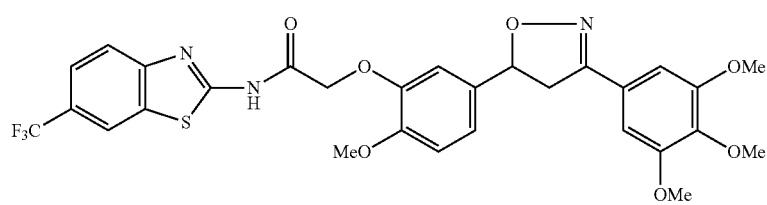
12i
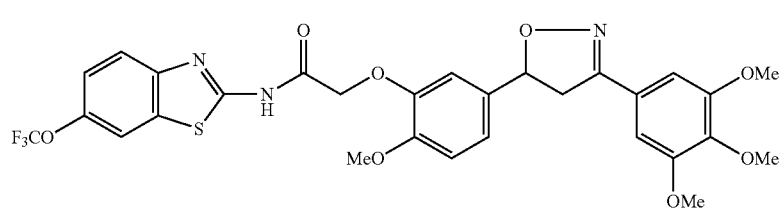
12j
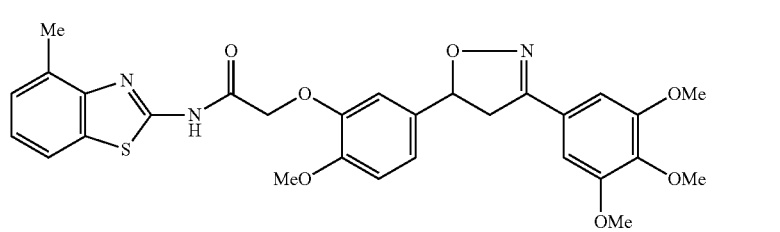
12k
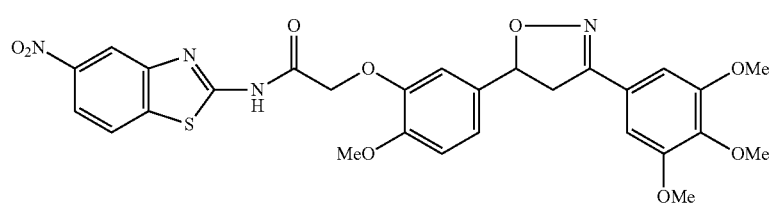
12l
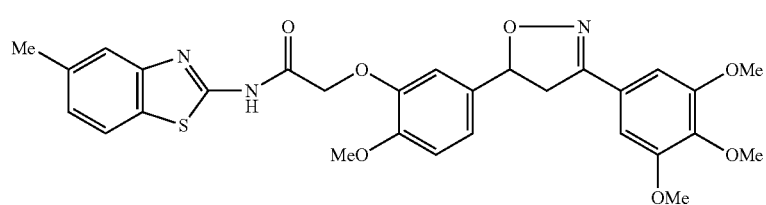
12m
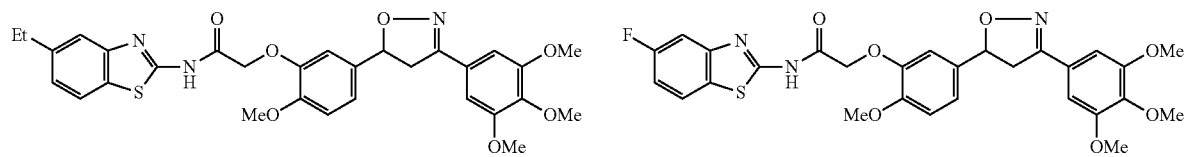
12n    12o
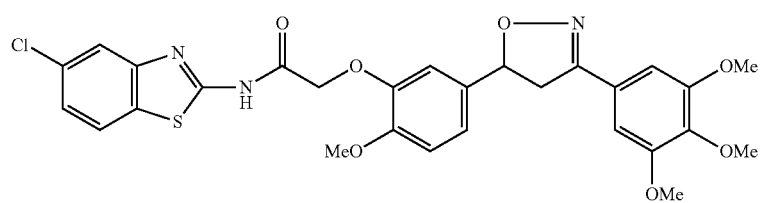
12p -continued
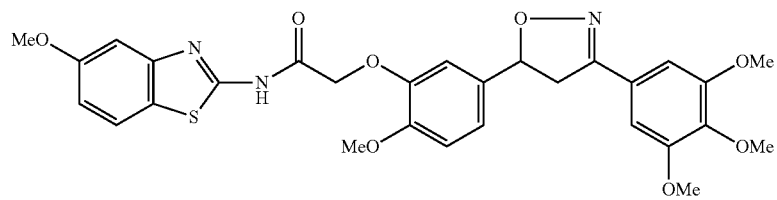
12q
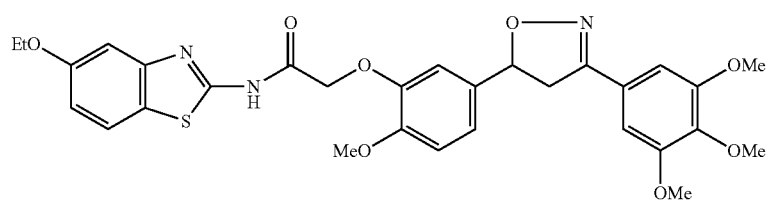
12r
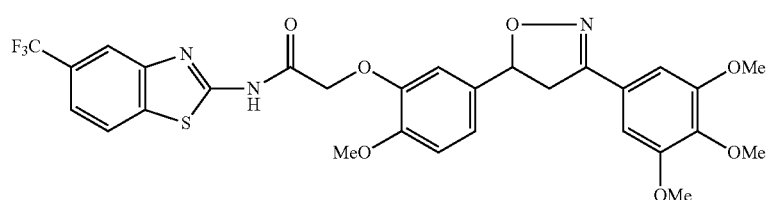
12s
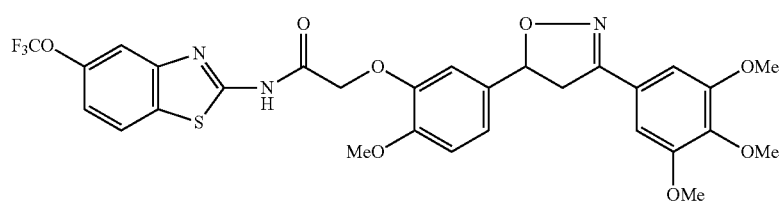
12t
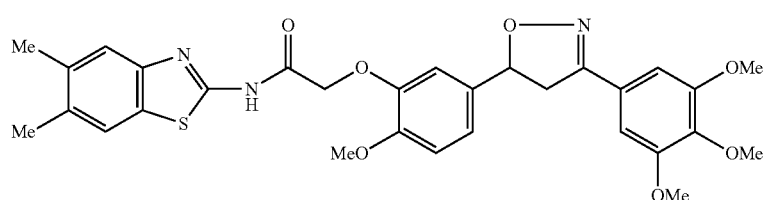
12u
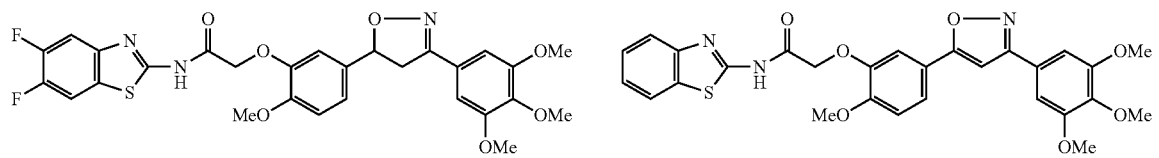
12v 13a
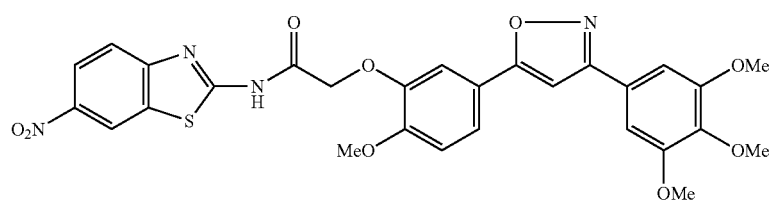
13b
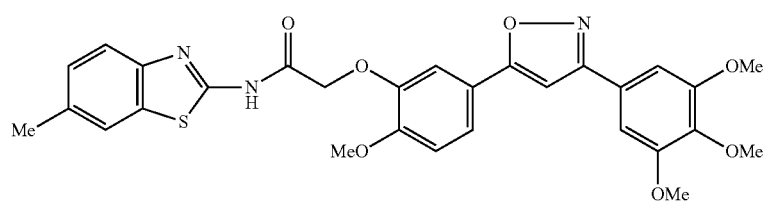
13c -continued
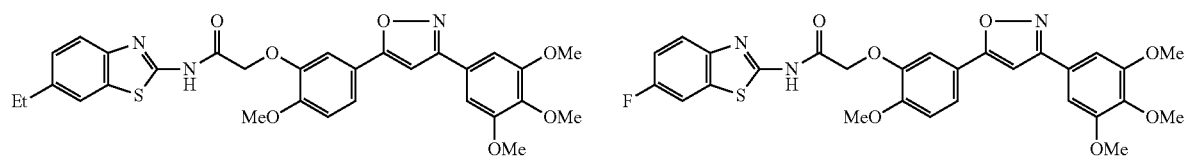
13d
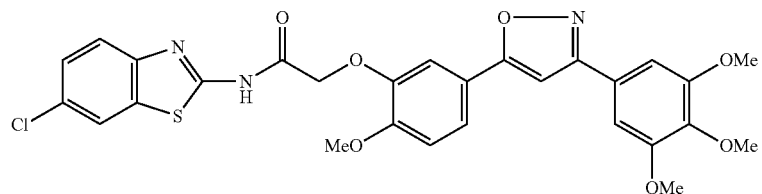
13e
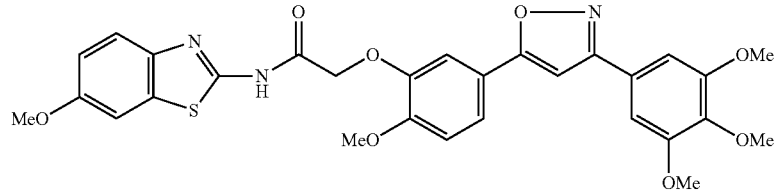
13f
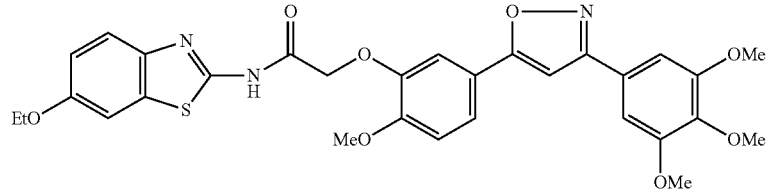
13g
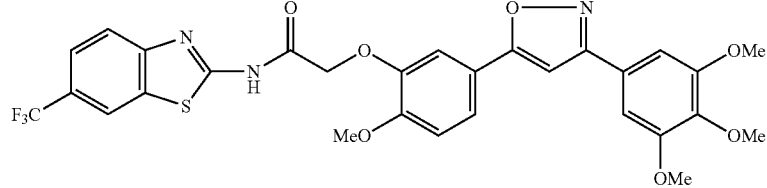
13h
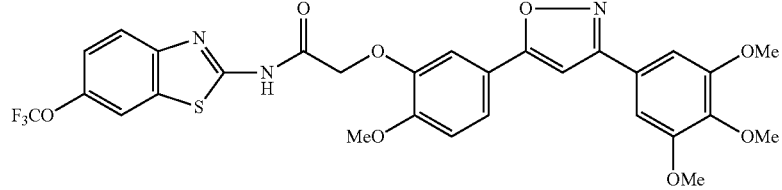
13i
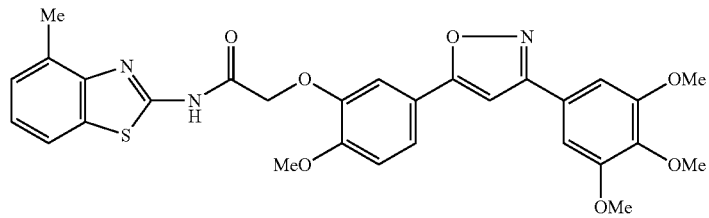
13j
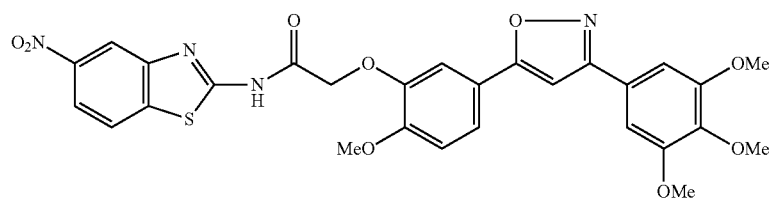
13k
13l -continued
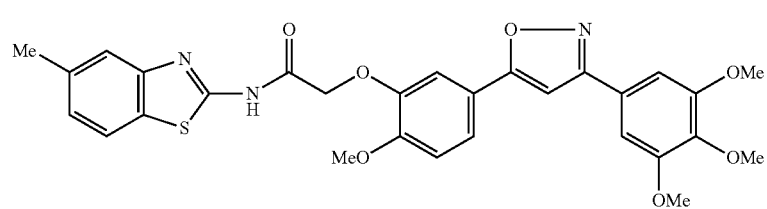
13m
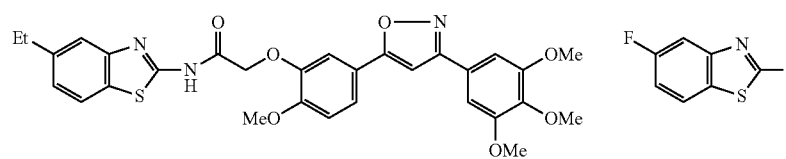
13n
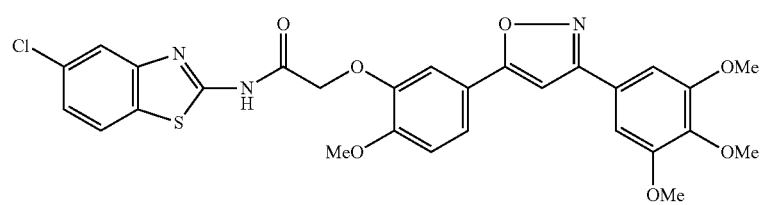
13o
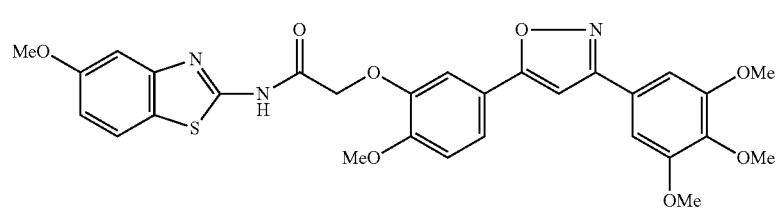
13p
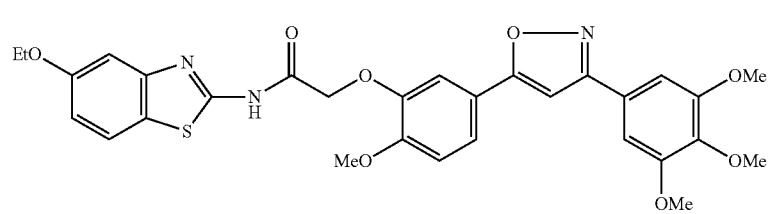
13q
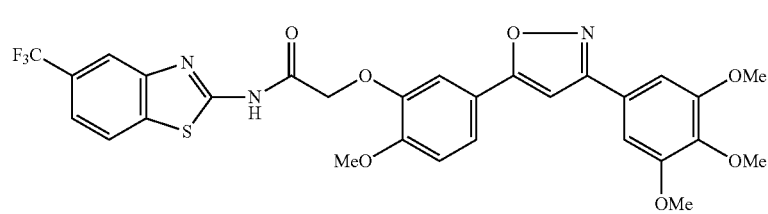
13r
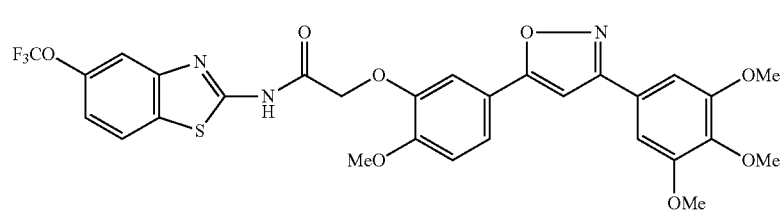
13s
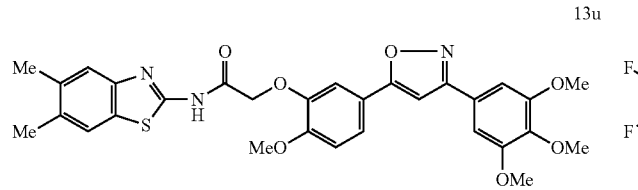
13t
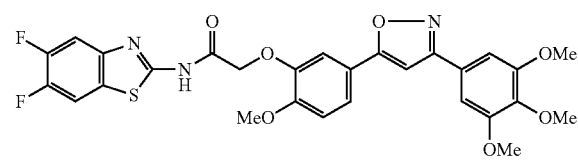
13u
13v In yet another embodiment of the present invention, said compounds are useful as anti-cancer agents.

In yet another embodiment of the present invention, said compounds exhibit an in vitro anticancer activity against human cancer cell lines selected from the group consisting of leukemia cancer cell lines, non-small cell lung cancer cell lines, colon cancer cell lines, CNS cancer cell lines, melanoma cancer cell lines, ovarian cancer cell lines, renal cancer cell lines, prostate cancer cell lines and breast cancer cell lines.

In yet another embodiment of the present invention, process for the preparation of amidobenzothiazole of general formula A comprising the steps of:

i. reacting 2-aminobenzothiazoles of formula 7a-v with a compound selected from formulae 1, 2, 3, 4, 5 and 6 in an organic solvent in the presence of EDC (1-Ethyl-3-(3-Dimethylaminopropyl)carbodiimide) and 1-hydroxy-1,2,3-benzotriazole(HOBt) at a temperature in the range of 25 to 30° C. for a period in the range of 22 to 24 hrs;

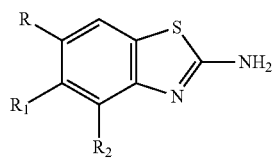

7a-v

7a: R = R$_1$ = R$_2$ = H,
7b: R = NO$_2$, R$_1$ = R$_2$ = H,
7c: R = CH$_3$, R$_1$ = R$_2$ = H,
7d: R = C$_2$H$_5$, R$_1$ = R$_2$ = H,
7e: R = F, R$_1$ = R$_2$ = H,
7f: R = Cl, R$_1$ = R$_2$ = H,
7g: R = OCH$_3$, R$_1$ = R$_2$ = H,
7h: R = OC$_2$H$_5$, R$_1$ = R$_2$ = H,
7i: R = CF$_3$, R$_1$ = R$_2$ = H,
7j: R = OCF$_3$, R$_1$ = R$_2$ = H,
7k: R$_2$ = CH$_3$, R$_1$ = R = H,

7l: R$_1$ = NO$_2$, R = R$_2$ = H,
7m: R$_1$ = CH$_3$, R = R$_2$ = H,
7n: R$_1$ = C$_2$H$_5$, R = R$_2$ = H,
7o: R$_1$ = F, R = R$_2$ = H,
7p: R$_1$ = Cl, R = R$_2$ = H.
7q: R$_1$ = OCH$_3$, R = R$_2$ = H,
7r: R$_1$ = OC$_2$H$_5$, R = R$_2$ = H,
7s: R$_1$ = CF$_3$, R = R$_2$ = H,
7t: R$_1$ = OCF$_3$ R = R$_2$ = H,
7u: R$_2$ = H, R = R$_2$ = CH$_3$,
7v: R$_2$ = H, R = R$_1$ = F,

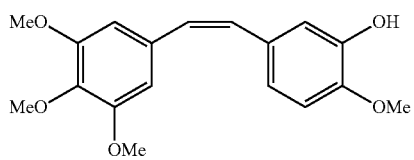

1

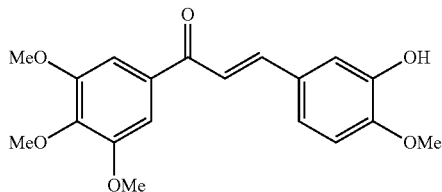

2

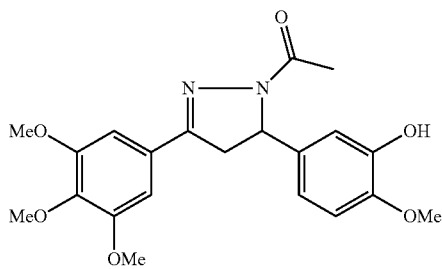

3

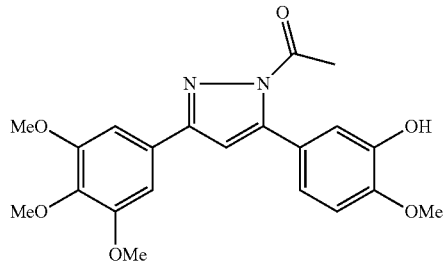

4

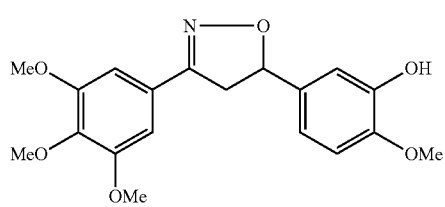

5

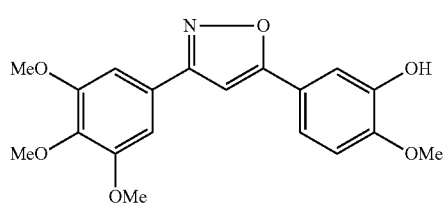

6 ii. adding water in the mixture as obtained in step (i) and extracting with organic solvent and evaporating the organic solvent to obtain the resultant crude product;

iii. purifying crude product as obtained in step (ii) by column chromatography to obtain the desired products of formulae 8a-v, 9a-v, 10a-v, 11a-v, 12a-v and 13a-v.

In yet another embodiment of the present invention, organic solvent used is selected from the group consisting of dichloromethane, chloroform or N,N-dimethylformamide.

In yet another embodiment of the present invention, GI50 values of the compounds (8a, 8e, 8g, 8i, 8j, 9a, 9e, 9g, 9i, 9j and 10i) used for in vitro activity against leukemia cancer cell lines is in the range of 0.037 to 29.9 μM.

In yet another embodiment of the present invention, GI50 values of the compounds (8a, 8e, 8a, 8i, 8j, 9a, 9e, 9g, 9i, 9j and 10i) used for in vitro activity against non small cell lung cancer cell lines is in the range of 0.038 to 50.3 μM.

In yet another embodiment of the present invention, GI50 values of the compounds (8a, 8e, 8g, 8i, 8j, 9a, 9e, 9g, 9i, 9j and 10i) used for in vitro activity against colon cancer cell lines is in the range of 0.046 to 94.8 μM.

In yet another embodiment of the present invention, GI50 values of the compounds (8a, 8e, 8g, 8i, 8j, 9a, 9e, 9g, 9i, 9j and 10i) used for in vitro activity against CNS cancer cell lines is in the range of 0.045 to 18.8 μM.

In yet another embodiment of the present invention, GI50 values of the compounds (8a, 8e, 8a, 8i, 8j, 9a, 9e, 9g, 9i, 9j and 10i) used for in vitro activity against melanoma cancer cell lines is in the range of 0.019 to 89.2 μM.

In yet another embodiment of the present invention, GI50 values of the compounds (8a, 8e, 8g, 8i, 8j, 9a, 9e, 9g; 9i, 9j and 10i) used for in vitro activity against ovarian cancer cell lines is in the range of 0.033 to 91.6 μM.

In yet another embodiment of the present invention, GI50 values of the compounds (8a, 8e, 8g, 8i, 8j, 9a, 9e, 9g, 9i, 9j and 10i) used for in vitro activity against renal cancer cell lines is in the range of 0.05 to 100 μM.

In yet another embodiment of the present invention, GI50 values of the compounds (8a, 8e, 8g, 8i, 8j, 9a, 9e, 9g, 9i, 9j and 10i) used for in vitro activity against prostate cancer cell lines is in the range of 0.18 to 22.9 μM.

In yet another embodiment of the present invention, GI50 values of the compounds (8a, 8e, 8g, 8i, 8j, 9a, 9e, 9a, 9i, 9j and 10i) used for in vitro activity against breast cancer cell lines is in the range of 0.051 to 58.5 μM.

DETAILED DESCRIPTION OF THE INVENTION

Figure 1:
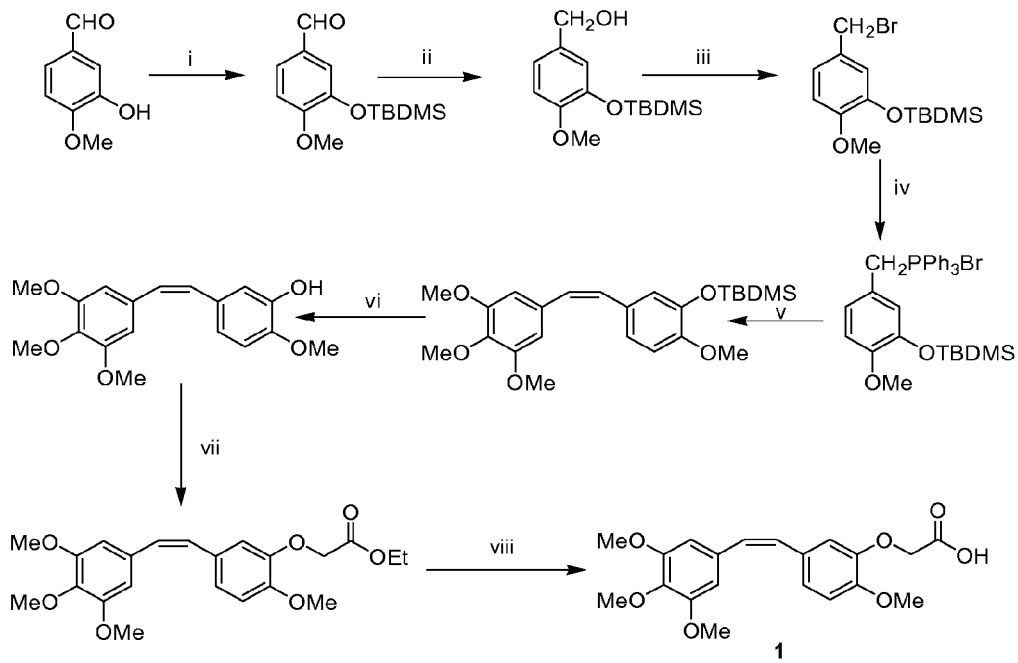
FIG. 1 represents the flow diagram for the preparation of compound 1. Wherein reagent and conditions are i) TBDMS-Cl, TEA, DMF; ii) NaBH$_4$, MeOH; iii) LiBr, THF; iv) PPH$_3$, toluene; v) n-BuLi, THF, −20° C., trimethoxy benzaldehyde; vi) TBAF, THF; vii) 2-bromoethyl acetate, K$_2$CO$_3$, DMF; viii) LiOH, THF, H$_2$O
Figure 2:
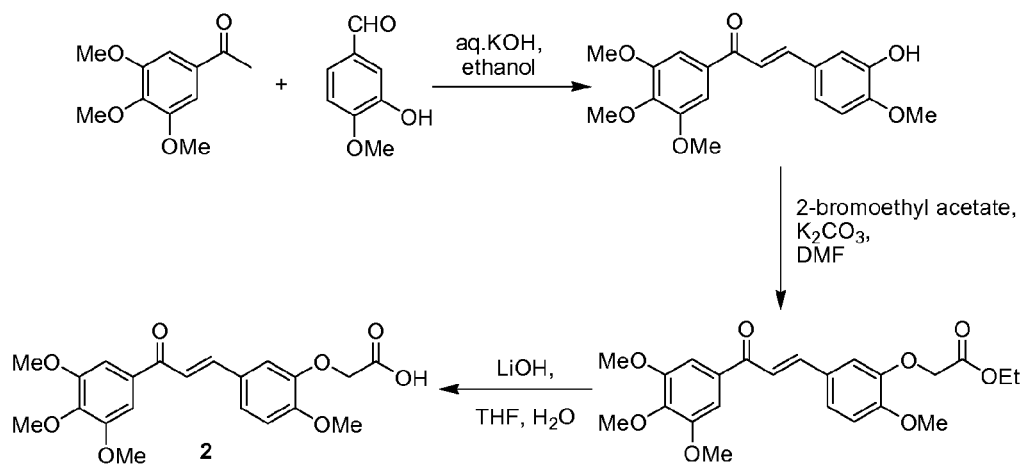
FIG. 2 represents the flow diagram for the preparation of compound 2.
Figure 3:
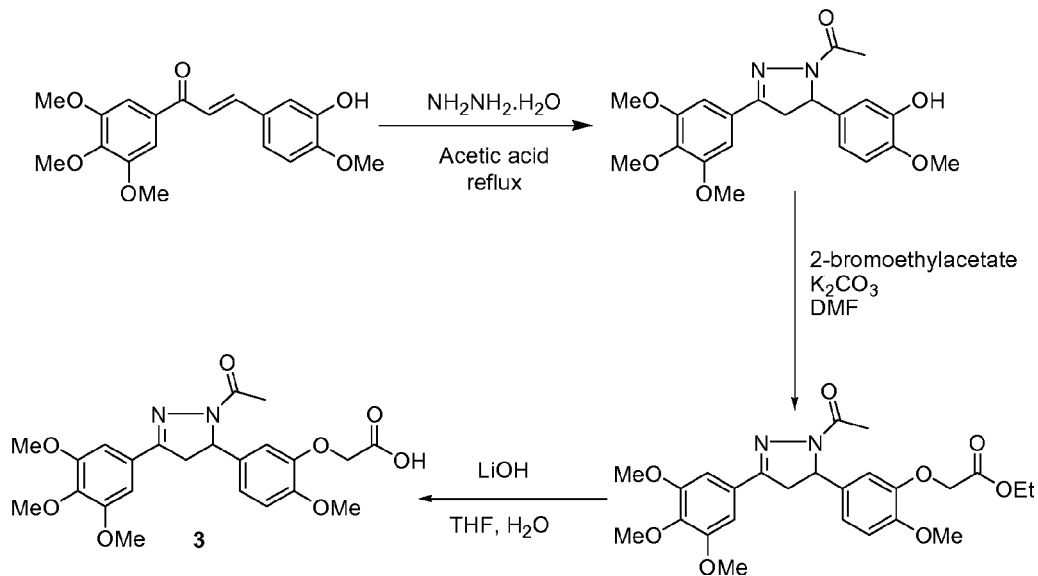
FIG. 3 represents the flow diagram for the preparation of compound 3.
Figure 4:
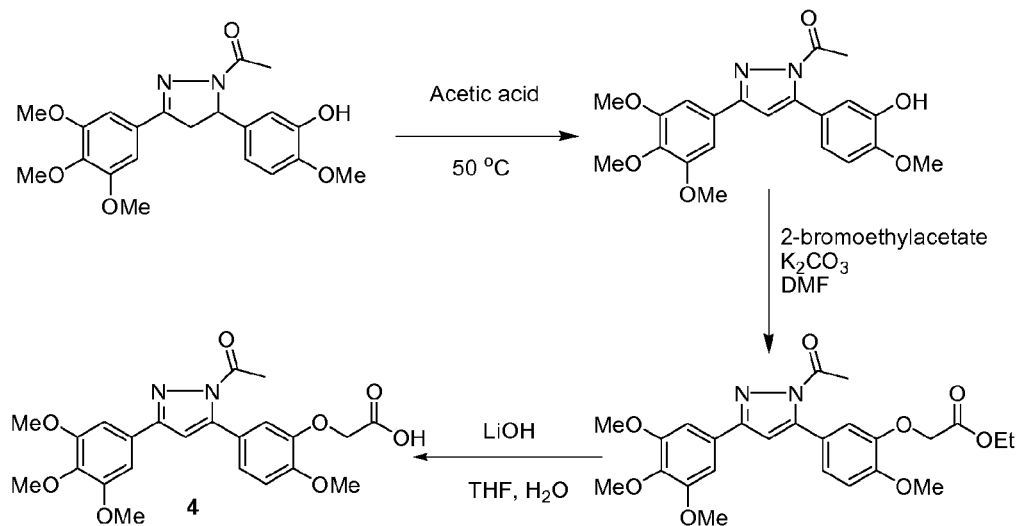
FIG. 4 represents the flow diagram for the preparation of compound 4.
Figure 5:
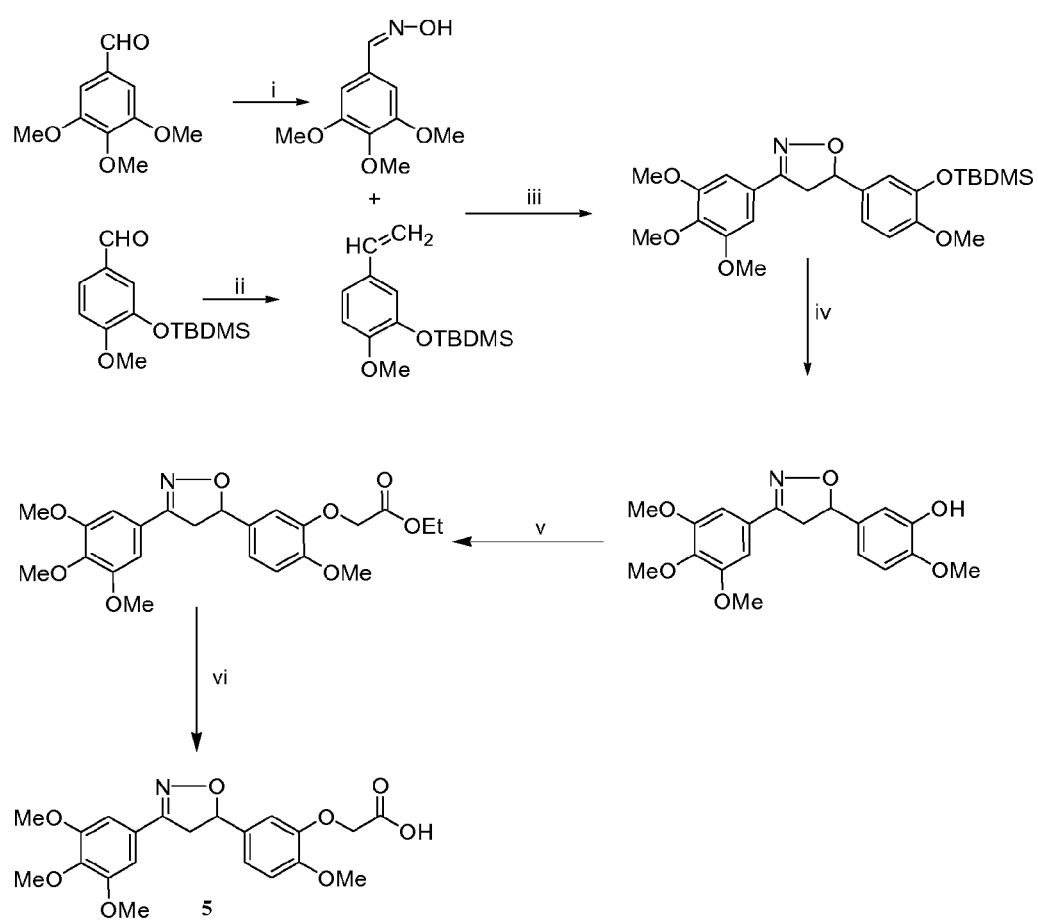
FIG. 5 represents the flow diagram for the preparation of compound 5. Wherein reagent and conditions are i) NH$_2$OH.HCl, NaHCO$_3$, H$_2$O ii) CH$_3$P(Ph)$_3$$^+$Br$^-$, KOtBu, THF; iii) NaOCl, Et$_3$N, DCM; iv) TBAF, THF; v) 2-bromoethyl acetate, K$_2$CO$_3$, DMF; vi) THF, H$_2$O.
Figure 6:
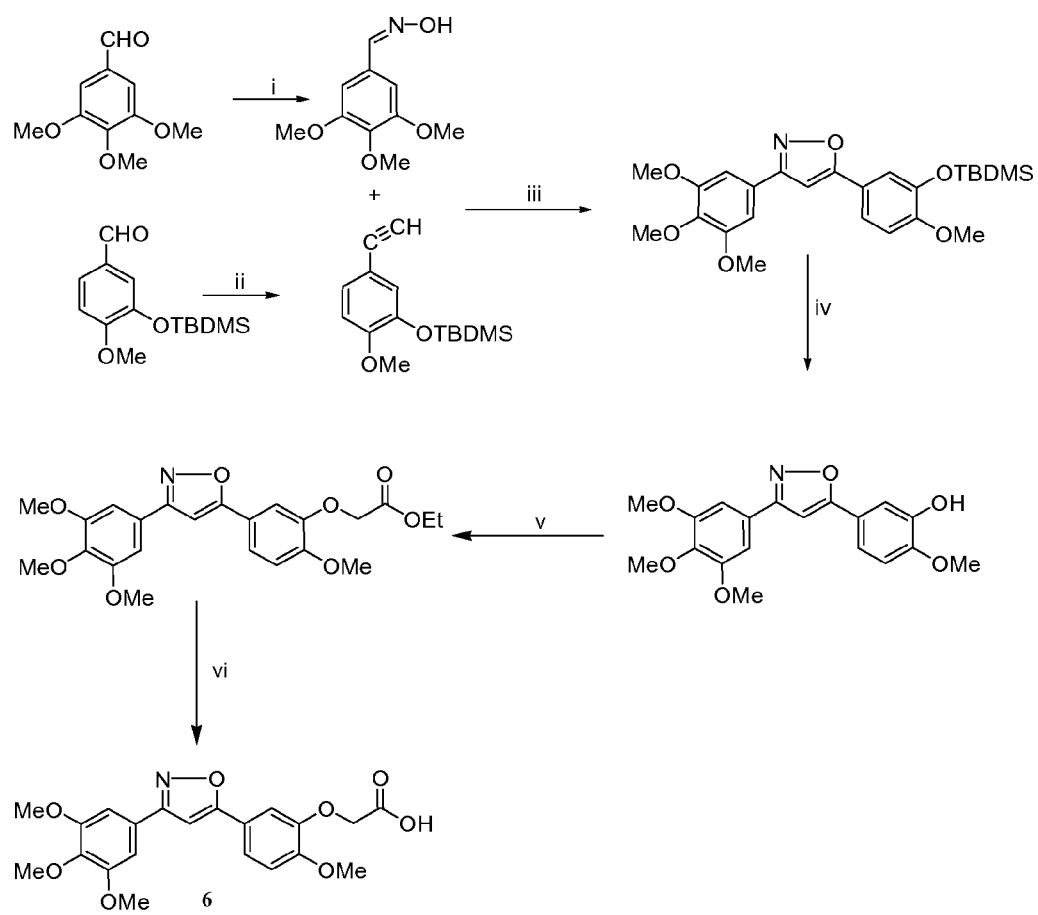
FIG. 6 represents the flow diagram for the preparation of compound 6. Wherein reagent and conditions are i) NH$_2$OH.HCl, NaHCO$_3$, CH$_3$OH, H$_2$O ii) CBr$_4$, PPh$_3$, DCM; iii) n-BuLi, THF, −78° C.; iii) NaOCl, Et$_3$N, DCM; iv) TBAF, THF; v) 2-bromoethyl acetate, K$_2$CO$_3$, DMF; vi) LiOH, THF, H$_2$O.
Figure 7:
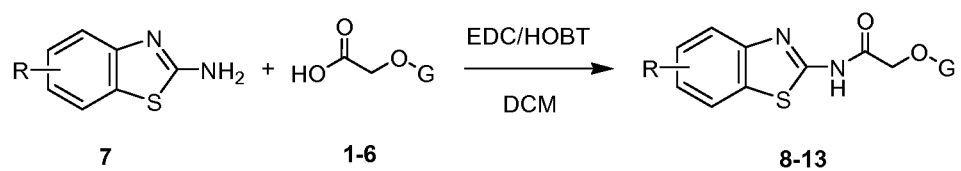
FIG. 7 represents the flow diagram for the preparation of compound 8-13(a-v).
Figure 7:
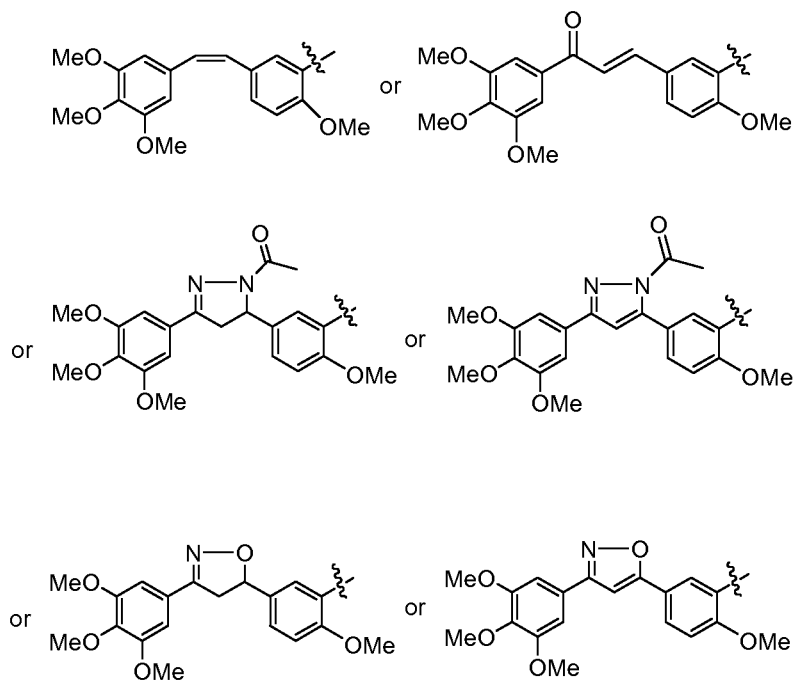

The precursors 2-aminobenzothiazoles of formula 7a-v are commercially available and the precursors combretastatin, chalcone, pyrazoline, pyrazole, isoxazoline and isoxazole of formulae 1, 2, 3, 4, 5 and 6 have been prepared using literature methods or as shown in schemes (Sylvie Ducki, David Rennison, Meiko Woo, Alexander Kendall, Jérémie Fournier Dit Chabert, Alan T. McGown, Nicholas J. Lawrence. *Bioorg. Med. Chem*, Vol 17, 22, 2009, 7698-7710; Regan LeBlanc, John Dickson, Toni Brown, Michelle Stewart, Hari N. Pati, Don VanDerveer, Hadi Arman, Jeff Harris, William Pennington, Herman L. Holt Jr., Moses Lee. *Bioorg. Med. Chem*, Volume 13, 21, 2005, 6025-6034; Marlie Johnson, Brent Younglove, Lauren Lee, Regan LeBlanc, Herman Holt Jr., Patrice Hills, Hilary Mackay, Toni Brown, Susan L. Mooberry, Moses Lee. *Bioorg. Med. Chem Lett*, Vol 17, 21, 2007, 5897-5901; B. A. Bhat, K. L. Dhar, S. C. Puri, A. K. Saxena, M. Shanmugavel, G. N. Qazi. *Bioorg. Med. Chem Lett*, Vol 15, 12, 2005, 3177-3180; Gian Ceasure Tron, Tracy Pirali, Giovanni sorba, Francesca pagliai, Sara Buasacca and Armado A. Genazzani. J. Med. Chem. 2006, 49, 3033-3044. and Tracey Pirali, Sara buasacca, Lorena Beltrami, Daniela Imovilli, Francesca Paliai, Gianluca Migilio, Alberto Massrotti, Luisella Verotta, Gian Cesare Tron, Givanni Sorba, and Armado A. Genazzani. J. Med. Chem. 2006, 49, 5372-5376; Julia kaffy, Renee Pontikis, Daniele Carrez, Alain Croisy, Claude Monneret and Jean-Claude Florent. Bioorg. Med. Chem. 2006, 14, 4067-4077, Simoni, D.; Grisolia, G.; Giannini, G.; Roberti, M.; Rondanin, R.; Piccagli, L.; Baruchello, R.; Rossi, M.; Romagnoli, R.; Invidiata, F. P.; Grimaudo, S.; Jung, M. K.; Hamel, E.; Gebbia, N.; Crosta, L.; Abbadessa, V.; DiCristina, A.; Dusonchet, L.; Meli, M.; Tolomeo, M. J. Med. Chem. 2005, 48, 723).

These new analogues of olefine, chalcone, pyrazoline, pyrazole, isoxazole and isoxazoline linked amidobenzothiazole have shown promising anticancer activity in various cancer cell lines. The molecules synthesized are of immense biological significance.

EXAMPLES

The following examples are given by way of illustration and therefore should not be construed to the present limit of the scope of invention.

Example 1

N1-(1,3-Benzothiazol-2-yl)-2-{2-methoxy-5-[(Z)-2-(3,4,5-trimethoxyphenyl)-1-ethenyl] phenoxy}acetamide (8a)

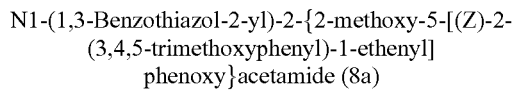

To a solution of 2-aminobenzothiazole (150 mg, 1.0 mmol) in dichloromethane (20 mL) was added 1-Ethyl-3-(3-Dimethylaminopropyl)carbodiimide (EDC) (191 mg, 1.0 mmol) and 1-hydroxy-1,2,3-benzotriazole (HOBt) (13.5 mg, 0.1 mmol). Then added 2-{2-methoxy-5-[(Z)-2-(3,4,5-trimethoxyphenyl)-1-ethenyl]phenoxy}acetic acid (1) (374 mg, 1.0 mmol) and the reaction mixture was stirred at a temperature of 25° C. for 24 h and the reaction was monitored by TLC. Then to this water is added and extracted with dichloromethane. The solvent was evaporated under vacuum to afford the crude product. This was further purified by column chromatography using ethyl acetate and hexane as solvent system to obtain the pure product (8a) (395 mg, 80% yield).

$^1$H NMR (CDCl$_3$): δ 7.74-7.82 (m, 2H), 7.37-7.44 (m, 1H), 7.29 (d, 1H, J=8.3 Hz), 6.96-7.01 (d, 1H, J=8.3, 2.2 Hz), 6.93 (d, 1H, J=2.2 Hz), 6.82 (d, 1H, J=8.3 Hz), 6.46 (d, 1H, J=12.0 Hz), 6.38-4.30 (m, 3H), 4.60 (s, 2H), 4.02 (s, 3H), 3.83 (s, 3H), 3.69 (s, 6H); ESIMS: 507 (M+1)$^+$.

Example 2

N1-(6-fluoro-1,3-benzothiazol-2-yl)-2-{2-methoxy-5-[(Z)-2-(3,4,5-trimethoxyphenyl)-1-ethenyl] phenoxy}acetamide (8e)

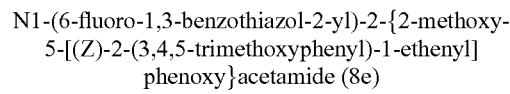

To a solution of 6-fluoro-2-aminobenzothiazole (168 mg, 1.0 mmol) in dichloromethane (20 mL) was added 1-Ethyl-3-(3-Dimethylaminopropyl)carbodiimide (EDC) (191 mg, 1.0 mmol) and 1-hydroxy-1,2,3-benzotriazole (HOBt) (13.5 mg, 0.1 mmol). Then added 2-{2-methoxy-5-[(Z)-2-(3,4,5-trimethoxyphenyl)-1-ethenyl]phenoxy}acetic acid(1) (374 mg, 0.1 mmol) and the reaction mixture was stirred at a temperature of 25° C. for 24 h and the reaction was monitored by TLC. Then to this water is added and extracted with dichloromethane. The solvent was evaporated under vacuum to afford the crude product. This was further purified by column chromatography using, ethyl acetate and hexane as solvent system to obtain the pure product (8e) (375 mg, 70% yield).

$^1$H NMR (CDCl$_3$): δ 7.71-7.76 (m, 1H), 7.47-7.53 (dd, 1H, J=8.1, 2.4 Hz), 7.13-7.20 (m, 1H), 7.00-7.04 (dd, 1H, J=8.1, 1.6 Hz), 6.93 (d, 1H, J=1.6 Hz), 6.83 (d, 1H, J=8.1 Hz), 6.46-6.51 (m, 3H), 6.44 (d, 1H, J=12.2 Hz), 4.63 (s, 2H), 3.98 (s, 3H), 3.85 (s, 3H), 3.70 (s, 6H); ESIMS: 525 (M+1)$^+$.

Example 3

N1-[6-(trifluoromethyl)-1,3-benzothiazol-2-yl]-2-{2-methoxy-5-[(Z)-2-(3,4,5-trimethoxy phenyl)-1-ethenyl]phenoxy}acetamide (8i)

To a solution of 6-(trifluoromethyl)-2-aminobenzothiazole (218 mg, 1.0 mmol) in dichloromethane (20 mL) was added 1-Ethyl-3-(3-Dimethylaminopropyl)carbodiimide (EDC) (191 mg, 1.0 mmol) and 1-hydroxy-1,2,3-benzotriazole (HOBt) (13.5 mg, 0.1 mmol). Then added 2-{2-methoxy-5-[(Z)-2-(3,4,5-trimethoxyphenyl)-1-ethenyl]phenoxy}acetic ac id (1) (374 mg, 0.1 mmol) and the reaction mixture was stirred at a temperature of 25° C. for 24 h and the reaction was monitored by TLC. Then to this water is added and extracted with dichloromethane. The solvent was evaporated under vacuum to afford the crude product. This was further purified by column chromatography using ethyl acetate and hexane as solvent system to obtain the pure product (8i) (450 mg, 80% yield)

$^1$H NMR (CDCl$_3$): δ 8.12 (s, 1H), 7.93 (d, 1H, J=8.4 Hz), 7.69-7.75 (m, 1H), 7.01-7.06 (dd, 1H, J=8.3, 1.7 Hz), 6.95 (d, 1H, J=1.7 Hz), 6.85 (d, 1H, J=8.3 Hz), 6.43-6.53 (m, 1H), 4.68 (s, 2H), 3.99 (s, 3H), 3.83 (s, 3H), 3.70 (s, 6H); ESIMS: 575 (M+1)$^+$.

Example 4

N1-[6-(trifluoromethoxy)-1,3-benzothiazol-2-yl]-2-{2-methoxy-5-[(Z)-2-(3,4,5-trimethoxy phenyl)-1-ethenyl]phenoxy}acetamide (8j)

To a solution of 6-(trifluoromethoxy)-2-aminobenzothiazole (234 mg, 1.0 mmol) in dichloromethane (20 mL) was added 1-Ethyl-3-(3-Dimethylaminopropyl)carbodiimide (EDC) (191 mg, 1.0 mmol) and 1-hydroxy-1,2,3-benzotriazole (HOBt) (13.5 mg, 0.1 mmol). Then added 2-{2-methoxy-5-[(Z)-2-(3,4,5-trimethoxyphenyl)-1-ethenyl]phenoxy}acetic acid (1) (374 mg, 0.1 mmol) and the reaction mixture was stirred at a temperature of 25° C. for 24 h and the reaction was monitored by TLC. Then to this water is added and extracted with dichloromethane. The solvent was evaporated under vacuum to afford the crude product. This was further purified by column chromatography using ethyl acetate and hexane as solvent system to obtain the pure product (8j) (470 mg, 80% yield)

$^1$H NMR (CDCl$_3$): δ 7.80 (d, 1H, J=8.8 Hz), 7.69 (s, 1H), 7.29-7.36 (dd, 1H, J=8.4, 2.2 Hz), 7.01-7.06 (dd, 1H, J=8.4, 1.7 Hz), 6.95 (d, 1H, J=1.7 Hz), 6.85 (d, 1H, J=8.3 Hz), 6.42-6.53 (m, 4H), 4.65 (s, 2H), 3.99 (s, 3H), 3.85 (s, 3H), 3.70 (s, 6H); ESIMS: 591 (M+1)$^+$

Example 5

N1-(4-methyl-1,3-benzothiazol-2-yl)-2-{2-methoxy-5-[(E)-3-oxo-3-(3,4,5-trimethoxy phenyl)-1-propenyl]phenoxy}acetamide (9k)

To a solution of 4-methyl-2-aminobenzothiazole (164 mg, 1.0 mmol) in dichloromethane (20 mL) was added 1-Ethyl-3-(3-Dimethylaminopropyl)carbodiimide (EDC) (191 mg, 1.0 mmol) and 1-hydroxy-1,2,3-benzotriazole (HOBt) (13.5 mg, 0.1 mmol). Then added 2-{2-methoxy-5-[(E)-3-oxo-3-(3,4,5-trimethoxy phenyl)-1-propenyl]phenoxy}acetic acid (2) (402 mg, 0.1 mmol) and the reaction mixture was stirred at a temperature of 25° C. for 24 h and the reaction was monitored by TLC. Then to this water is added and extracted with dichloromethane. The solvent was evaporated under vacuum to afford the crude product. This was further purified by column chromatography using ethyl acetate and hexane as solvent system to obtain the pure product (9k) (440 mg, 80% yield)

$^1$H NMR (CDCl$_3$): δ 10.71 (br s, 1H), 7.76 (d, 1H, J=15.4 Hz), 7.65-7.70 (m, 1H), 7.32-7.43 (m, 4H), 7.28 (s, 2H), 7.22-7.26 (m, 1H), 7.02 (d, 1H, J=8.4 Hz), 4.86 (s, 2H), 4.09 (s, 3H), 3.96 (s, 6H), 3.94 (s, 3H), 2.67 (s, 3H); ESIMS: 549 (M+1)$^+$.

Example 6

N1-(6-ethoxy-1,3-benzothiazol-2-yl)-2-{2-methoxy-5-[(E)-3-oxo-3-(3,4,5-trimethoxy phenyl)-1-propenyl]phenoxy}acetamide (9h)

To a solution of 6-ethoxy-2-aminobenzothiazole (194 mg, 1.0 mmol) in dichloromethane (20 mL) was added 1-Ethyl-3-(3-Dimethylaminopropyl)carbodiimide (EDC) (191 mg, 1.0 mmol) and 1-hydroxy-1,2,3-benzotriazole (HOBt) (13.5 mg, 0.1 mmol). Then added 2-{2-methoxy-5-[(E)-3-oxo-3-(3,4,5-trimethoxy phenyl)-1-propenyl]phenoxy}acetic acid (2) (402 mg, 0.1 mmol) and the reaction mixture was stirred at a temperature of 25° C. for 24 h and the reaction was monitored by TLC. Then to this water is added and extracted with dichloromethane. The solvent was evaporated under vacuum to afford the crude product. This was further purified by column chromatography using ethyl acetate and hexane as solvent system to obtain the pure product (9h) (452 mg, 80% yield).

$^1$H NMR (CDCl$_3$): δ 7.75 (d, 1H, J=15.8 Hz), 7.70 (d, 1H, J=9.0 Hz), 7.36-7.41 (m, 2H), 7.29-7.34 (m, 2H), 7.25-7.28 (m, 3H), 7.01 (d, 1H, J=8.3 Hz), 4.84 (s, 2H), 4.06-4.15 (q, 2H), 4.04 (s, 3H), 3.96 (s, 6H), 3.95 (s, 3H), 1.46 (t, 3H); ESIMS: 565 (M+1)$^+$.

Example 7

N1-[6-(trifluoromethyl)-1,3-benzothiazol-2-yl]-2-{2-methoxy-5-[(E)-3-oxo-3-(3,4,5-trimethoxyphenyl)-1-propenyl]phenoxy}acetamide (9i)

To a solution of 6-(trifluoromethyl)-2-aminobenzothiazole (218 mg, 1.0 mmol) in dichloromethane (20 mL) was added 1-Ethyl-3-(3-Dimethylaminopropyl)carbodiimide (EDC) (191 mg, 1.0 mmol) and 1-hydroxy-1,2,3-benzotriazole (HOBt) (13.5 mg, 0.1 mmol). Then added 2-{2-methoxy-5-[(E)-3-oxo-3-(3,4,5-trimethoxy phenyl)-1-propenyl]phenoxy}acetic acid (2) (402 mg, 0.1 mmol) and the reaction mixture was stirred at a temperature of 25° C. for 24 h and the reaction was monitored by TLC. Then to this water is added and extracted with dichloromethane. The solvent was evaporated under vacuum to afford the crude product. This was further purified by column chromatography using ethyl acetate and hexane as solvent system to obtain the pure product (9i) (480 mg, 80% yield)

$^1$H NMR (CDCl$_3$): δ 10.74 (br s, 1H), 8.11 (s, 1H), 7.87 (d, 1H, J=8.3 Hz), 7.64-7.74 (m, 2H), 7.28-7.40 (m, 3H), 7.22 (s, 2H), 6.99 (d, 1H, J=8.3 Hz), 4.84 (s, 2H), 4.09 (s, 3H), 3.95 (s, 6H), 3.91 (s, 3H); ESIMS: 603 (M+1)$^+$.

Example 8

N1-[6-(trifluoromethoxy)-1,3-benzothiazol-2-yl]-2-{2-methoxy-5-[(E)-3-oxo-3-(3,4,5-trimethoxyphenyl)-1-propenyl]phenoxy}acetamide (9j)

To a solution of 6-(trifluoromethoxy)-2-aminobenzothiazole (234 mg, 1.0 mmol) in dichloromethane (20 mL) was added 1-Ethyl-3-(3-Dimethylaminopropyl)carbodiimide (EDC) (191 mg, 1.0 mmol) and 1-hydroxy-1,2,3-benzotriazole (HOBt) (13.5 mg, 0.1 mmol). Then added 2-{2-methoxy-5-[(E)-3-oxo-3-(3-(3,4,5-trimethoxy phenyl)-1-propenyl]phenoxy}acetic acid (2) (402 mg, 0.1 mmol) and the reaction mixture was stirred at a temperature of 25° C. for 24 h and the reaction was monitored by TLC. Then to this water is added and extracted with dichloromethane. The solvent was evaporated under vacuum to afford the crude product. This was further purified by column chromatography using ethyl acetate and hexane as solvent system to obtain the pure product (9j) (498 mg, 80% yield)

$^1$H NMR (CDCl$_3$): □□10.62 (br s, 1H), 7.77 (d, 1H, J=9.0 Hz), 7.66-7.73 (m, 2H), 7.27-7.39 (m, 3H), 7.24 (d, 1H, J=15.1 Hz), 7.22 (s, 2H), 6.98 (d, 1H, J=8.3 Hz), 4.83 (s, 2H), 4.07 (s, 3H), 3.95 (s, 6H), 3.91 (s, 3H); ESIMS: 619 (M+1)$^+$.

Example 9

N1-(1,3-benzothiazol-2-yl)-2-{5-[1-acetyl-3-(3,4,5-trimethoxyphenyl)-4,5-dihydro-1H-5-pyrazolyl]-2-methoxyphenoxy}acetamide (10a)

To a solution of 2-aminobenzothiazole (359.37 ma, 1.0 mmol) in dichloromethane (20 mL) was added 1-Ethyl-3-(3-Dimethylaminopropyl)carbodiimide (EDC) (191 mg, 1.0 mmol) and 1-hydroxy-1,2,3-benzotriazole (HOBt) (13.5 ma, 0.1 mmol). Then added 2-{5-[1-acetyl-3-(3,4,5-trimethoxyphenyl)-4,5-dihydro-1H-5-pyrazolyl]-2-methoxyphenoxy}acetic acid (3) (458 mg, 0.1 mmol) and the reaction mixture was stirred at a temperature of 25° C. for 24 h and the reaction was monitored by TLC. Then to this water is added and extracted with dichloromethane. The solvent was evaporated under vacuum to afford the crude product. This was further purified by column chromatography using ethyl acetate and hexane as solvent system to obtain the pure product (10a) (472 mg, 80% yield)

$^1$H NMR (CDCl$_3$): δ 7.73-7.81 (m, 2H), 7.40 (t, 1H), 7.29 (d, 1H, J=7.3 Hz), 6.92-6.97 (m, 1H), 6.85-6.91 (m, 4H), 5.44-5.53 (dd, 1H, J=11.7, 4.5 Hz), 4.69 (s, 2H), 3.99 (s, 3H), 3.90 (s, 6H), 3.86 (s, 3H), 3.64-3.76 (dd, 1H, J=11.8, 17.3 Hz), 3.04-3.14 (dd, 1H, J=17.3, 4.5 Hz), 2.40 (s, 3H); ESIMS: 591 (M+1)$^+$.

Example 10

N1-[6-(trifluoromethyl)-1,3-benzothiazol-2-yl]-2-{5-[1-acetyl-3-(3,4,5-trimethoxy phenyl)-4,5-dihydro-1H-5-pyrazolyl]-2-methoxyphenoxy}acetamide (10i)

To a solution of 6-(trifluoromethyl)-2-aminobenzothiazole (218 mg, 1.0 mmol) in dichloromethane (20 mL) was added 1-Ethyl-3-(3-Dimethylaminopropyl)carbodiimide (EDC) (191 mg, 1.0 mmol) and 1-hydroxy-1,2,3-benzotriazole (HOBt) (13.5 mg, 0.1 mmol). Then added 2-{5-[1-acetyl-3-(3,4,5-trimethoxyphenyl)-4,5-dihydro-1H-5-pyrazolyl]-2-methoxyphenoxy}acetic acid (3) (458 mg, 0.1 mmol) and the reaction mixture was stirred at a temperature of 25° C. for 24 h and the reaction was monitored by TLC. Then to this water is added and extracted with dichloromethane. The solvent was evaporated under vacuum to afford the crude product. This was further purified by column chromatography using ethyl acetate and hexane as solvent system to obtain the pure product (10i) (528 mg, 80% yield).

$^1$H NMR (CDCl$_3$): δ 10.82 (br s, 1H), 8.11 (s, 1H), 7.88 (d, 1H, J=7.9 Hz), 7.67-7.70 (m, 1H), 6.98-7.02 (dd, 1H, J=7.9, 1.6 Hz), 6.96 (s, 2H), 6.90-6.94 (m, 2H), 5.51-5.56 (dd, 1H, J=11.9, 3.9 Hz), 4.79 (s, 2H), 3.99 (s, 3H), 3.91 (s, 6H), 3.89 (s, 3H), 3.71-3.79 (dd, 1H, J=11.9, 17.5 Hz), 3.10-3.15 (dd, 1H, J=17.5, 4.7 Hz), 2.43 (s, 3H); ESIMS: 659 (M+1)$^+$.

Example 11

N1-[6-(trifluoromethoxy)-1,3-benzothiazol-2-yl]-2-{5-[1-acetyl-3-(3,4,5-trimethoxy phenyl)-4,5-dihydro-1H-5-pyrazolyl]-2-methoxyphenoxy}acetamide (10j)

To a solution of 6-(trifluoromethoxy)-2-aminobenzothiazole (234 mg, 1.0 mmol) in dichloromethane (20 mL) was added 1-Ethyl-3-(3-Dimethylaminopropyl)carbodiimide (EDC) (191 mg, 1.0 mmol) and 1-hydroxy-1,2,3-benzotriazole (HOBt) (13.5 mg, 0.1 mmol). Then added 2-{5-[1-acetyl-3-(3,4,5-trimethoxyphenyl)-4,5-dihydro-1H-5-pyrazolyl]-2-methoxyphenoxy}acetic acid (3) (458 mg, 0.1 mmol) and the reaction mixture was stirred at a temperature of 25° C. for 24 h and the reaction was monitored by TLC. Then to this water is added and extracted with dichloromethane. The solvent was evaporated under vacuum to afford the crude product. This was further purified by column chromatography using ethyl acetate and hexane as solvent system to obtain the pure product (10j) (531 mg, 80% yield).

$^1$H NMR (CDCl$_3$): δ 10.71 (br s, 1H), 7.79 (d, 1H, J=8.3 Hz), 7.69 (d, 1H, J=1.5 Hz), 7.29-7.34 (dd, 1H, J=9.0, 1.5 Hz), 6.98-7.02 (dd, 1H, J=8.3, 1.5 Hz), 6.96 (s, 2H), 6.89-6.94 (m, 2H), 5.50-5.58 (dd, 1H, J=11.3, 4.5 Hz), 4.77 (s, 2H), 3.98 (s, 3H), 3.91 (s, 6H), 3.90 (s, 3H), 3.69-3.81 (dd, 1H, J=18.1, 12.0 Hz), 3.08-3.17 (dd, 1H, J=17.3, 4.5 Hz), 2.43 (s, 3H); ESIMS: 675 (M+1)$^+$.

Biological Activity

The in vitro anticancer activity studies for these amidobenzothiazoles were carried out at the National Cancer Institute, Maryland, USA.

In Vitro Cytotoxicity

The amidobenzothiazoles have been tested against sixty human tumor cell lines derived from nine cancer types (leukemia cancer cell line, non-small cell lung cancer cell line, colon cancer cell line, CNS cancer cell line, melanoma cancer cell line, ovarian cancer cell line, renal cancer cell line, prostate cancer cell line and breast cancer cell lines). For these compounds results are expressed in GI50 values of that particular cancer cell at micro molar (μM) concentration as per NCI protocol. The compounds 8a, 8e, 8g, 8i, 8j, 9a, 9e, 9g, 9i, 9j, and 10i were evaluated for in vitro anticancer activity against sixty human tumor cells derived from nine cancer types (leukemia, non-small cell lung cancer, colon cancer, CNS cancer, melanoma cancer, ovarian cancer, renal cancer, prostate cancer and breast cancer) at concentration of μM and the results are shown in Tables 2.

The compounds 8a, 8e, 8g, 8i, 8j, 9a, 9e, 9g, 9i, 9j and 10i exhibited an interesting profile of anti cancer activity against various cancer cell lines.

TABLE 2

In vitro cytotoxicity of compounds 8a, 8e, 8g, 8i, 8j, 9a, 9e, 9g, 9i, 9j and 10i against sixty human cancer cell lines.

| Panel/Cell Line | GI50 values (µM conc.) | | | | | | | | | | |
|---|---|---|---|---|---|---|---|---|---|---|---|
| | 8a | 8e | 8g | 8i | 8j | 9a | 9e | 9g | 9i | 9j | 10i |
| Leukemia | | | | | | | | | | | |
| CCRF-CEM | 0.078 | 3.70 | 3.87 | 4.27 | 4.12 | 2.09 | 5.73 | 3.55 | 3.37 | 2.5 | — |
| HL-60(TB) | — | — | — | — | — | — | — | — | — | — | — |
| K-562 | 0.042 | 3.62 | 3.6 | 3.3 | 3.43 | 0.44 | 4.32 | 3.52 | 3.67 | 0.43 | — |
| MOLT-4 | 0.34 | 3.07 | 3.87 | 3.75 | 4.21 | 3.03 | 29.9 | 3.5 | 4.31 | 2.89 | — |
| RPMI-8226 | 0.15 | 6.36 | 5.43 | 5.48 | 5.83 | 1.09 | 7.35 | 3.02 | 3.84 | 2.02 | 2.21 |
| SR | 0.037 | 2.19 | 3.69 | 3.35 | 3.55 | 0.38 | 3.17 | 2.53 | 0.85 | 0.39 | — |
| Non-small cell lung | | | | | | | | | | | |
| A549/ATCC | 0.34 | 5.99 | 5.19 | 4.46 | 6 | 2.63 | 23.2 | 11.7 | 14.3 | 1.99 | 2.16 |
| EKVX | 0.038 | 5.72 | 5.11 | 6.25 | 7.89 | 5.91 | 38.1 | 50.3 | 30.3 | 5.11 | 4.1 |
| HOP-62 | — | 5.70 | 23 | 5.22 | 7.09 | 6.11 | 11.7 | 4.11 | 6.57 | 2.12 | 2.2 |
| HOP-92 | 0.039 | 5.73 | 6.28 | 2.88 | 2.74 | 1.33 | 2.39 | 2.62 | 4.1 | 2.14 | 1.7 |
| NCI-H226 | 0.27 | 5.60 | 4.51 | 3.17 | 4.3 | 2.77 | 21.1 | 32.5 | 21.5 | 3.35 | 2.22 |
| NCI-H23 | 0.11 | 4.26 | 3.91 | 3.9 | 4.39 | 3.4 | 11 | 5.06 | 3.68 | 2.15 | 3.76 |
| NCI-H322M | — | >100 | >100 | 5.38 | >100 | 4.26 | 38.1 | 7.16 | 6.73 | 2.77 | 3.67 |
| NCI-H460 | 0.052 | 4.36 | 3.73 | 3.55 | 4.11 | 2.64 | 13.5 | 3.32 | 4.06 | 2.43 | — |
| NCI-H522 | 0.079 | 2.92 | 3.09 | 2.89 | 3.16 | 1.32 | 3.2 | 2.16 | 2 | 0.67 | 2.71 |
| Colon | | | | | | | | | | | |
| COLO-205 | 2.83 | 7.78 | 3.89 | 17.1 | 43.3 | 5.47 | 26.8 | 58.5 | 37.7 | 6.37 | 3.94 |
| HCC-2998 | 0.37 | >100 | 7.34 | 4.23 | 17.1 | 2.14 | 33 | 19.3 | 21.3 | 6.18 | >100 |
| HCT-116 | 0.046 | 4.48 | 3.7 | 3.29 | 3.92 | 2.88 | 15.7 | 3.98 | 3.83 | 1.43 | 2.39 |
| HCT-15 | 0.048 | 8.19 | 2.89 | 3.24 | 3.23 | 0.49 | 3.96 | 3.34 | 2.68 | 0.4 | 9.26 |
| HT29 | 3.16 | 9.63 | 3.34 | 14.9 | >100 | 3.49 | 94.8 | 32.4 | 21.5 | 3.66 | — |
| KM12 | 0.058 | 4.78 | 3.12 | 3.14 | 4.48 | 0.36 | 2.97 | 2.4 | 1.77 | 1.51 | — |
| SW-620 | — | 65 | 5.1 | 4.65 | 5.65 | 0.62 | 3.84 | 4.07 | 3.82 | 1.08 | >100 |
| CNS | | | | | | | | | | | |
| SF-268 | 0.18 | 7.23 | 4.31 | 3.85 | 6.01 | 0.95 | 3.78 | 4.16 | 3.28 | 1.2 | 3.84 |
| SF-295 | 0.22 | 4.29 | 1.84 | 3.36 | 3.7 | 3.41 | 18.8 | 6.68 | 8.87 | 2.21 | 3.06 |
| SF-539 | 0.045 | 4.51 | 2.84 | 2.66 | 2.28 | 0.34 | 2.49 | 2.17 | 2.1 | 0.29 | 1.75 |
| SNB-19 | — | >100 | 6.3 | 5.03 | 7.08 | 2.81 | 17.3 | 5.61 | 6.01 | 1.58 | 11 |
| SNB-75 | 0.046 | 4.39 | 1.91 | 1.58 | 1.56 | 0.53 | 1.67 | 2.04 | 2.2 | 0.34 | 1.55 |
| U251 | 0.048 | 4.33 | 4 | 3.67 | 3.37 | 0.96 | 6.08 | 3.08 | 3.27 | 0.7 | 3.08 |
| Melanoma | | | | | | | | | | | |
| LOX IMVI | 0.067 | 3.23 | 4.17 | 4.01 | 4.77 | 0.52 | 3.37 | 2.59 | 2.88 | 0.47 | 3.36 |
| MALME-3M | 1.99 | 5.22 | >100 | >100 | — | 6.42 | 27.7 | 9.62 | 8.75 | 2.69 | 6.44 |
| M14 | 0.072 | 6.82 | 4.33 | 3.58 | 4.36 | 3.29 | 10.7 | 3.28 | 3.31 | 1.72 | — |
| MDA-MB-435 | 0.019 | 0.33 | 1.16 | 1.84 | 1.93 | 0.3 | 1.93 | 1.51 | 1.16 | 0.3 | 3.08 |
| SK-MEL-2 | 0.18 | 8.46 | 4.07 | 3.98 | 3.29 | 5.39 | 100 | 24.2 | 30 | 4.97 | — |
| SK-MEL-28 | — | >100 | 4.41 | 3 | 4.57 | 4.61 | 24.1 | 14.4 | 9.47 | 3.31 | 3.56 |
| SK-MEL-5 | 0.036 | 1.76 | 2.68 | 2.84 | 3.26 | 1.76 | 4.49 | 4.56 | 2.88 | 2.03 | — |
| UACC-257 | 11 | 8.69 | 63 | 40 | 89.2 | 1.37 | 73.2 | 20.4 | 49.5 | 8.08 | 3.77 |
| UACC-62 | 0.063 | 4.05 | 5.93 | 3.9 | 5.11 | 7.87 | 33.6 | 14.5 | 22.7 | 9.52 | |
| Ovarian | | | | | | | | | | | |
| IGROV1 | 0.21 | 4.17 | 7 | 4.48 | 5.64 | 3.6 | 16.2 | 7.73 | 15.6 | 2.54 | 5.3 |
| OVCAR-3 | 0.043 | 9.99 | 2.17 | 2.11 | 3.37 | 0.48 | 3.4 | 2.6 | 1.95 | 1.52 | 1.84 |
| OVCAR-4 | 0.37 | 7.30 | 5.31 | 4.66 | 5.34 | 3.2 | 14.7 | 11.2 | 4.37 | 2.07 | 2.9 |
| OVCAR-5 | — | >100 | 5.89 | 5.98 | 3.12 | 3.54 | 91.6 | 71.7 | 38.9 | 4.76 | 28.2 |
| OVCAR-8 | 0.25 | 7.15 | 5.28 | 3.86 | 5 | 2.77 | 10.2 | 3.49 | 3.85 | 1.54 | 3.36 |
| NCI/ADR-RES | 0.033 | 2.55 | 2.3 | 2.12 | 2.7 | 0.48 | 2.43 | 1.89 | 1.73 | 0.49 | 3.13 |
| SK-OV-3 | 0.34 | 8 | 4.69 | 3.29 | 8.42 | 2.54 | 15.2 | 7.32 | 5.08 | 2.16 | 5.75 |
| Renal | | | | | | | | | | | |
| 786-0 | 7.3 | 7.12 | 7.52 | 6.96 | 54.3 | 4.12 | 24.7 | 19.4 | 24.6 | 2.26 | 3.58 |
| A498 | 0.36 | 6.25 | 3.5 | 2.81 | 3.61 | 22.6 | 100 | 100 | 100 | 7.4 | 2.78 |
| ACHN | 0.093 | 3.33 | 7.77 | 4.82 | 8.31 | 3.46 | 12.4 | 4.94 | 7.48 | 1.62 | 2.48 |
| CAKI-1 | 0.41 | 2.78 | 3.2 | 3.1 | 4.6 | 3.78 | 30.7 | 25.1 | 10.9 | 2.2 | 2.17 |
| RXF 393 | 0.05 | 6.29 | 2.5 | 2.27 | 2.65 | 1.83 | 8.5 | 2.37 | 2.6 | 1.58 | 2.09 |
| SN12C | 0.37 | 4.61 | 5.75 | 4.43 | 6.42 | 3.02 | 17.4 | 5.19 | 5.41 | 1.74 | 3.31 |
| TK-10 | — | 9.89 | 7.54 | 7.03 | 18.6 | 3.3 | 20.9 | 16.4 | 15.6 | 2.08 | 2.85 |
| UO-31 | 0.58 | 2.56 | 4.31 | 3.59 | 4.37 | 3.07 | 6.83 | 5.31 | 7.8 | 1.61 | 1.93 |

TABLE 2-continued

In vitro cytotoxicity of compounds 8a, 8e, 8g, 8i, 8j, 9a, 9e, 9g, 9i, 9j and 10i against sixty human cancer cell lines.

| Panel/Cell Line | GI50 values (μM conc.) | | | | | | | | | | |
|---|---|---|---|---|---|---|---|---|---|---|---|
| | 8a | 8e | 8g | 8i | 8j | 9a | 9e | 9g | 9i | 9j | 10i |
| Prostate | | | | | | | | | | | |
| PC-3 | 0.18 | 6.74 | 4.45 | 4.32 | 5.12 | 3.63 | 22.9 | 12.2 | 12 | 3.14 | 2.92 |
| DU-145 | 0.1 | 8.97 | 2.04 | 2.51 | 4.11 | 1.94 | 4.05 | 2.49 | 2.62 | 1.56 | 1.82 |
| Breast | | | | | | | | | | | |
| MCF7 | 0.051 | 2.3 | 2.88 | 3.16 | 2.89 | 1.05 | 3.7 | 3.02 | 3.05 | 1.32 | 4.02 |
| MDA-MB-231/ATCC | 0.19 | 9.34 | 5.4 | 3.38 | 5.16 | 2.69 | 12.6 | 5.82 | 7.14 | 2.01 | 3.11 |
| HS 578T | — | >100 | 4.15 | 4.18 | 4.33 | 4.75 | 10.5 | 3.72 | 4.81 | 3.08 | 2.48 |
| BT-549 | 0.41 | 16.7 | 21.2 | 5.23 | 10.5 | 4.82 | 4.82 | 8.38 | 11.2 | 2.71 | 3.55 |
| T-47D | 1.0 | 3.39 | 4.03 | 4.79 | 3.95 | 4.97 | 58.5 | 14.7 | 15 | 3.08 | 2.75 |
| MDA-MB-468 | 0.1 | 3.68 | 2.29 | 2.16 | 2.3 | 2.3 | 13.1 | 10.5 | 13.5 | 3.52 | 6.12 |

ADVANTAGES OF THE INVENTION

1. The present invention provides amidobenzothiazole of general formula A useful as anticancer agents.
2. It also provides a process for the preparation of amidobenzothiazole of general formula A.

We claim:

1. An amidobenzothiazole of formula A

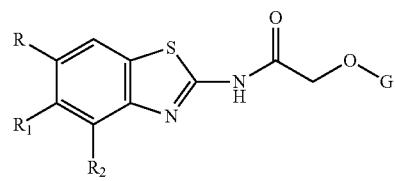

formula A

Wherein:

R=H, alkoxy, halo, haloalkyl, halomethyl, or nitro, $R_1$=H, alkoxy, halo, haloalkyl, halomethyl, or nitro, $R_2$=H, halo, haloalkyl, halomethyl, or nitro, and

G =

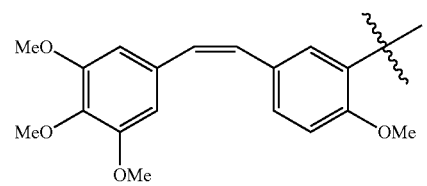 or

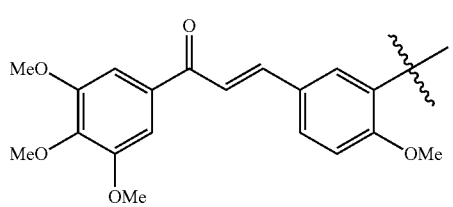 or

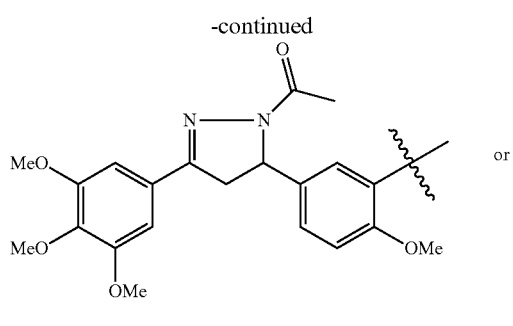 or

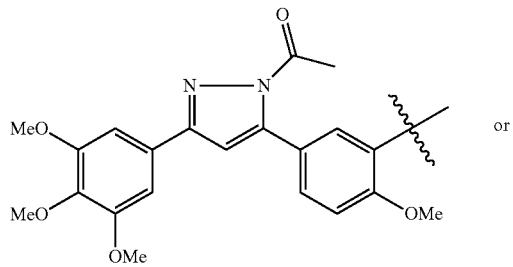 or

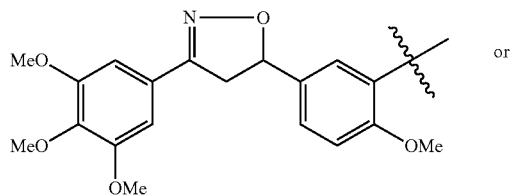 or

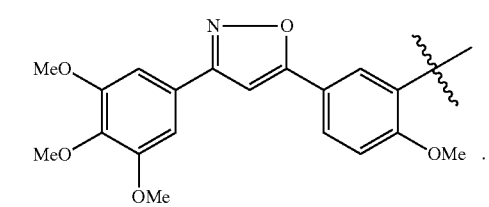

2. An amidobenzothiazole compound having a formula selected from the group consisting of compounds 8a-8v, 9a-9v, 10a-10v, 11a-11v, 12a-12v and 13a-13v shown below:

-continued
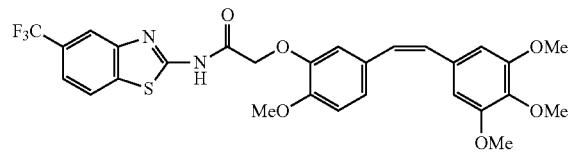
8s
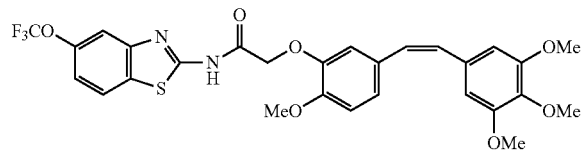
8t
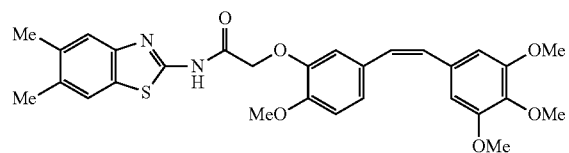
8u
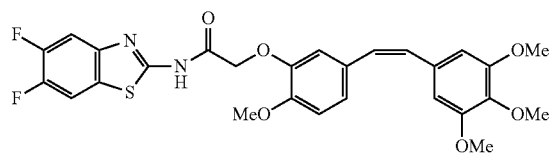
8v
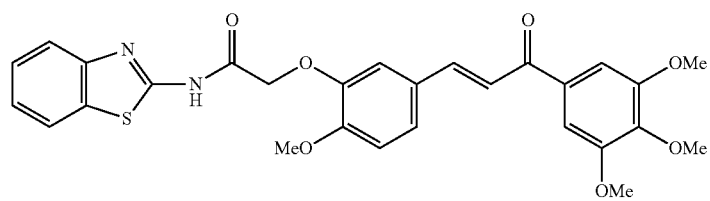
9a
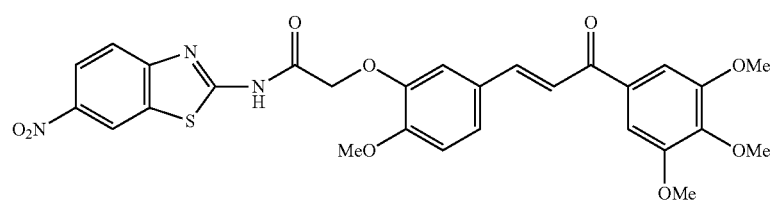
9b
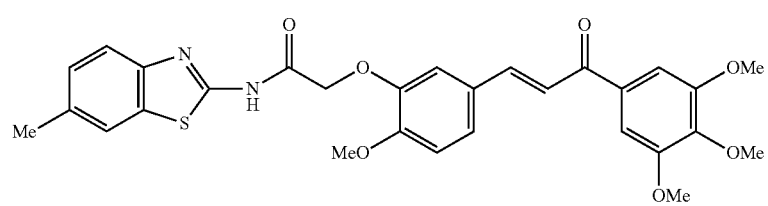
9c
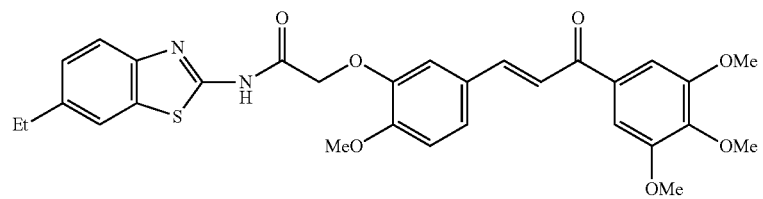
9d
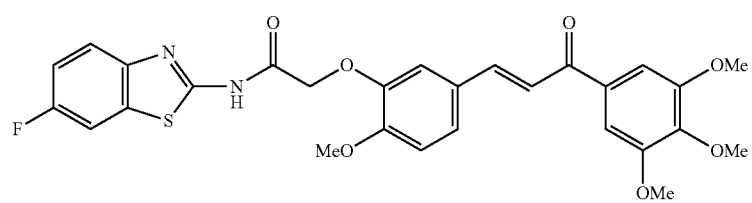
9e
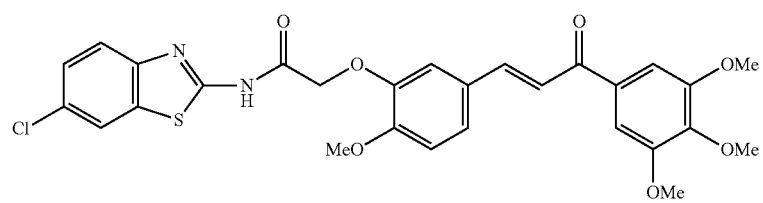
9f -continued
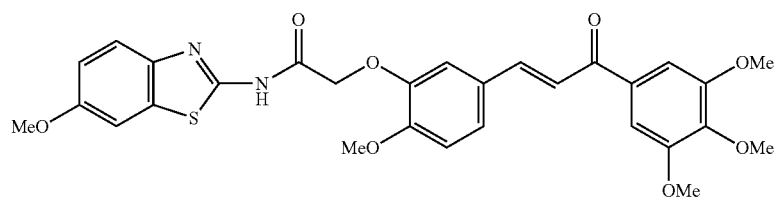
9g
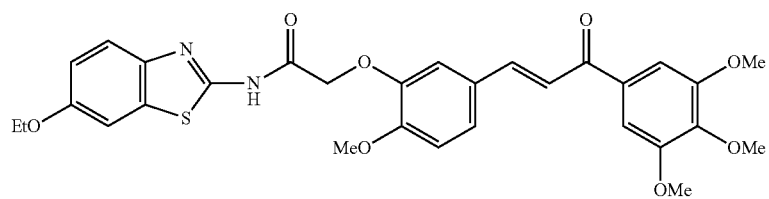
9h
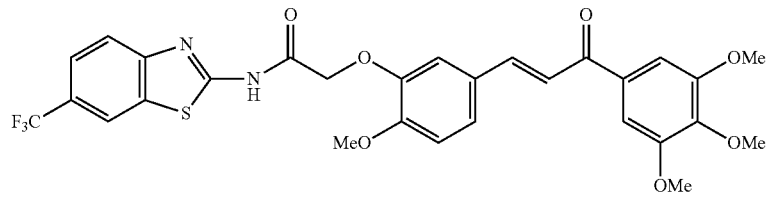
9i
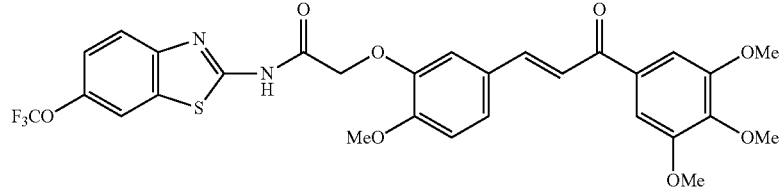
9j
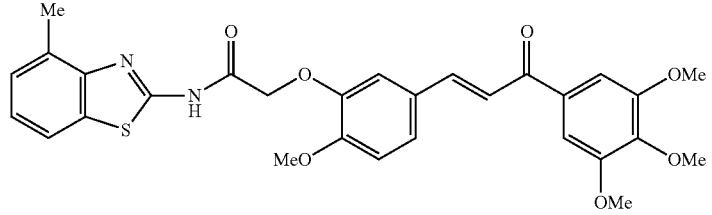
9k
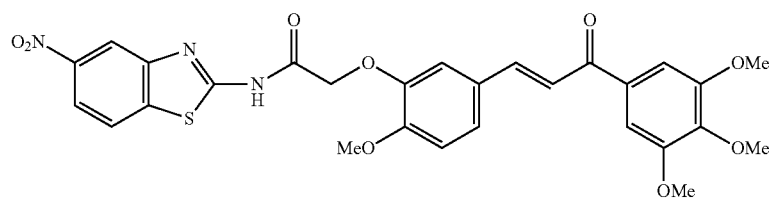
9l
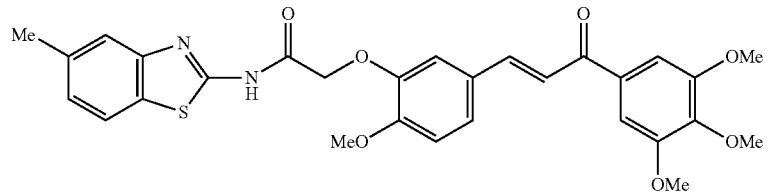
9m
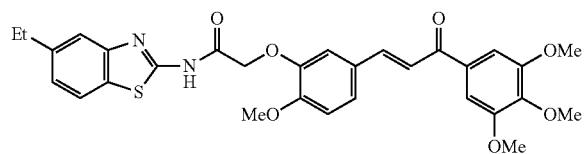
9n
9o

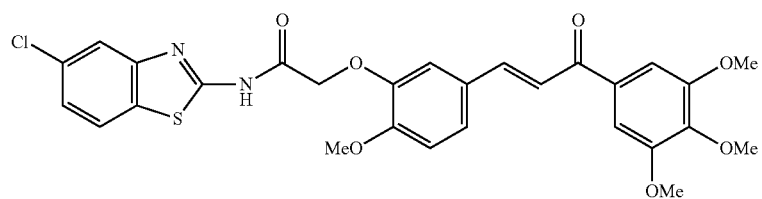
9p
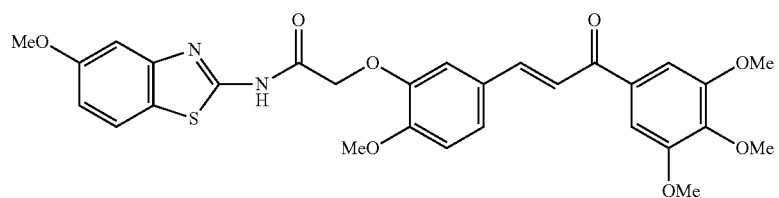
9q
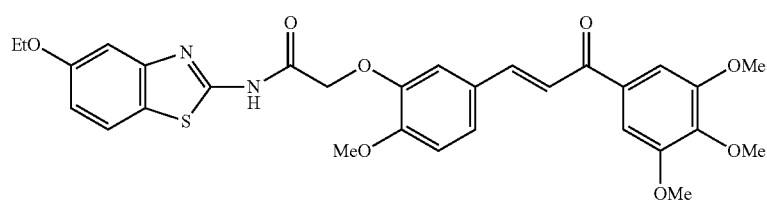
9r
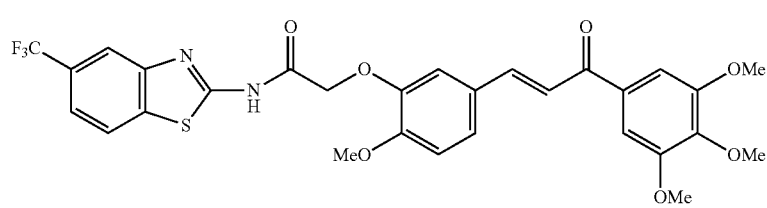
9s
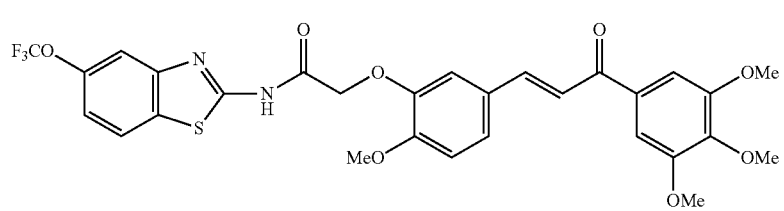
9t
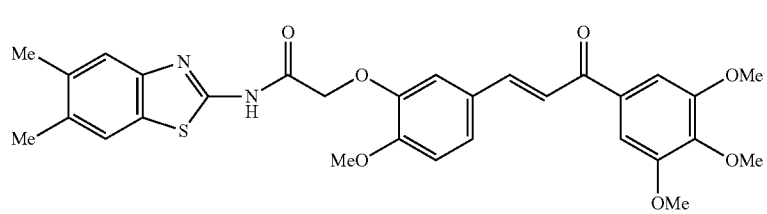
9u
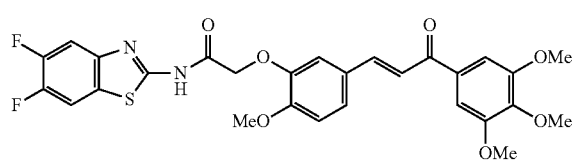
9v
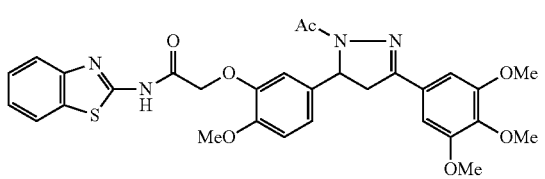
10a
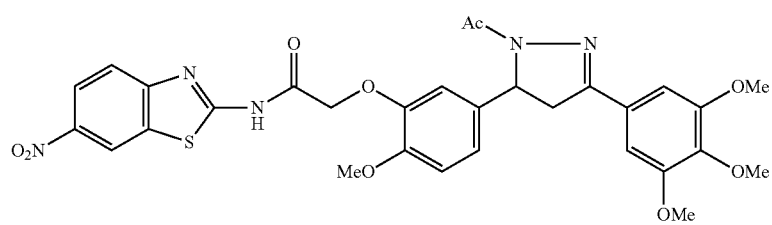
10b -continued
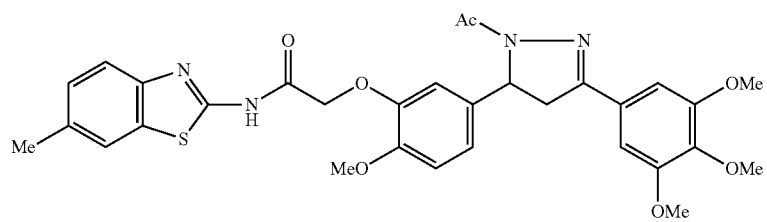
10c
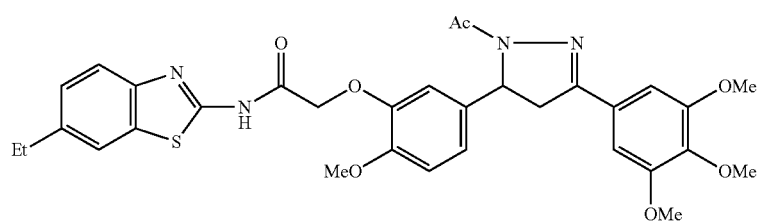
10d
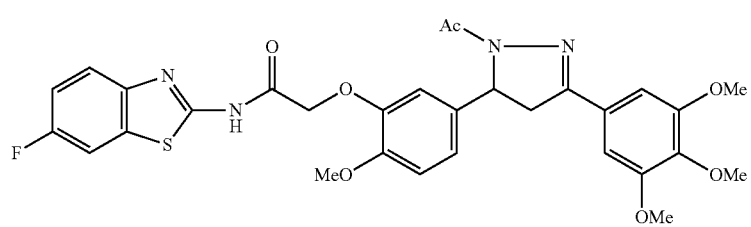
10e
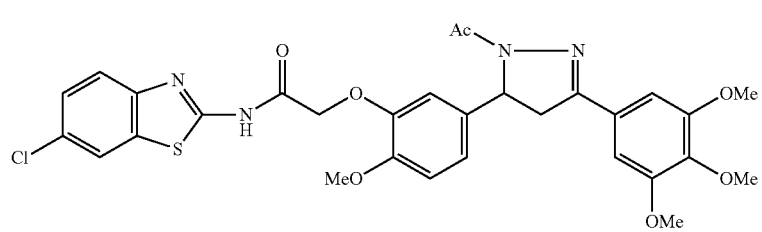
10f
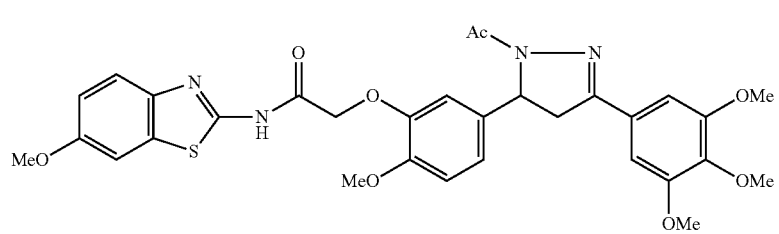
10g
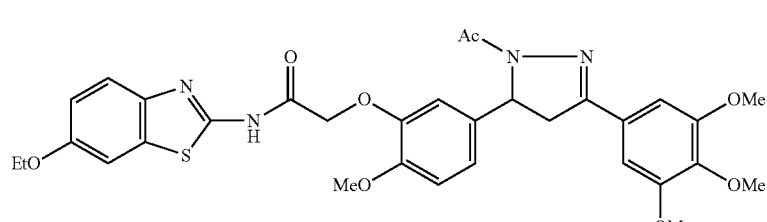
10h
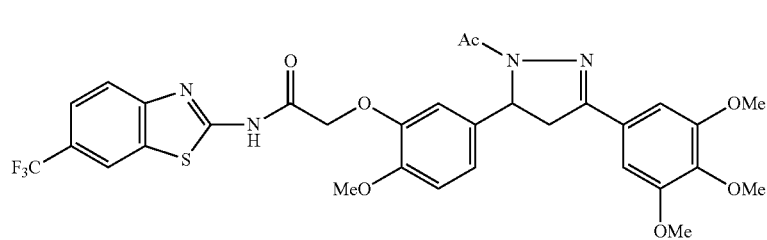
10i -continued
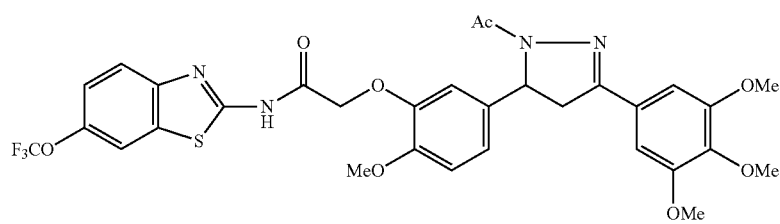
10j
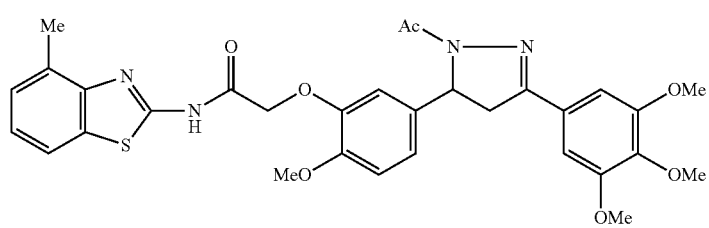
10k
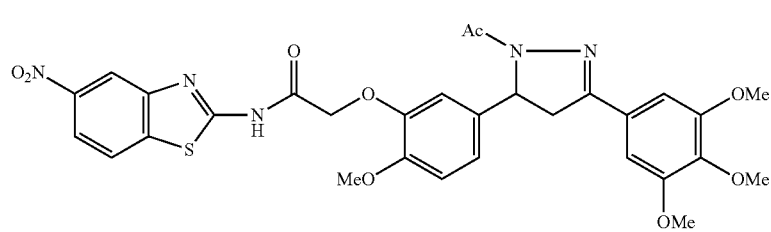
10l
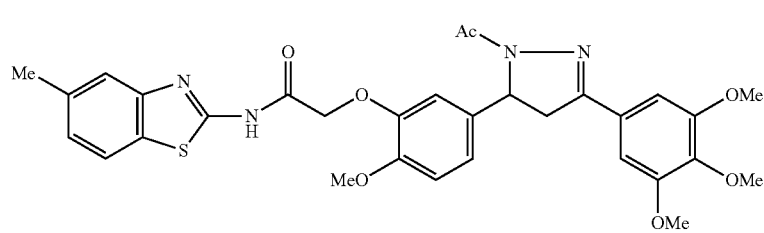
10m
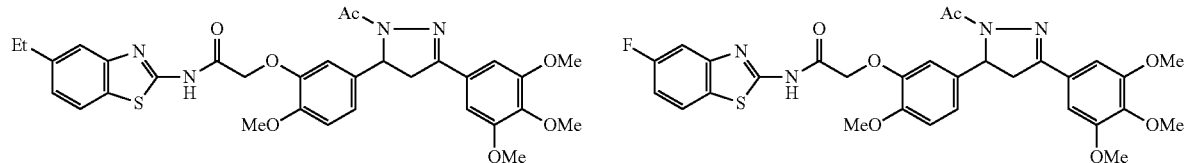
10n          10o
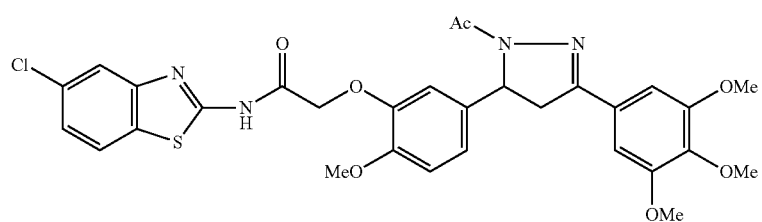
10p
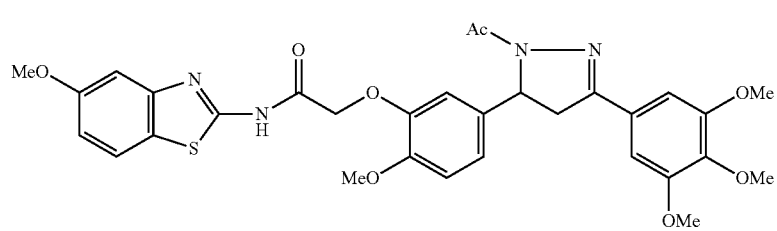
10q -continued
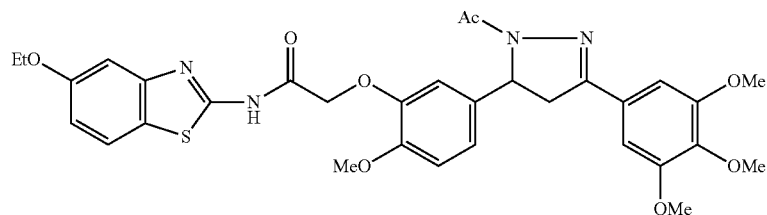
10r
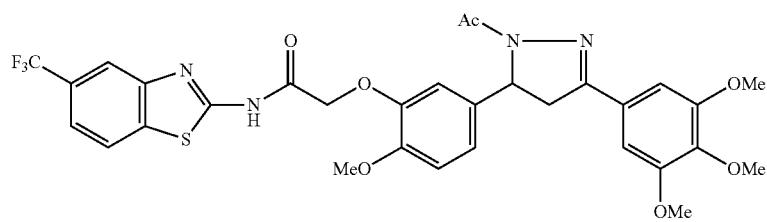
10s
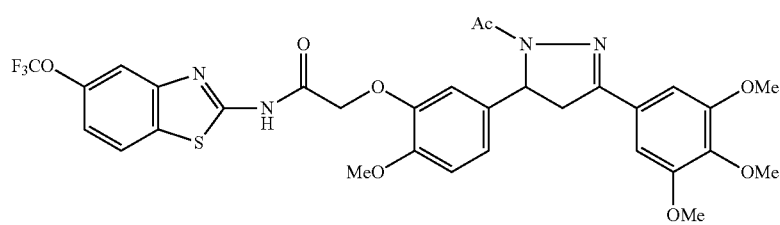
10t
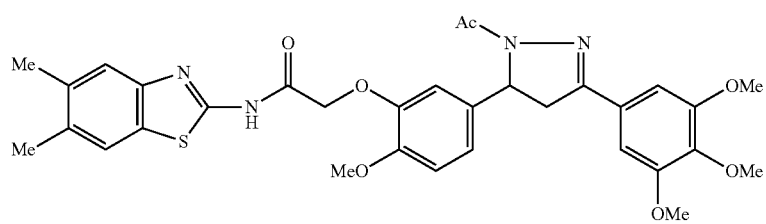
10u
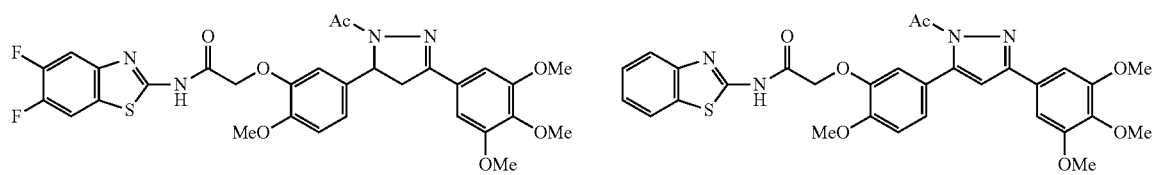
10v 11a
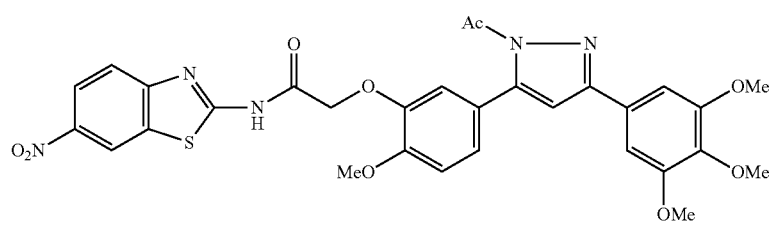
11b
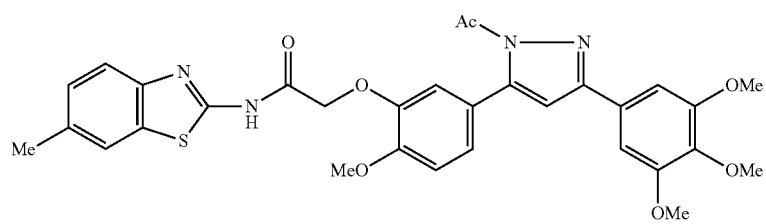
11c -continued
11d
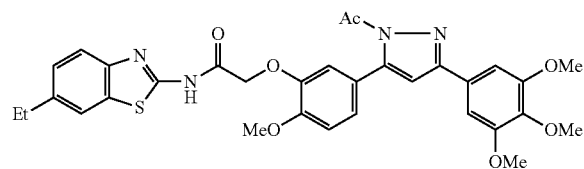
11e
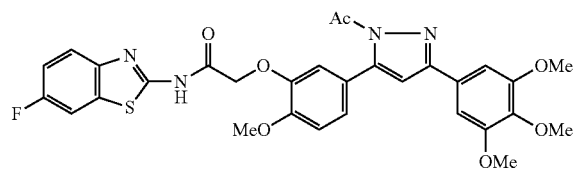
11f
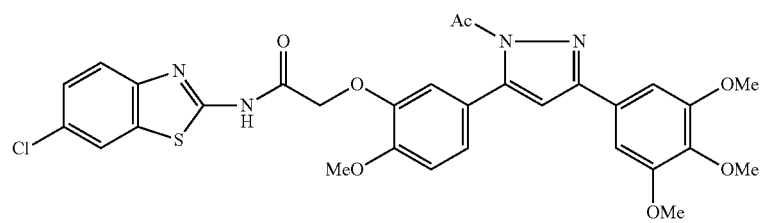
11g
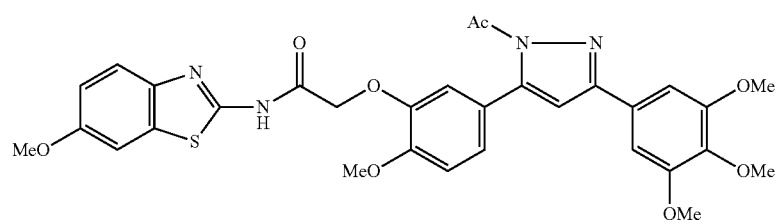
11h
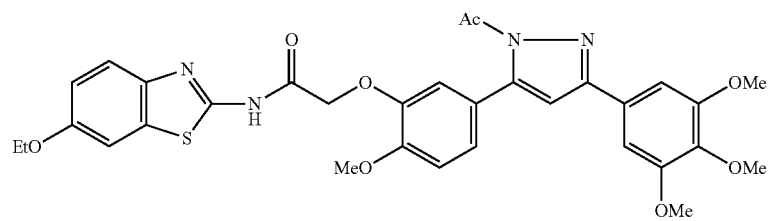
11i
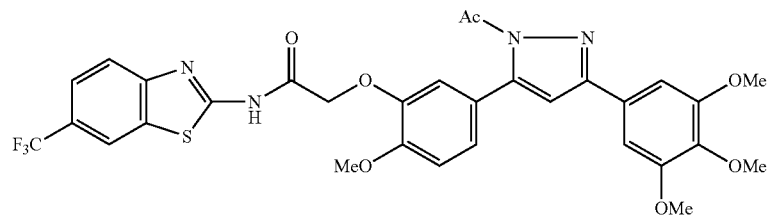
11j
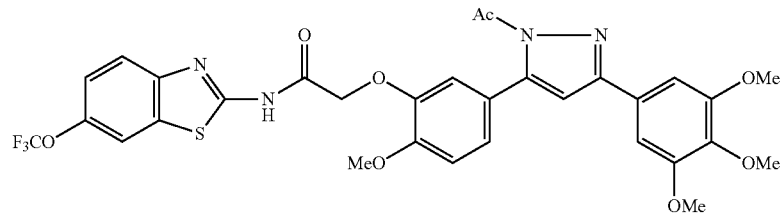
11k
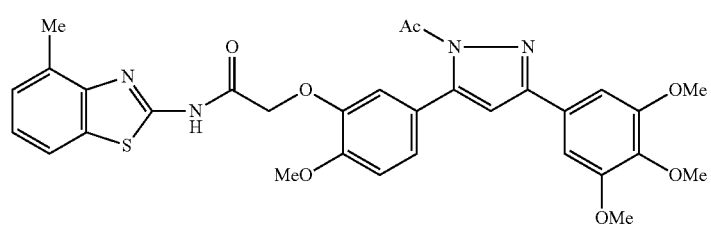

-continued
11l
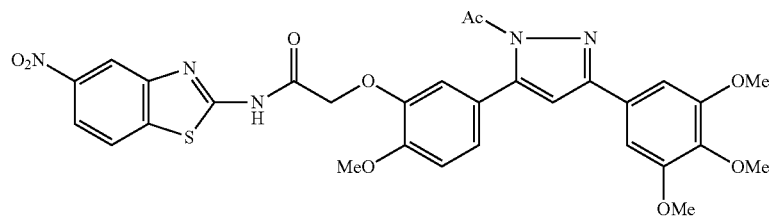
11m
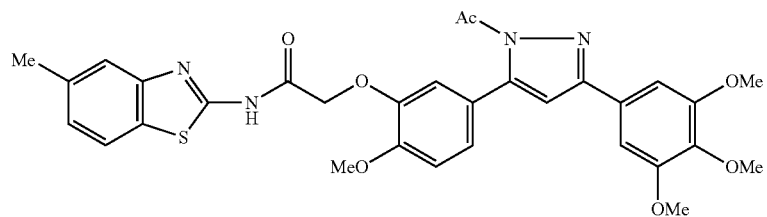
11n            11o
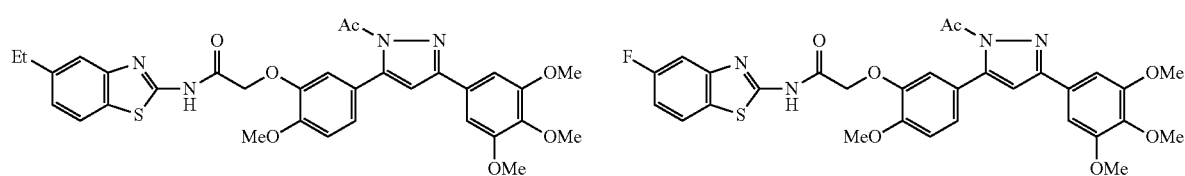
11p
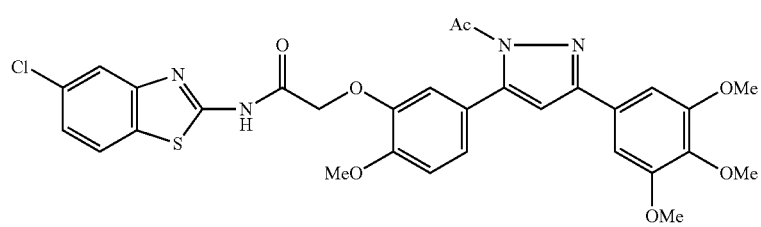
11q
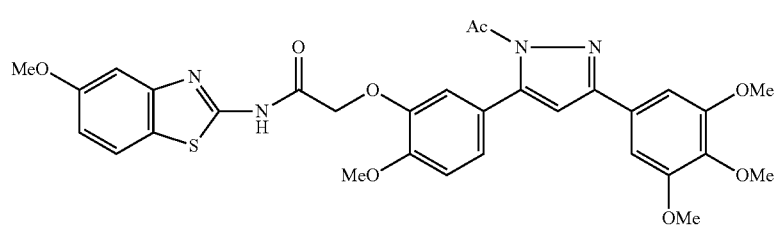
11r
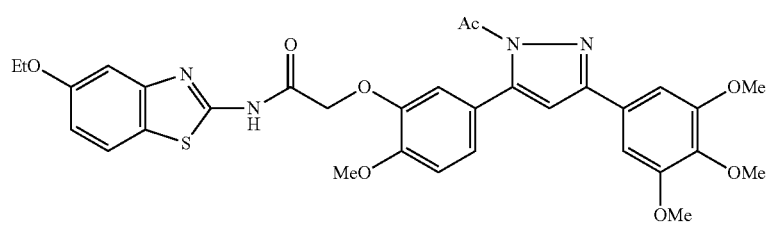
11s
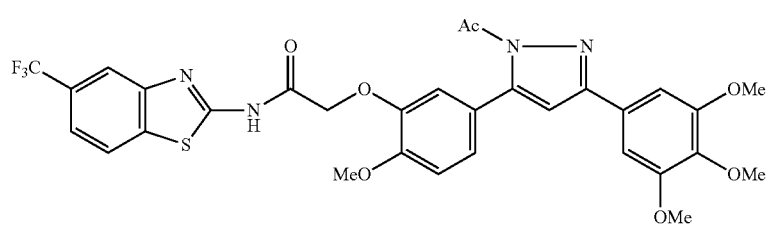

-continued
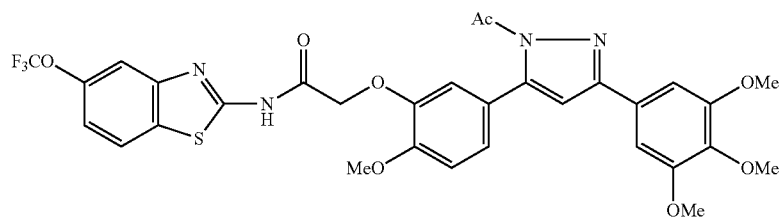
11t
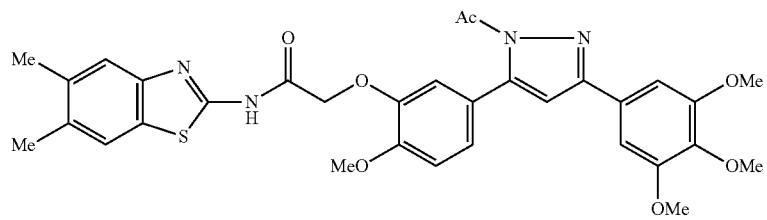
11u
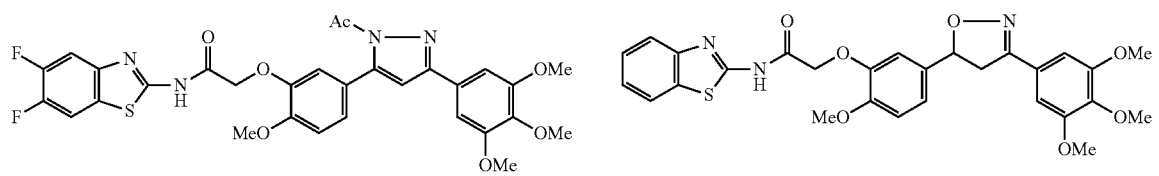
11v
12a
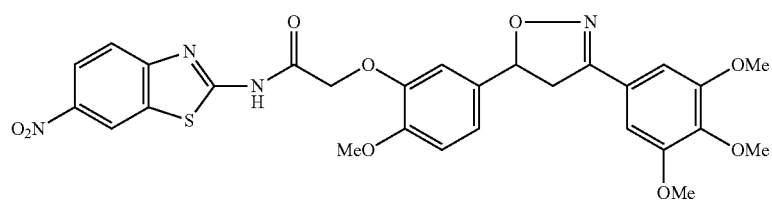
12b
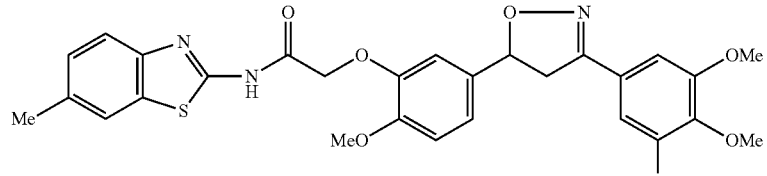
12c
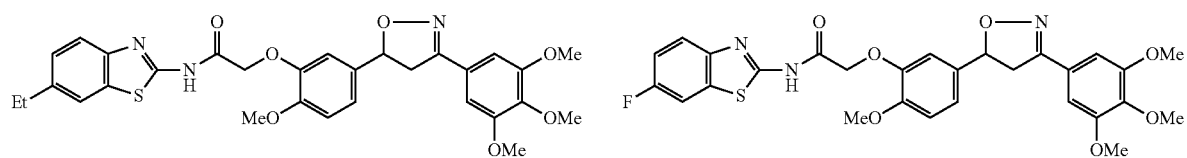
12d
12e
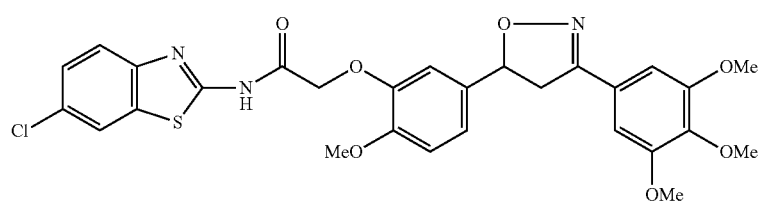
12f
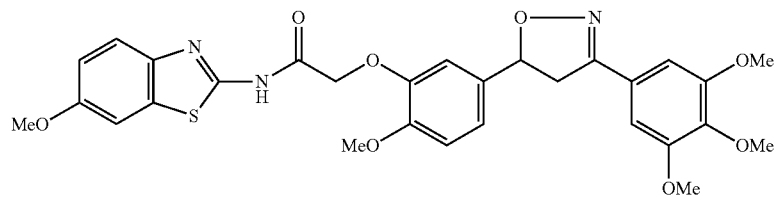
12g -continued
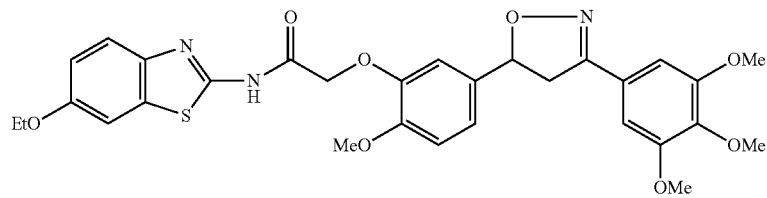
12h
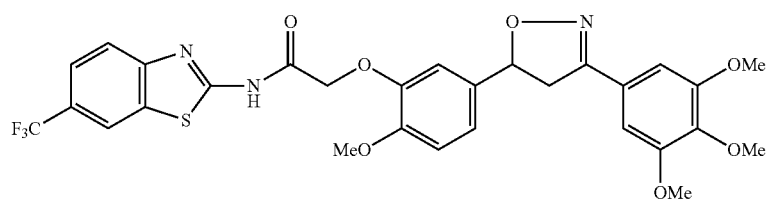
12i
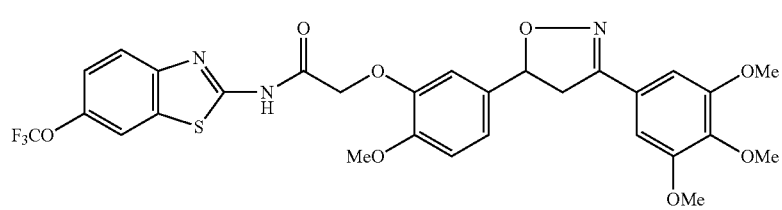
12j
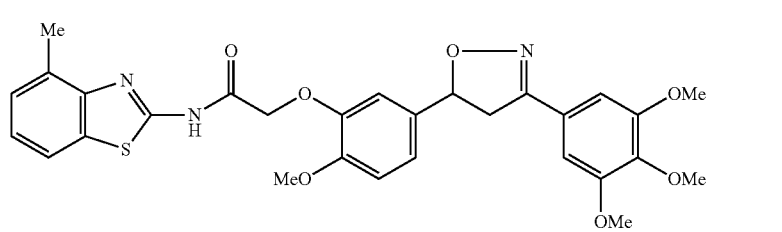
12k
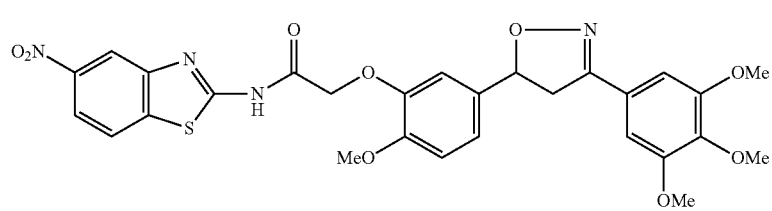
12l
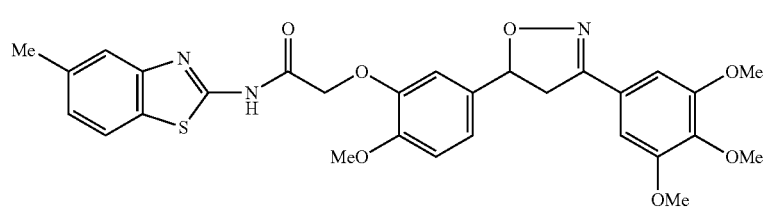
12m
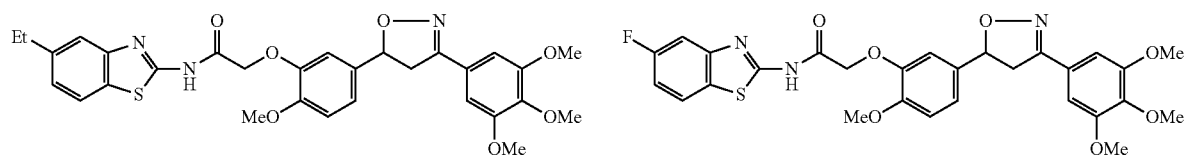
12n 12o
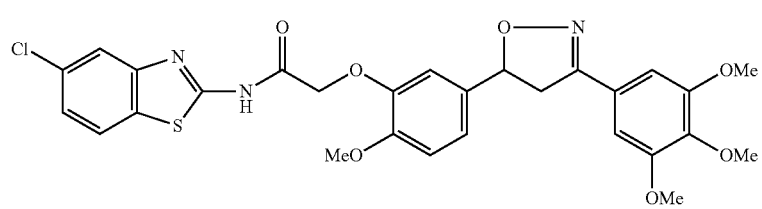
12p -continued
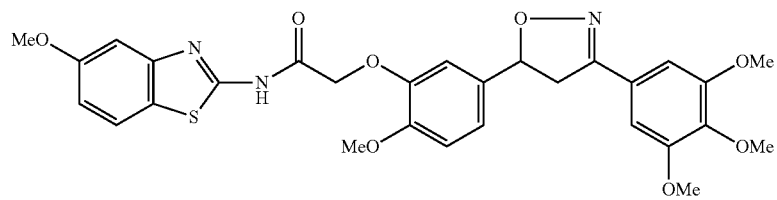
12q
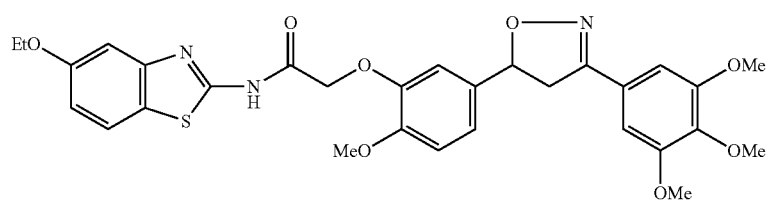
12r
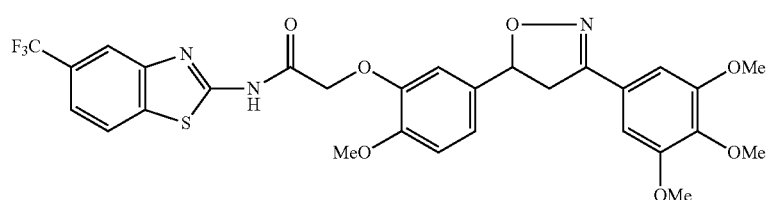
12s
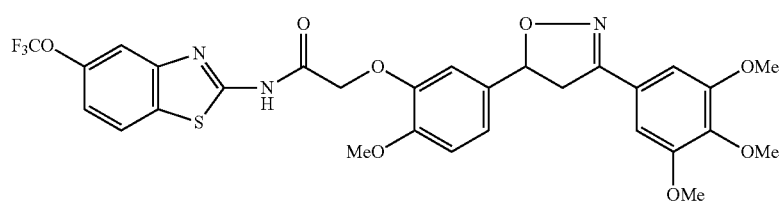
12t
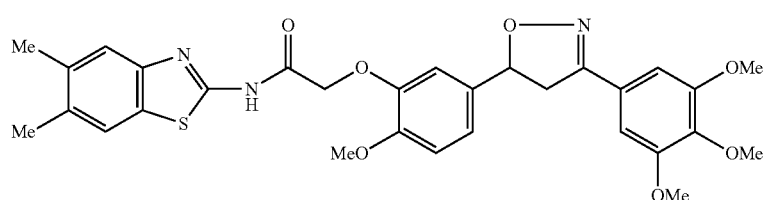
12u
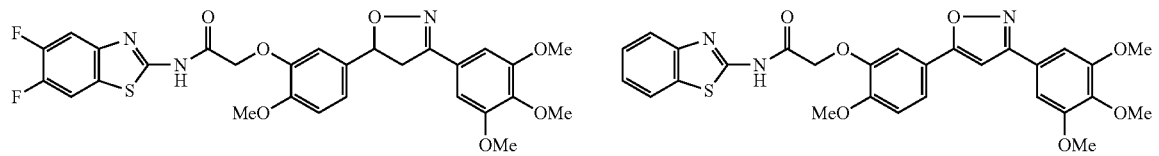
12v             13a
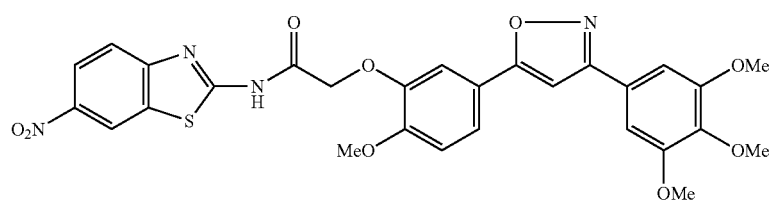
13b
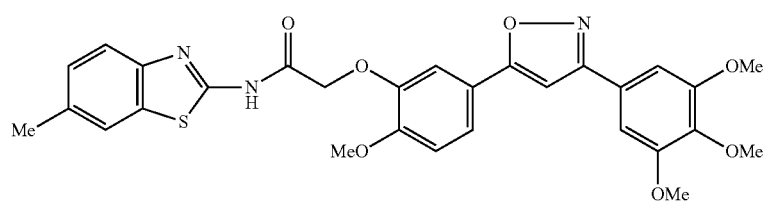
13c

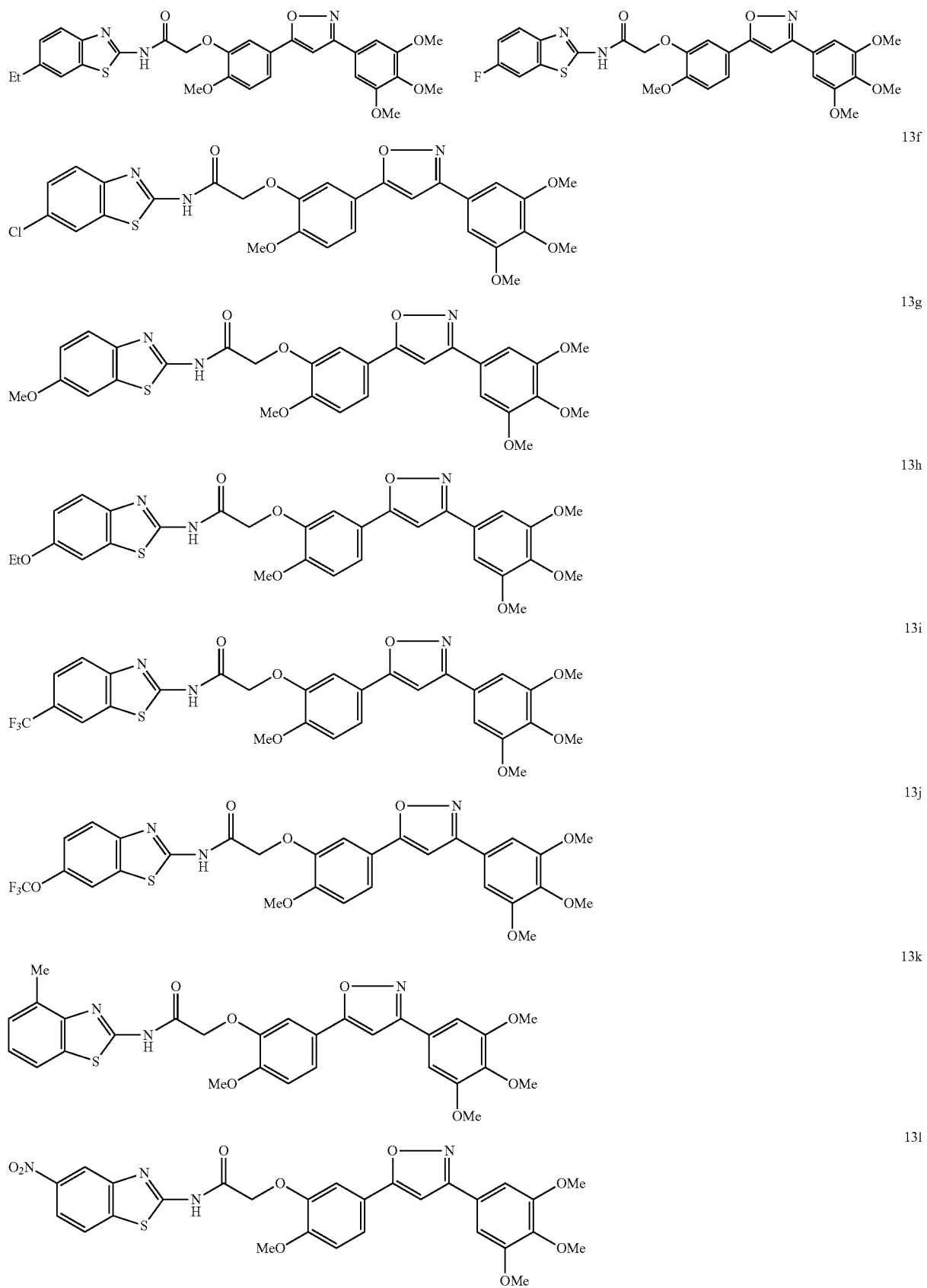

-continued
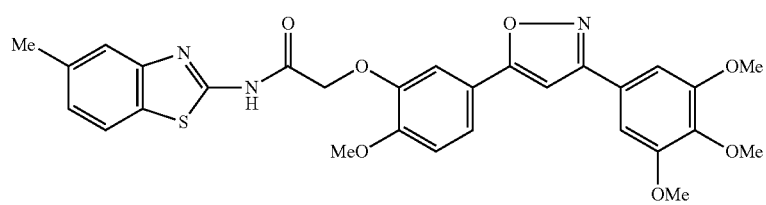
13m
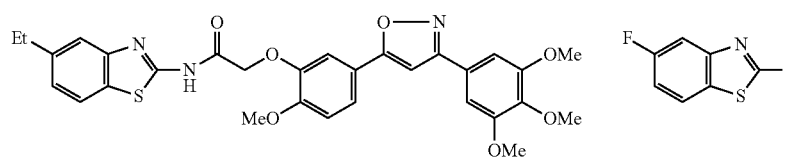
13n
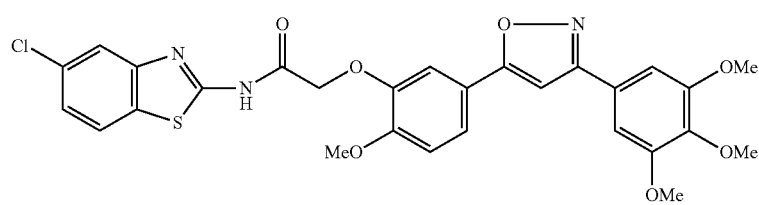
13o
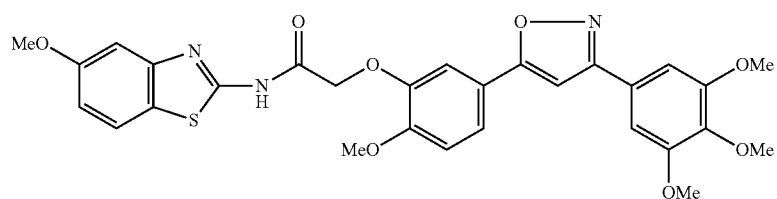
13p
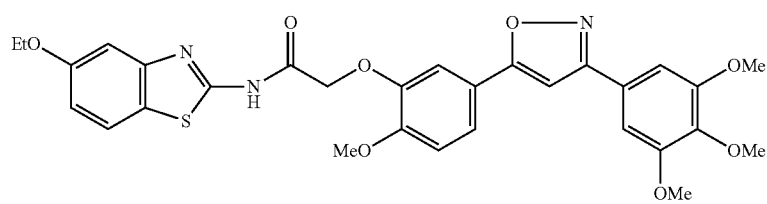
13q
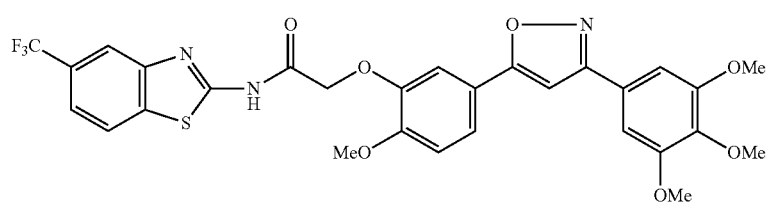
13r
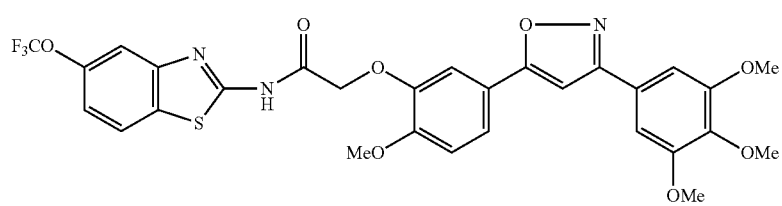
13s
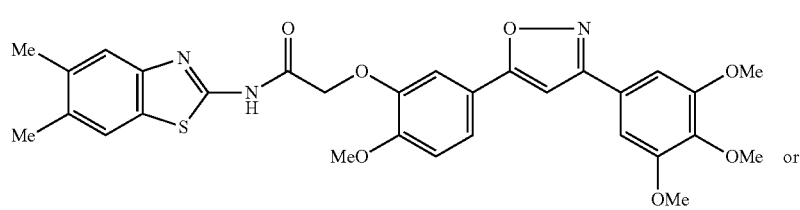
13t
13u
or

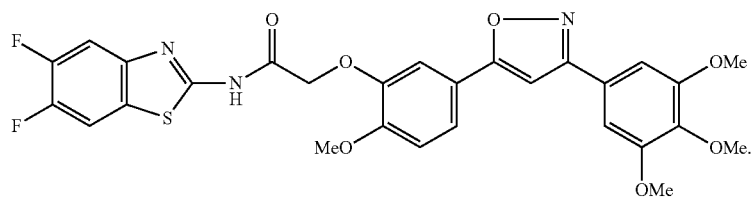

13v

-continued

3. A composition having in vitro anticancer activity against human cancer cell lines selected from the group consisting of leukemia cancer cell lines, non-small cell lung cancer cell lines, colon cancer cell lines, CNS cancer cell lines, melanoma cancer cell lines, ovarian cancer cell lines, renal cancer cell lines, prostate cancer cell lines and breast cancer cell lines, comprising an amidobenzothiazole of formula A:

formula A

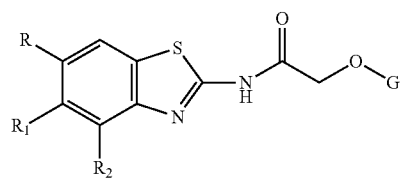

wherein:
R=H, alkoxy, halo, haloalkyl, halomethyl, or nitro,
$R_1$=H, alkoxy, halo, haloalkyl, halomethyl, or nitro,
$R_2$=H, alkoxy, halo, haloalkyl, halomethyl or nitro, and

G =

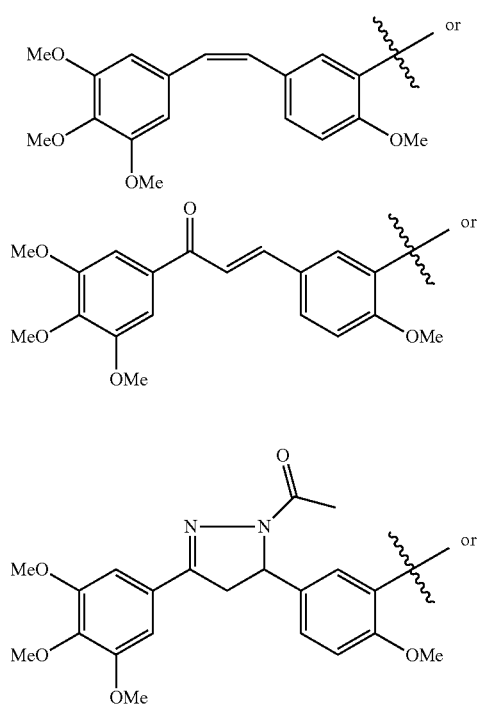

-continued

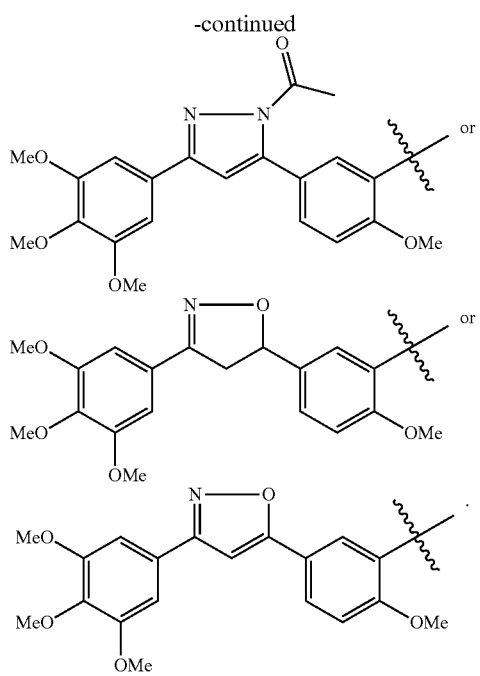

4. A composition having in vitro anticancer activity against human cancer cell lines selected from the group consisting of leukemia cancer cell lines, non-small cell lung cancer cell lines, colon cancer cell lines, CNS cancer cell lines, melanoma cancer cell lines, ovarian cancer cell lines, renal cancer cell in claim 2, wherein the amidobenzothiazole compound is:

N1-(1,3-benzothiazol-2-yl)-2-{2-methoxy-5-[(Z)-2-(3,4,5-trimethoxyphenyl)-1-ethenyl]phenoxy}acetamide (compound 8a);

N1-(6-fluoro-1,3-benzothiazol-2-yl)-2-{2-methoxy-5-[(Z)-2-(3,4,5-trimethoxy phenyl)-1-ethenyl]phenoxy}acetamide (compound 8e);

N1-(6-methoxy-1,3-benzothiazol-2-yl)-2-{2-methoxy-5-[(Z)-2-(3,4,5-trimethoxyphenyl)-1-ethenyl]phenoxy}acetamide (compound 8g);

N1-(6-(trifluoromethyl)-1,3-benzothiazol-2-yl)-2-{2-methoxy-5-[(Z)-2-(3,4,5-trimethoxyphenyl)-1-ethenyl]phenoxy}acetamide (compound 8i);

N1-(6-(trifluoromethoxy)-1,3-benzothiazol-2-yl)-2-{2-methoxy-5-[(Z)-2-(3,4,5-trimethoxyphenyl)-1-ethenyl]phenoxy}acetamide (compound 8j);

N1-(1,3-benzothiazol-2-yl)-2-{2-methoxy-5-[(E)-3-oxo-3-(3,4,5-trimethoxyphenyl)-1-propenyl]phenoxy}acetamide (compound 9a);

N1-(6-fluoro-1,3-benzothiazol-2-yl)-2-{2-methoxy-5-[(E)-3-oxo-3-(3,4,5-trimethoxy phenyl)-1-propenyl]phenoxy}acetamide (compound 9e);

N1-(6-methoxy-1,3-benzothiazol-2-yl)-2-{2-methoxy-5-[(E)-3-oxo-3-(3,4,5-trimethoxyphenyl)-1-propenyl]phenoxy}acetamide (compound 9g);

N1-(6-(trifluoromethyl)-1,3-benzothiazol-2-yl)-2-{2-methoxy-5-[(E)-3-oxo-3-(3,4,5-trimethoxyphenyl)-1-propenyl]phenoxy}acetamide (compound 9i);

N1-(6-(trifluoromethoxy)-1,3-benzothiazol-2-yl)-2-{2-methoxy-5-[(E)-3-oxo-3-(3,4,5-trimethoxyphenyl)-1-propenyl]phenoxy}acetamide (compound 9j); or N1-(6-(trifluoromethyl)-1,3-benzothiazol-2-yl)-2-{5-[1-acetyl-3-(3,4,5-trimethoxy phenyl)-4,5-dihydro-1H-5-pyrazolyl]-2-methoxyphenoxy}acetamide (compound 10i).

5. A process for the preparation of an amidobenzothiazole compound as claimed in claim 2:
comprising the steps of:
i. reacting a 2-aminobenzothiazole of formula 7a-7v with a compound selected from formula 1, 2, 3, 4, 5 and 6 in an organic solvent in the presence of 1-Ethyl-3-(3-Dimethylaminopropyl)carbodiimide (EDC) and 1-hydroxy benzotriazole (HOBT) at temperature in the range of 25 to 30° C. for a period in the range of 22 to 24 hrs;

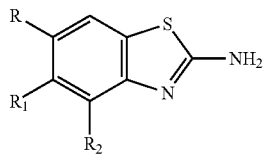

7a-v

7a: R = $R_1$ = $R_2$ = H,
7b: R = $NO_2$, $R_1$ = $R_2$ = H,
7c: R = $CH_3$, $R_1$ = $R_2$ = H,
7d: R = $C_2H_5$, $R_1$ = $R_2$ = H,
7e: R = F, $R_1$ = $R_2$ = H,
7f: R = Cl, $R_1$ = $R_2$ = H,
7g: R = $OCH_3$, $R_1$ = $R_2$ = H,
7h: R = $OC_2H_5$, $R_1$ = $R_2$ = H,
7i: R = $CF_3$, $R_1$ = $R_2$ = H,
7j: R = $OCF_3$, $R_1$ = $R_2$ = H,
7k: $R_2$ = $CH_3$, $R_1$ = R = H,

7l: $R_1$ = $NO_2$, R = $R_2$ = H,
7m: $R_1$ = $CH_3$, R = $R_2$ = H,
7n: $R_1$ = $C_2H_5$, R = $R_2$ = H,
7o: $R_1$ = F, R = $R_2$ = H,
7p: $R_1$ = Cl, R = $R_2$ = H,
7q: $R_1$ = $OCH_3$, R = $R_2$ = H,
7r: $R_1$ = $OC_2H_5$, R = $R_2$ = H,
7s: $R_1$ = $CF_3$, R = $R_2$ = H,
7t: $R_1$ = $OCF_3$ R = $R_2$ = H,
7u: $R_2$ = H, R = $R_2$ = $CH_3$,
7v: $R_2$ = H, R = $R_1$ = F,

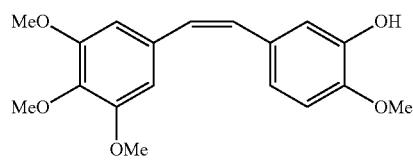

1

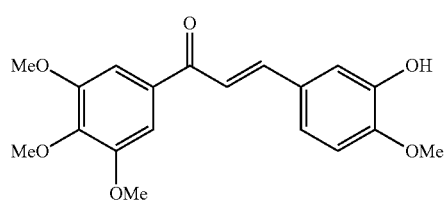

2

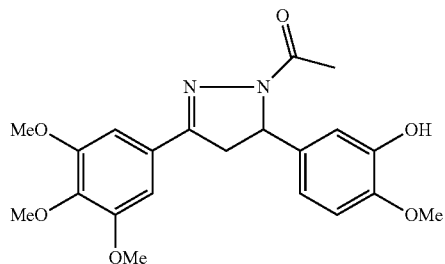

3

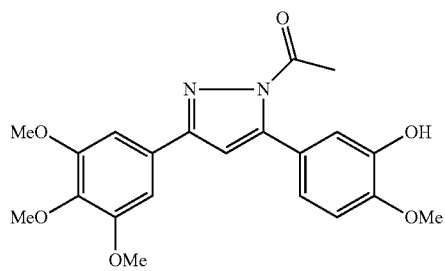

4

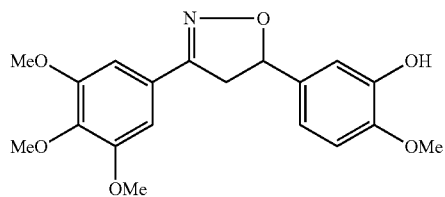

5

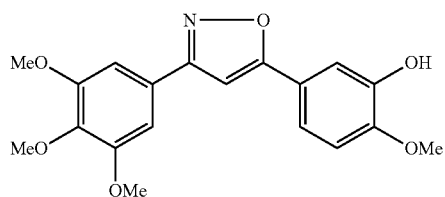

6 ii. adding water to the product of step (i) to form an aqueous mixture and extracting a crude product by mixing the aqueous mixture with organic solvent and then evaporating the organic solvent to obtain the crude product;

iii. purifying the crude product of step (ii) using column chromatography.

6. A process as claimed in claim 5, wherein the organic solvent used in step (i) or step (ii) is selected from the group consisting of dichloromethane, chloroform or N, N-dimethylformamide.

* * * * *